(12) United States Patent
Hsieh et al.

(10) Patent No.: US 8,404,445 B2
(45) Date of Patent: Mar. 26, 2013

(54) ANTIBODY LIBRARIES

(75) Inventors: Chung-Ming Hsieh, Newton, MA (US); Yuliya A. Kutskova, Northborough, MA (US); John E. Memmott, Framingham, MA (US)

(73) Assignee: AbbVie Inc., North Chicago, IL (US)

( * ) Notice: Subject to any disclaimer, the term of this patent is extended or adjusted under 35 U.S.C. 154(b) by 523 days.

(21) Appl. No.: 12/570,897

(22) Filed: Sep. 30, 2009

(65) Prior Publication Data

US 2010/0099103 A1    Apr. 22, 2010

Related U.S. Application Data

(60) Provisional application No. 61/101,483, filed on Sep. 30, 2008.

(51) Int. Cl.
*C12Q 1/68* (2006.01)
*C07H 21/04* (2006.01)

(52) U.S. Cl. .................. 435/6.12; 536/24.33

(58) Field of Classification Search ............... 435/6.12; 536/24.33
See application file for complete search history.

(56) References Cited

U.S. PATENT DOCUMENTS 6,518,018 B1   2/2003   Szostak et al.

FOREIGN PATENT DOCUMENTS

WO    WO99/51773 A1    10/1999
WO    2008/066752 A2   6/2008

OTHER PUBLICATIONS

Fukuda Isao et al: "In vitro evolution of single-chain antibodies using mRNA display", Nucleic Acids Research, vol. 34, No. 19, Nov. 2006, XP002639193.
Supplementary European Search Report from EP 09818451, dated Feb. 9, 2012.
Shan, Daming et al., "Characterization of scFv-Ig Constructs Generated from the Anti-CD20 mAb 1F5 Using Linker Peptides of Varying Lengths," The Journal of Immunology, vol. 162:6589-6595 (1999).
Yin, Jun et al., "Phagemid Encoded Small Molecules for High Throughput Screening of Chemical Libraries," J. Am. Chem. Soc., vol. 126:13570-13571 (2004).
International Search Report and Written Opinion for Application No. PCT/US09/59059, dated Apr. 16, 2010.

*Primary Examiner* — Amber D. Steele
(74) *Attorney, Agent, or Firm* — Lathrop & Gage LLP; James H. Velema, Esq.

(57) ABSTRACT

The present invention features improved in vitro RNA display libraries to allow reliable expression and selection of scFv antibody molecules from expression libraries. The scFv antibody libraries of the invention contain an optimized, shortened inter-domain linker that improves expression scFv antibody expression. The scFv antibody libraries also include short nucleic acid barcodes that allow for identification of individual library clones, libraries or subsets thereof. Primers for generating, amplifying and spectratyping the scFv antibody libraries of the invention are also provided.

45 Claims, 31 Drawing Sheets

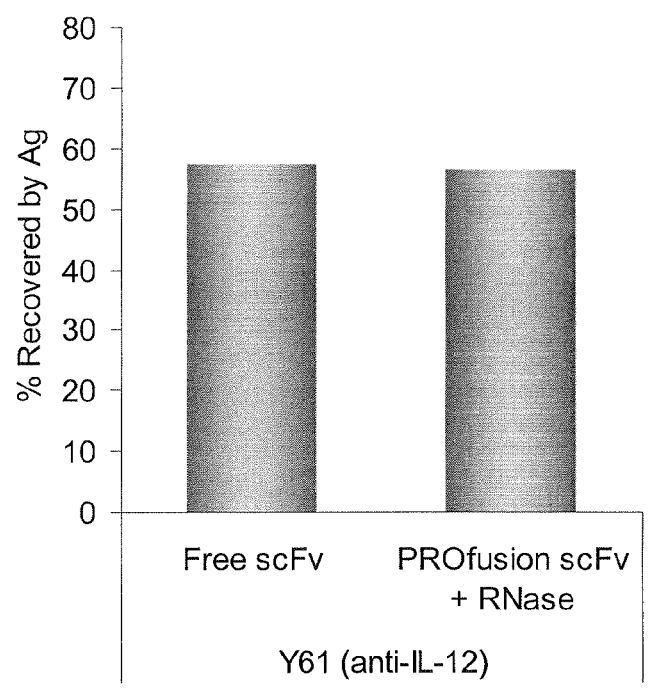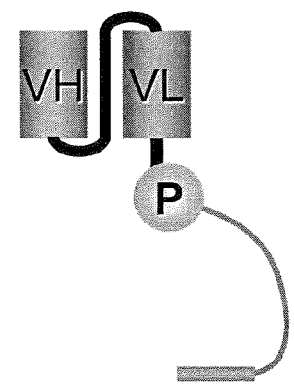
Fig. 5

```
              1                                                          60
17_9-tag1  TAATACGACTCACTATAGGGACAATTACTATTTACAATTACAGCGTGGGTACCATGGAAG
17_9-tag2  TAATACGACTCACTATAGGGACAATTACTATTTACAATTACAGTGTTGCGACCATGGAAG
17_9-tag3  TAATACGACTCACTATAGGGACAATTACTATTTACAATTACAGGCTTTGGACCATGGAAG
17_9-tag4  TAATACGACTCACTATAGGGACAATTACTATTTACAATTACAGCTTCTTCACCATGGAAG
           T7 Promoter            TMV-UTR                  Tags   Kozak 17/9
```

[T7] [TMV] ['TAG'] [Kozak] [17/9]

[T7]

[T7] [TMV] ['TAG']

*Fig. 7*

| R1 Output Tags | R2 Output Tags | R3 Output Tags |
|---|---|---|
| CGGTCCCT | CCGCGCGG | CCGTCTTT |
| CTCGTTTG | CCGGGTTG | CCTCTTGT |
| CTCTGTGT | CCTCCCGT | CCTGTGTT |
| CTGTGTTG | CGGGCTGG | CGCTGGTT |
| CTTTTGCT | CGTCGGTC | CGTCTGGT |
| GCCGCGGT | CGTGGGTT | CTCGCGCC |
| GCGCTGT | CGTGGGTT | CTCTTGCG |
| GGCGCTGT | CTCCTGGC | GCCTTCTC |
| GGGTGTCT | GCCCGTCT | GCCTTTTT |
| GGTTCTTT | GCCTGTTC | GCGGCCTT |
| GGTTGCGG | GCGCTCGT | GCGTGGGT |
| GTGCTTCT | GCGGCCCT | GCGTGGGT |
| GTGTGCGT | GCGGCTTG | GCGTGGGT |
| GTGTTCTC | GCTTCTCG | GCTTCTTC |
| GTTTGCGC | GGCCTTTG | GCTTTCTT |
| TCGCGTCC | GGCTGTCC | GGCCGCGG |
| TCGTGCGT | GGCTT ATG | GGCGCGCG |
| TGCCCGCG | GGCTT ATG | GGCGGGTG |
| TGCCGGTG | GGGCGGCT | GGCTTTGG |
| TGGTCGCT | GGGTGTGT | GGGCCTTG |
| TGGTCTTG | GGTTGTGC | GGGGGCGT |
| TTTGCTGC | GTCGGGCG | GGTCCTTC |
|  | GTCGGGTT | GTGCGTCG |
|  | GTGTGCTC | GTGTCTGT |
|  | GTGTTTTT | GTGTTGCG |
|  | TGCTTTGT | GTTCGTCG |
|  | TGCTTTGT | GTTCTTGC |
|  | TGCTTTTG | GTTTGGCT |
|  | TGTTTTCG | TCGTGCGT |
|  | TTCGGCTT | TGTCTGTG |
|  | TTGGGCTT | TTCTCCTT |
|  | TTGTGTTT | TTGGCCTG |
|  | TTTGGCTC | TTGTTGGC |
|  | TTTGGCTC | TTTTGCTC |
|  | TTTTGTTG |  |

*Fig. 8*

D2E7-scCk
T7 TMV-UTR | D2 VH | GS | E7 VL | Cκ | FLAG | Linker site | Poly A
2SE7-scCk Chimera
T7 TMV-UTR | 2S VH | GS | E7 VL | Cκ | FLAG | Linker site | Poly A
D2D4-scCk Chimera
T7 TMV-UTR | D2 VH | GS | D4 VL | Cκ | FLAG | Linker site | Poly A
2SD4-scCk
T7 TMV-UTR | 2S VH | GS | D4 VL | Cκ | FLAG | Linker site | Poly A
*Fig. 10*

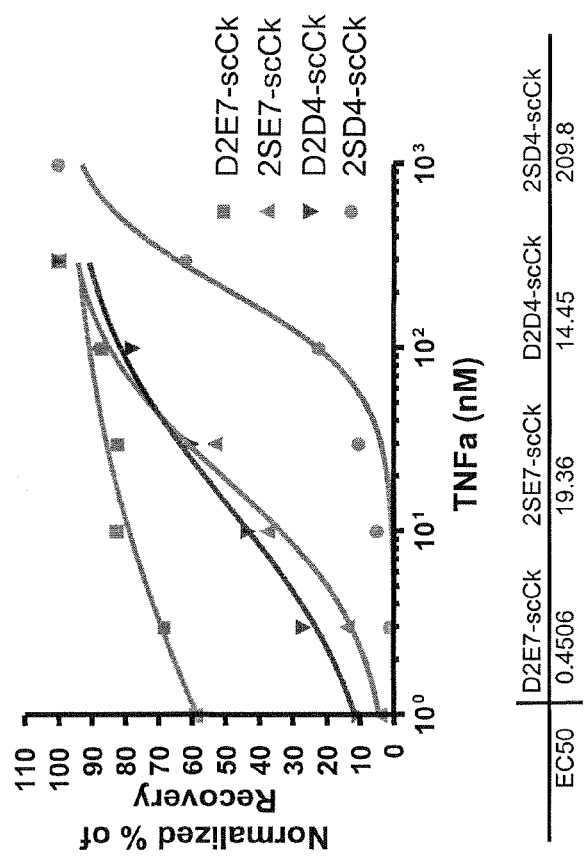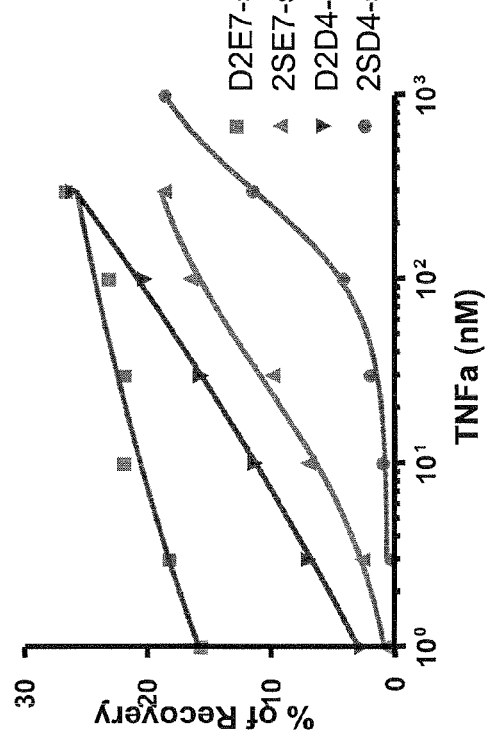
Fig. 11

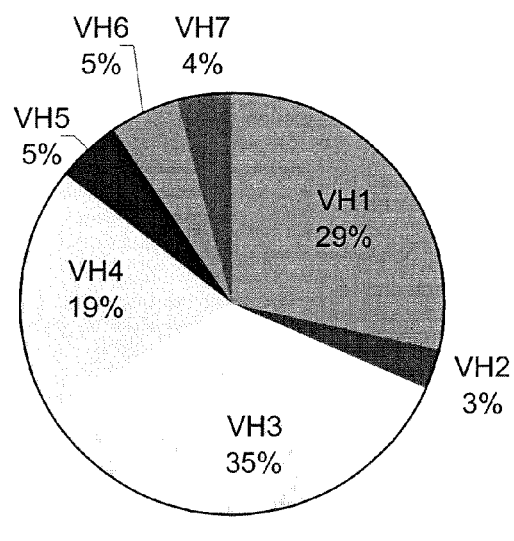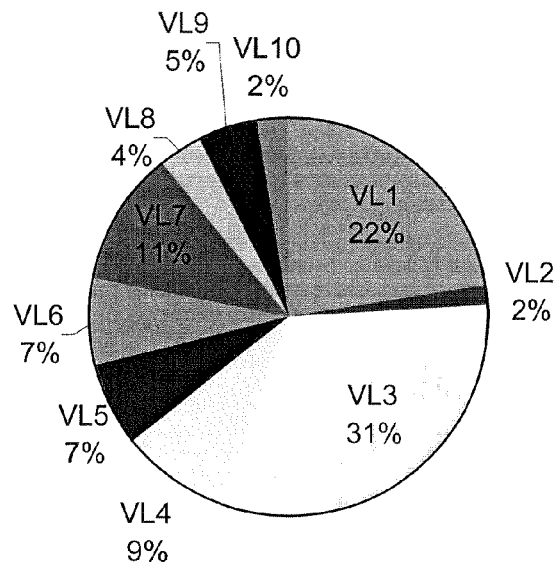
Fig. 23

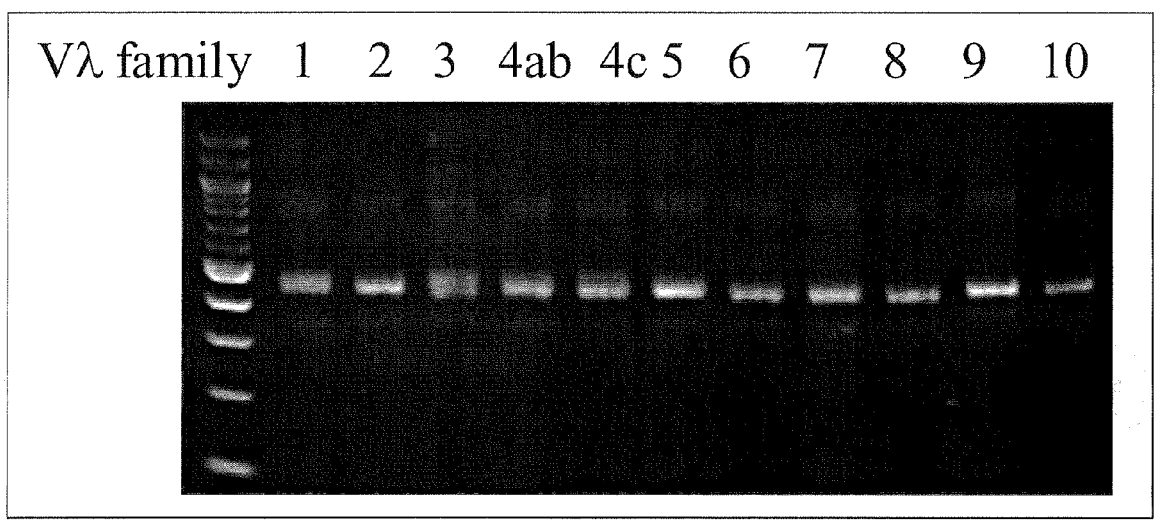
*Fig. 27*

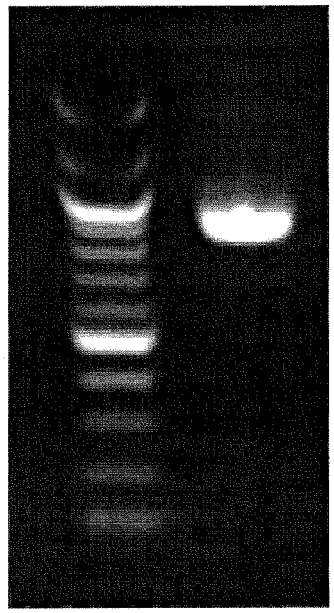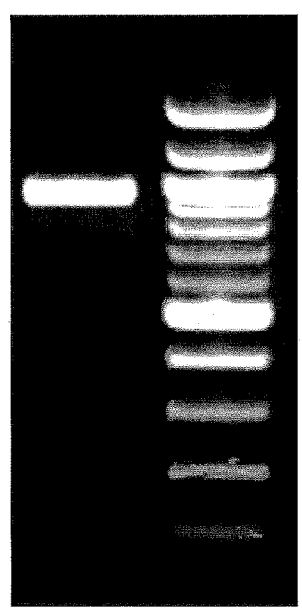
Fig. 28

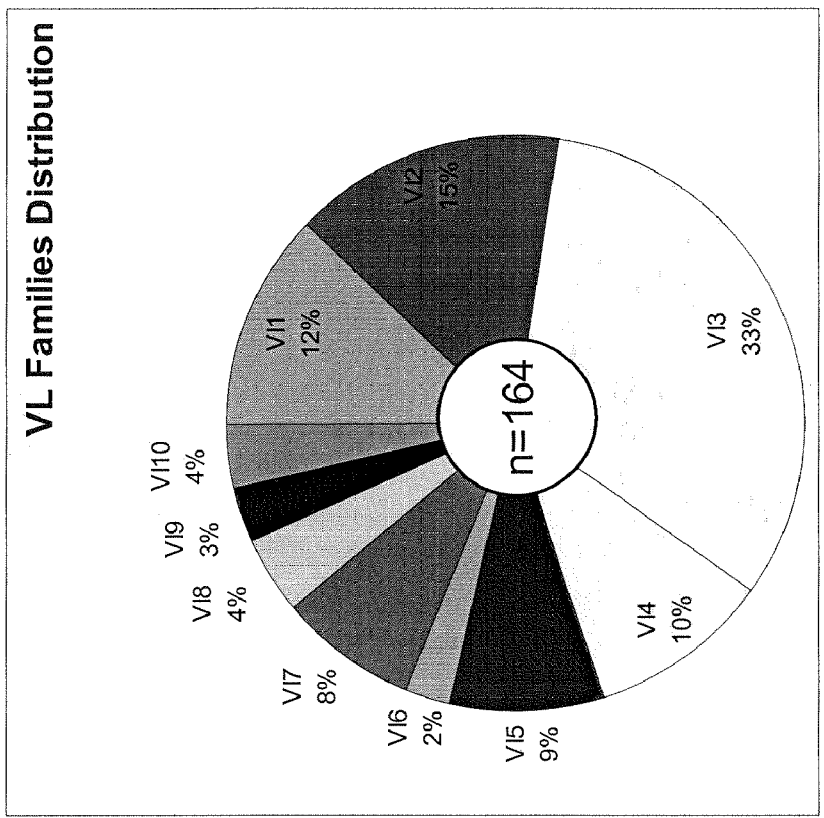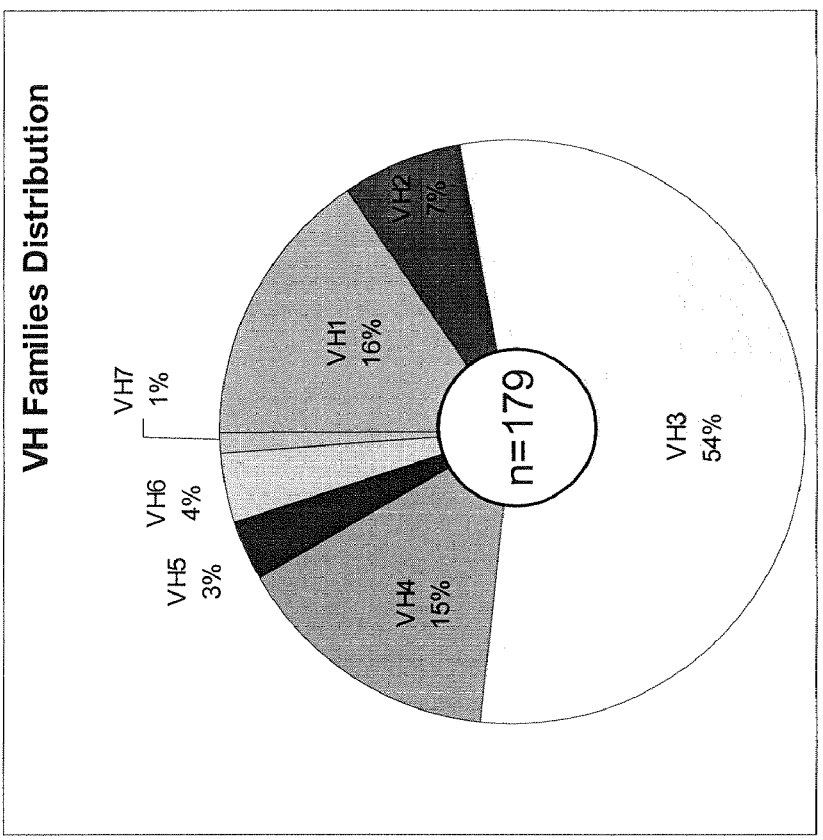
Fig. 30

ANTIBODY LIBRARIES

RELATED APPLICATIONS

This application claims priority to U.S. Provisional Application No. 61/101,483, filed Sep. 30, 2008, the contents of which are hereby incorporated by reference.

FIELD OF THE INVENTION

The invention relates to improved antibody libraries and methods and materials for making same.

BACKGROUND OF THE INVENTION

Antibodies that bind with high specificity and affinity to almost any structural epitope are routinely used as research tools and as FDA approved therapeutics. As a result, therapeutic and diagnostic monoclonal antibodies constitute a multi-billion dollar market worldwide.

Classical methods of immunizing animals to obtain antibodies are slow and cumbersome. As a consequence, several methods have been developed for ex vivo selection of an antibody to a desired target molecule using synthetic antibody libraries. In some methods, libraries of antibodies, or fragments thereof, are displayed on the surface of an organism (for example, a yeast cell, bacterial cell or mammalian cell) or a sub-microscopic agent (for example, a bacteriophage or virus), and the organism or sub-microscopic agent is selected for expression of the desired antibody. In other methods, antibody libraries are expressed and selected in a cell free in vitro system. Current in vitro expression systems, although good at expressing single antibody variable domains, are inefficient at expressing multi-domain antibodies such as single chain antibody (scFv) molecules. This is due to both the structure of current scFv antibody libraries and to the reaction conditions of the current in vitro expression systems.

There is, therefore, a need in the art for improved antibody libraries for selection of scFv antibodies against a desired target.

SUMMARY OF THE INVENTION

The invention solves the foregoing problems by providing improved in vitro display RNA libraries to allow reliable expression and selection of scFv antibody molecules.

The invention has several advantages, which include but are not limited to, the following:
  providing an improved in vitro display scFv antibody library containing an optimized inter-domain linker for improved expression;
  providing an improved in vitro display scFv antibody library containing short nucleic acid barcodes;
  providing primers to generate the improved in vitro display scFv antibody libraries;
  providing primers to spectratype the CDR3 regions of the heavy chain variable regions of the scFv antibody molecules in the libraries of the invention; and
  methods of making the improved in vitro display libraries.

In one aspect, the invention provides an oligonucleotide consisting of a nucleic acid sequence as set forth in any one of SEQ ID NOs: 1-14, 19-42, and 58-210. In another aspect, the invention provides an oligonucleotide comprising a nucleic acid sequence as set forth in any one of SEQ ID NOs: 1-14, 19-42, and 58-210.

In another aspect, the invention provides an oligonucleotide consisting of a nucleic acid sequence as set forth in any one of SEQ ID NOs: 14-16, and 43-57. In another aspect, the invention provides an oligonucleotide comprising a nucleic acid sequence as set forth in any one of SEQ ID NOs: 14-16, and 43-57.

In yet another aspect, the invention provides an oligonucleotide consisting of a nucleic acid sequence as set forth in SEQ ID NOs: 17 or 18. In another aspect, the invention provides an oligonucleotide comprising a nucleic acid sequence as set forth in SEQ ID NOs: 17 or 18.

In an embodiment, the invention provides for the use of any of the sequences set forth in SEQ ID NOs: 1-210 for library amplification, library reverse transcription, and/or library spectratyping.

In another aspect, the invention provides for a nucleic acid library for expression of single chain antibodies (scFv), the library comprising a repertoire of sequences encoding heavy chain variable domains and light chain variable domains, wherein each member of said library contains an open reading frame comprising a heavy chain variable domain, a light chain variable domain, and a linker region, and wherein said library is generated using one or more of the oligonucleotides set forth in SEQ ID NOs: 1-210.

In an embodiment, the library further comprises a linker region that encodes less than 20 amino acids. In another embodiment, the library further comprises a linker region that encodes 15 amino acids.

In an embodiment, each member of the library further comprises a promoter operably linked to the open reading frame. In another embodiment, the promoter is selected from the group consisting of T7, SP6, and T3. In yet another embodiment, the promoter is a T7 promoter.

In an embodiment, each member of the library further comprises a 5'untranslated region (5'UTR) capable of enhancing transcription of a gene to which it is operably linked. In another embodiment, the 5'UTR is a Tobacco Mosaic Virus 5'UTR or an active fragment thereof. In another embodiment, each member of the library further comprises a polyadenine sequence.

In yet another embodiment, the library further comprises a nucleic acid barcode. In another embodiment, the nucleic acid barcode comprises 8 nucleotides.

In another embodiment, each member of the library further comprises a nucleic acid sequence encoding an epitope tag. In yet another embodiment, the epitope tag is a FLAG tag. In yet another embodiment, the nucleic acid sequence is part of the linker region of the scFv. In another embodiment, the library further comprises a nucleic acid sequence encoding an antibody constant region, or fragment thereof.

In an embodiment, the library further comprises a ribosome pause sequence.

In an embodiment, the library further comprises a peptide acceptor. In another embodiment, the peptide acceptor is covalently attached via a linker comprising a Psoralen C6 molecule. In yet another embodiment, the linker is 5' (Psoralen C6) 2'Ome (U AGC GGA UGC) (SEQ ID NO: 211) XXX XXX CC (Puromycin), wherein X is a triethylene glycol linker or PEG-150 and CC is a DNA backbone.

In another aspect, the invention provides for a method of producing a nucleic acid library for expression of single chain antibodies (scFv) comprising (a) providing a nucleic acid composition, wherein at least a portion of the nucleic acids in the composition comprises at least one open reading frame encoding an antibody variable domain and (b) amplifying a plurality of antibody variable domains using one or more oligonucleotides set forth in SEQ ID NOs 1-210.

In another aspect, the invention provides for a method of spectratyping a nucleic acid comprising at least one open reading frame encoding an antibody variable domain comprising (a) providing a nucleic acid composition, wherein at least a portion of the nucleic acids in said composition comprise at least one open reading frame encoding an antibody variable domain and (b), amplifying the CDR3 regions of said variable domains using one or more oligonucleotides set forth in SEQ ID NOs 1-210.

BRIEF DESCRIPTION OF THE DRAWINGS

FIG. 5 depicts the results showing that an scFv attached in an mRNA-scFv molecule format is functionally equivalent to a free scFv molecule.

FIG. 7 depicts the exemplary constructs and control sequences.

FIG. 8 depicts the random tag sequences identified in three rounds of selection.

FIG. 10 depicts the chimeras between D2E7 and 2SD4.

FIG. 11 depicts the $K_D$ curves for different TNFα binders.

FIG. 23 depicts the VH and Vλ, family distribution in the constructed naive human PBMC lambda scFv PROfusion library.

FIG. 27 depicts the Vλ, family-specific PCR fragments in the constructed naive human lymph node kappa and lambda scFv PROfusion libraries.

FIG. 28 depicts the VH-Vκ and VH-Vλ, scFv PCR products in the constructed naive human lymph node kappa and lambda scFv PROfusion libraries.

FIG. 30 depicts the VH and Vλ, family distribution in the constructed VH-Vλ, scFv library.

DETAILED DESCRIPTION OF THE INVENTION

Figure 1:
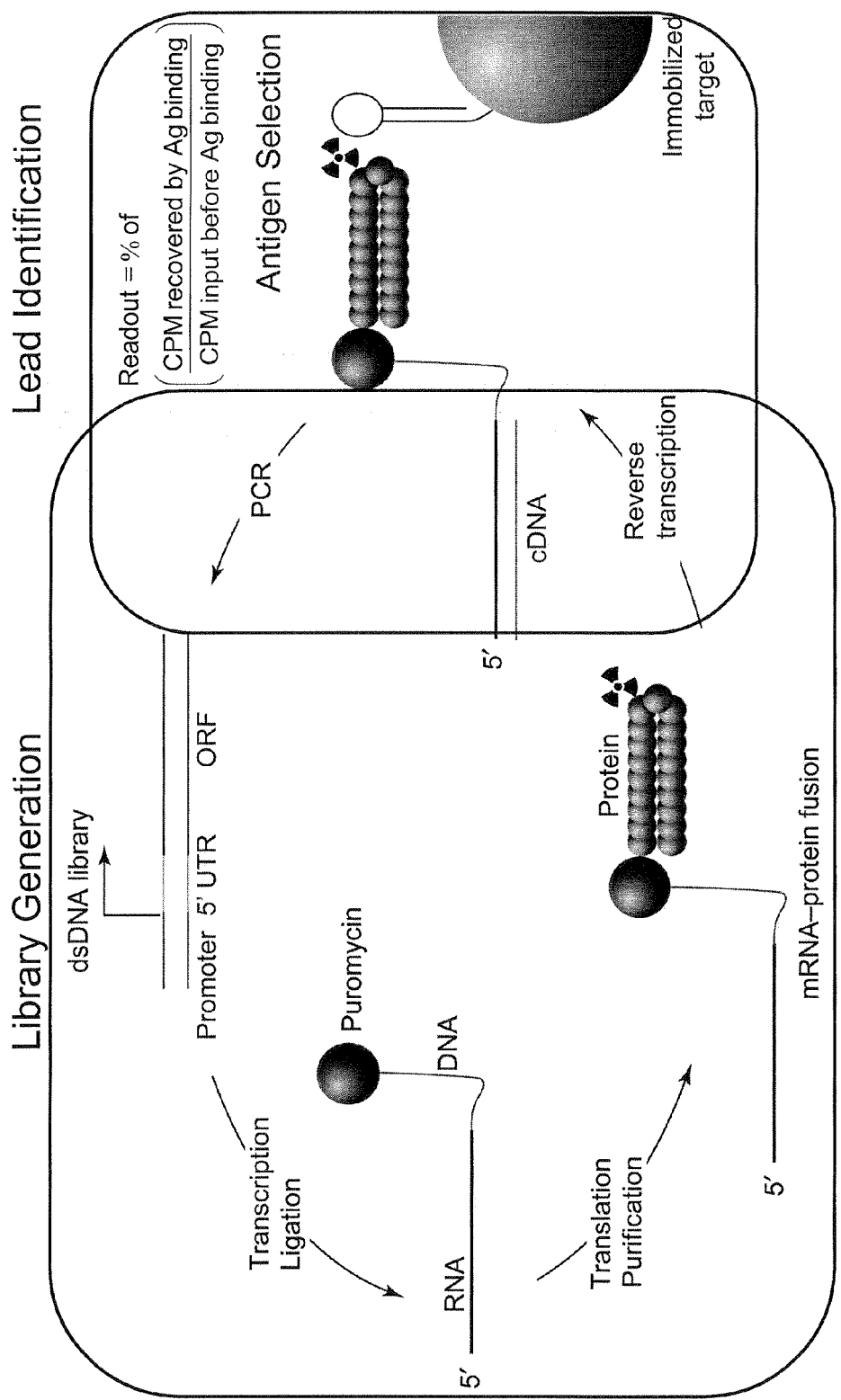
FIG. 1 depicts a general scheme for the mRNA-scFv display technology in certain embodiments of the invention.

In order that the present invention may be more readily understood, certain terms are first defined.

I. Definitions

The term "antibody" includes monoclonal antibodies (including full length monoclonal antibodies), polyclonal antibodies, multispecific antibodies (e.g., bispecific antibodies), chimeric antibodies, CDR-grafted antibodies, humanized antibodies, human antibodies, murine antibodies and fragments thereof, for example, an antibody light chain (VL), an antibody heavy chain (VH), a single chain antibody (scFv), an F(ab')2 fragment, an Fab fragment, an Fd fragment, an Fv fragment, and a single domain antibody fragment (DAb).

The term "antibody library" refers to a plurality of DNA or RNA molecules containing an open reading frame (ORF) that encodes an antibody or fragment thereof. It also includes a plurality of antibody proteins and nucleic acid/antibody fusion molecules expressed from said DNA or RNA molecules.

The term "heavy chain variable domain" refers to the nucleic acid encoding an antibody heavy chain variable region and to the protein product of said nucleic acid.

The term "light chain variable domain" refers to the nucleic acid encoding an antibody light chain variable region and to the protein product of said nucleic acid.

The term "spectratyping" refers to a PCR based method that separates genetic sequences encoding antibodies on the basis of CDR3 length. Changes in CDR3 length distribution is correlated with changes in the antibody repertoire (Janeway et al. "Immunobiology", 5th ed. Garland Publishing, New York and London, (2001)).

The term "epitope tag" refers a short amino acid sequence specifically recognized by an antibody that is attached chemically or genetically to a molecule to allow for its detection by said antibody, for example, a FLAG tag, an HA tag, a MYC tag or a T7 tag.

The term "nucleic acid barcode" refers to a short nucleic acid included in the untranslated region of the libraries of the invention. The barcode is a random or predetermined sequence that serves to provide a unique identifier to an individual clone or a plurality of library members.

The term "non-antibody sequences" refers to any nucleic acid or amino acid sequences that appear in the antibody libraries of the invention that are not part of the original antibody sequence. Such sequences include, for example, epitope tags, or nucleic acid barcodes.

The term "control sequences" refers to the nucleic acid sequences or genetic elements necessary for the expression of an operably linked coding sequence in a particular host organism, sub-microscopic agent or in vitro expression system. Such sequences are well known in the art. The control sequences that are suitable for prokaryotes, for example, include a promoter, optionally an operator sequence, and a ribosome binding site. Eukaryotic cells are known to utilize promoters, polyadenylation signals, and enhancers. Nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous. However, enhancers do not have to be contiguous. Linking is accomplished by ligation at convenient restriction sites, for example. If such sites do not exist, synthetic oligonucleotide adaptors or linkers are used in accordance with conventional practice.

The term "specific binding" or "specifically binds to" refers to the ability of a binding molecule to bind to a target with an affinity of at least about $1\times10^{-6}$ M, $1\times10^{-7}$ M, $1\times10^{-8}$ M, $1\times10^{-9}$ M, $1\times10^{-10}$ M, $1\times10^{-10}$ M, $1\times10^{-12}$ M, or more, and/or bind to a target with an affinity that is at least two-fold greater than its affinity for a nonspecific antigen.

The term "target" refers to an antigen or epitope recognized by an antibody. Targets include, for example, any peptide, proteins, saccharides, nucleic acids, lipids, and small molecules for which a specific antibody is generated. In one embodiment, antibodies are against a human protein, for example, TNFalpha, IL-12 or IL-1alpha.

A "conservative amino acid substitution" is one in which an amino acid residue is replaced with an amino acid residue having a similar side chain. Families of amino acid residues having similar side chains have been defined in the art.

The term "RNA display" or "mRNA display" refers to an in vitro technique wherein, expressed proteins or peptides are linked covalently or by tight non-covalent interaction to their encoding mRNA to form "RNA/protein fusion" molecules. The protein or peptide component of an RNA/protein fusion is selected for binding to a desired target and the identity of the protein or peptide determined by sequencing of the attached encoding mRNA component. Such methods are well known in the art and are described, for example, in U.S. Pat. Nos. 7,195,880; 6,951,725; 7,078,197; 7,022,479, 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315.

The term "single chain Fv antibody" or "scFv" refers to an antigen binding portion of a light chain variable region and an antigen binding portion of a heavy chain variable region, joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. U.S.A 85:5879-5883).

The term "functional moiety" refers to any biological or chemical entity that imparts additional functionality to a molecule to which it is attached.

The term "selecting" refers to substantially partitioning a molecule from other molecules in a population. As used herein, a "selecting" step provides at least a 2-fold, preferably, a 30-fold, more preferably, a 100-fold, and, most preferably, a 1000-fold enrichment of a desired molecule relative to undesired molecules in a population following the selection step. As indicated herein, a selection step may be repeated any number of times, and different types of selection steps may be combined in a given approach.

The term "pause sequence" refers to a nucleic acid sequence that causes a ribosome to slow or stop its rate of translation.

The term "solid support" refers to, without limitation, any column (or column material), bead, test tube, microtiter dish, solid particle (for example, agarose or sepharose), microchip (for example, silicon, silicon-glass, or gold chip), or membrane (for example, the membrane of a liposome or vesicle) to which an affinity complex may be bound, either directly or indirectly (for example, through other binding partner intermediates such as other antibodies or Protein A), or in which an affinity complex may be embedded (for example, through a receptor or channel).

The term "linker region" refers to a region of nucleic acid connecting the nucleic acid sequences encoding the antibody VH and VL domains in a scFv antibody gene. A linker region is in-frame with the nucleic acid sequences encoding the antibody VH and VL such that a continuous open reading frame containing the VH, VL and linker regions is formed. The term also refers to the region connecting the VH and VL in an scFv protein.

The term "peptide acceptor" refers to any molecule capable of being added to the C-terminus of a growing protein chain by the catalytic activity of a ribosomal peptidyl transferase. Typically, such molecules contain (i) a nucleotide or nucleotide-like moiety (for example, puromycin and analogues thereof)), (ii) an amino acid or amino acid-like moiety (for example, any of the 20 D- or L-amino acids or any amino acid analog thereof (for example, O-methyl tyrosine or any of the analogs described by Ellman et al. (1991) Meth. Enzymol. 202:301), and (iii) a linkage between the two (for example, an ester, amide, or ketone linkage at the 3' position or, less preferably, the 2' position); preferably, this linkage does not significantly perturb the structure of the ring from the natural ribonucleotide conformation. In addition, this term encompasses, without limitation, a peptide acceptor molecule that is covalently bonded (either directly or indirectly through intervening nucleic acid sequence) to the protein coding sequence, as well as one that is joined to the protein coding sequence by some non-covalent means, for example, through hybridization using a second nucleic acid sequence that binds at or near the 3' end of the protein coding sequence and that itself is bound to a peptide acceptor molecule.

II. Overview

The present invention features improved in vitro RNA display libraries to allow reliable expression and selection of scFv antibody molecules from expression libraries. RNA display methods generally involve expression of a library of proteins or peptides, wherein the expressed proteins or peptides are linked covalently or by tight non-covalent interaction to their encoding mRNA to form RNA/protein fusion molecules. The protein or peptide component of an RNA/protein fusion is selected for binding to a desired target and the identity of the protein or peptide determined by sequencing of the attached encoding mRNA component.

The scFv antibody libraries of the invention contain an optimized, shortened inter-domain linker that improves expression scFv antibody expression. The scFv antibody libraries also include short nucleic acid barcodes that allow for identification of individual library clones, libraries or subsets thereof.

The present invention also provides novel primers for generating, amplifying and spectratyping the scFv antibody libraries of the invention.

III. Library Construction

As an antibody technology development to generate monoclonal antibody drug candidates, this invention discloses the development of two recombinant antibody generation approaches, PROfusion (mRNA display) and Yeast Surface Display. The PROfusion mRNA display technology is an ab initio method for screening human antibody libraries. The yeast surface display technology is a cellular method for screening monoclonal antibodies specifically displayed on the yeast surface.

In one aspect, the invention features novel antibody libraries capable of expressing antibody molecules. Libraries of the invention are generated from any antibody fragment capable of binding to a target. In one embodiment, libraries of antibody variable domains are generated. In an embodiment, these are VH and/or VL domains. In another embodiment, scFv libraries are generated.

The libraries of the invention may also include antibody nucleic acid sequences encoding regions outside of the variable regions, for example, a constant region or fragment thereof, or a hinge region.

Nucleic acid libraries of the invention can comprise RNA, DNA, or both RNA and DNA elements.

1) Generation of Nucleic Acid Input Diversity

The nucleic acid sequences used to generate the antibody libraries of the invention may be obtained from any source. In one embodiment, the libraries of the invention may be obtained from the antibody repertoire of any animal including, but not limited to, rodents, primates, camelids, sharks, or any transgenic animal containing a repertoire of human immunoglobulin genes. Techniques for the isolation and cloning of nucleic acids encoding the variable regions of the antibody complement of an organism are well known in the art. Indeed, many cDNA libraries containing nucleic acids encoding the variable regions of antibodies are commercially available, for example, libraries of human antibody variable regions generated from various immune cells, for example, peripheral blood mononuclear cells (PBMC), spleen or lymph node. In another embodiment, the libraries of the invention may be obtained by ab initio synthesis of nucleic acids encoding one more antibodies.

The libraries of the invention may require the introduction of additional diversity by introducing nucleic substitutions and/or deletions that result in one or more amino acid substitutions and/or deletions in the expressed antibodies molecules. Any art recognized methods of mutagenesis are contemplated, for example, random mutagenesis, "walk through mutagenesis, and "look through mutagenesis. Such mutagenesis of an antibody may be achieved by using, for example, error-prone PCR, "mutator" strains of yeast or bacteria, or incorporation of random or defined nucleic acid changes during ab inito synthesis of all or part of an antibody. In one embodiment, a library of antibody molecules may be created in which one or more amino acids are randomly mutated. In another embodiment, a library of antibody molecules may be created in which one or more amino acids are mutated to one or more predetermined amino acid.

2) Control Sequences

The nucleic acid libraries of the invention may contain additional control sequences to facilitate the expression and screening of the encoded antibodies in vitro.

One such control sequence may be a promoter to be used in conjunction with a desired RNA polymerase for mRNA synthesis. As described herein, any promoter capable of directing synthesis from a linear double-stranded DNA may be used, for example, the T7, SP6 or T3 phage promoters.

A second control sequence may be termed the 5' untranslated region (or 5'UTR) and corresponds to the RNA upstream of the translation start site. Any other appropriate 5' UTR may be utilized (see, for example, Kozak (1983) Microbiol. Rev. 47:1). In one embodiment, the 5'UTR (termed "TE") may be a deletion mutant of the Tobacco Mosaic Virus 5' untranslated region and, in particular, corresponds to the bases directly 5' of the TMV translation start; the sequence of this UTR is as follows: rGrGrG rArCrA rArUrU rArCrU rArUrU rUrArC rArArU rUrArC rA (SEQ ID NO: 213) (with the first 3 G nucleotides being inserted to augment transcription).

A third element may be a translation start site. In general, this is an AUG codon. However, there are examples where codons other than AUG are utilized in naturally-occurring coding sequences, and these codons may also be used in the selection scheme of the invention. This translation start site is preferably in a suitable sequence context termed a "Kozak" sequence (see, for example, Kozak (1983) Microbiol. Rev. 47:1).

A fourth element may be a polyadenylation (poly A) sequence containing a 5' stop codon. The poly A sequence may be placed after the antibody coding sequence within the nucleic acid library construct. Such sequences are well known in the art and any such sequence is contemplated.

3) Additional Nucleic Acid Sequence Elements

The nucleic acid libraries of the invention may also include additional sequence elements that are incorporated into mRNA transcripts, encoding the antibodies. These may include non-antibody sequences.

In one embodiment, a short nucleic acid sequence, or "nucleic acid barcode", may be incorporated into the untranslated portion of an antibody mRNA transcript. These barcode sequences may serve as unique identifiers to distinguish individual members of a nucleic acid library or to distinguish between different libraries. The short nucleic acid sequences preferably contain less than 50 bases, less than 20 bases or less than 10 bases. In one embodiment, the short nucleic acid sequences comprise 8 bases.

In other embodiments, nucleic acid sequence elements encoding a specific non-antibody amino sequence may be incorporated into the open reading frame (ORF) of the nucleic acid libraries of the invention such that the encoded amino acid sequence is incorporated into the expressed antibody. In one embodiment, a non-antibody nucleic acid sequence element may be incorporated into the ORF of a scFv between the VH and VL regions to serve as a linker region. Any nucleic acid sequence that encodes a continuous amino acid sequence that lacks a stop codon may be contemplated for the linker region. The length of the linker region is less than 50 amino acids, or less than 20 amino acids, or less than 16 amino acids.

In another embodiment, nucleic acid sequence elements encoding one or more epitope tags (for example, a FLAG tag) may be incorporated into the antibody coding sequence.

These sequences may result in production of an antibody with an epitope tag present at any position, for example, at the N-terminus, at the C-terminus, or in the linker region between the VH and VL domains of an scFv antibody molecule. In one embodiment, sequences encoding an antibody constant region or fragment thereof may be included in the 3' portion of the ORF of the nucleic acid libraries of the invention. This antibody constant region or fragment thereof is identical in all members of a particular library.

In other embodiments, nucleic acid sequence elements encoding a specific non-antibody amino sequence may be incorporated into the vectors, which are utilized to specifically express the nucleic acid library in this invention on the surface of yeast cells. These elements may include, but are not limited to, transmembrane domains known in the art. In one embodiment, these elements may be incorporated into the ORF of the nucleic acid libraries of the invention such that the encoded amino acid sequence is incorporated into the expressed antibody. In another embodiment, these elements may be incorporated into the vector sequence but not the ORF of the nucleic acid libraries of the invention. These elements may help the expression, stability, folding and epitope presentation, or other characteristics of the nucleic acid library in this invention and mentioned above.

4) Oligonucleotide Primers

In one aspect, the invention features nucleic oligonucleotide primers suitable for the synthesis and/or amplification of the antibody libraries of the invention. Exemplary primers include SEQ ID NOs: 1-13 (Table 6).

In another aspect the invention features nucleic oligonucleotide primers suitable for reverse transcription of mRNA produced from the libraries of the invention (Table 3). Exemplary primers include SEQ ID NOs: 14-16 (Table 3).

In another aspect the invention features oligonucleotide primers suitable for spectratype PCR analyzes of VH CDR3 size distributions in the library or its selection outputs (Table 4). Spectratyping may be a useful tool for assessing antibody library diversity and the progression of selections. Exemplary spectratyping PCR primers include SEQ ID NOs: 17-18.

5) Linkage of Nucleic Acid to Peptide Acceptors

In an embodiment, the antibody nucleic acid libraries of the invention may be modified to contain a peptide acceptor moiety. This facilitates the covalent attachment of individual member of nucleic acid expression libraries to their cognate protein products. Any art recognized means of attachment of a peptide acceptor to a nucleic acid are contemplated.

In one aspect, the invention features novel methods and compositions for the attachment of a peptide acceptor to nucleic acid libraries. In one embodiment, a linking molecule may be synthesized that comprises a Psoralen C6 molecule and a peptide acceptor molecule, wherein the Psoralen C6 molecule and a peptide acceptor molecule may be fused to a nucleic acid sequence, wherein the nucleic acid sequence may be complementary to sequences at the 3' end of the nucleic acid library. Such linking molecules may bind, via complementary base pairing, to the 3' end of nucleic acid library clones. Psoralen C6 is sensitive to ultraviolet (UV) light and will cross link the linker to the nucleic acid library clones, thus covalently linking the peptide acceptor to the nucleic acid library clones. In another embodiment, the nucleic acid portion of the linker molecule may contain modified nucleotides, for example, 2 prime methoxy (2'OMe) ribonucleotides. In another embodiment, the linker molecule may further comprise a Triethylene glycol or PEG-150 linker separating the nucleic acid region containing the Psoralen C6 molecule and a peptide acceptor molecule. In one embodiment the linker may be: 5' (Psoralen C6) 2'OMe(U AGC GGA UGC) (SEQ ID NO: 211) XXX XXX CC (Puromycin) 3', (where X is a Triethylene glycol or PEG-150 and CC is standard DNA backbone). In an embodiment, such linkers are custom-synthesized by, for example, TriLink BioTechnologies, Inc (San Diego, Calif.).

IV. Methods of Spectratyping

Spectratype analysis is a method used in clinical and basic immunological settings in which antigen receptor length diversity is assessed as a surrogate for functional diversity (see, for example, Cochet, M., et al. (1992) *Eur. J. Immunol.*, 22:2639-2647; Pannetier, C., et al. (1993) *Proc. Natl Acad. Sci. USA*, 90:4319-4323; Pannetier, C., et al. (1997) In Austin, O. J. R. (Ed.). *The Antigen T Cell Receptor: Selected Protocols and Applications*, TX Landes, pp. 287-325). Spectratype assays may use, for example, CD4 or CD8 T cells isolated from a peripheral blood sample from the subject, while in other cases total CD3 or PBMC cells are used.

In this invention, PCR may be used to specifically replicate the variable-length region (CDR3) for analysis of genetic sequences encoding antibodies on the basis of CDR3 length. Changes in CDR3 length distribution are correlated with changes in the antibody repertoire. In some embodiments, primers specific to individual libraries constructed in the practice of the invention may be used to provide independent spectratypes for each library. In one preferred embodiment, a fluorescent dye-labeled 5' forward primer (6-FAM-PanVHFR3-Fwd, 5'-GACACGGCCGTGTATTACTGT-3', SEQ ID NO: 17) and a reverse primer (PanJH-Rev, 5'-GCTGAGGAGACGGTGACC-3', SEQ ID NO: 18) that respectively anneal to the VH's framework 3 region and to the J region may be used to amplify across the CDR3 regions of VH domains by PCR. In other embodiments, other primers known in the art may be used, with specifically annealing to the same region or other regions on the polynucleotide sequences encoding the library of antibodies. In one preferred embodiment, the resulting mixture of CDR3 replicons may be size-separated by electrophoresis, and quantified by densitometry. In other embodiments, other methods known in the art may be used to characterize the resulting CDR3 replicons.

In one preferred embodiment, spectratyping analysis of CDR3 size distribution among different VH families may be carried out on VH cDNA fragments. In an embodiment, the exemplary VH families may be obtained from a single germline or from different VH families such as VH1-46, VH2, VH5, and VH6. In one preferred embodiment, the templates for spectratyping may be selected from human lymph node libraries, yeast spleen libraries, naïve human lamda libraries, human PBMC kappa libraries, VH-Vλ, scFv library, VH-Vκ scFv library, for example. In other embodiments, the templates for spectratyping may be selected from other libraries.

V. General Screening Methods

In one aspect, the invention features methods of screening the expression libraries of the invention to identify antibodies capable of binding to a desired target. Any in vitro or in vivo screening method that allows for selection of an antibody from an expression library, based upon the antibody binding to a target molecule, is contemplated.

In one embodiment, the expression libraries of the invention may be screened using an art recognized in vitro cell-free phenotype-genotype linked display. Such methods are well known in the art and are described, for example, in U.S. Pat. Nos. 7,195,880; 6,951,725; 7,078,197; 7,022,479; 6,518,018; 7,125,669; 6,846,655; 6,281,344; 6,207,446; 6,214,553;

6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315. These methods involve transcription of protein in vitro from a nucleic acid in such a way that the protein is physically associated or bound to the nucleic acid from which it originated. By selecting for an expressed protein with a target molecule, the nucleic acid that codes for the protein may also be selected.

To improve the expression of scFv proteins, the above referenced in vitro screening assays may require the addition or removal of certain reagents. In one embodiment, protein disulphide isomerase enzymes may be added to the in vitro expression system to improve the production of functional scFv molecules. In another embodiment, a mild oxidizing agent (for example, GSSG (oxidized glutathione)/GSH (reduced glutathione), for example 100 mM GSSG/10 mM GSH) may be added to in vitro translation reaction mixture of the scFv proteins to allow intra-chain disulphide bond formation in the VH and VL regions of the scFv molecule. In another embodiment, reducing agents (for example, dithiothreitol (DTT)) may be removed from the in vitro translation reaction mixture of the scFv.

In another embodiment, one or more labeled amino acids, or derivatives thereof, may be added to the in vitro translation system such that the labeled amino acid(s) becomes incorporated into the resultant antibody. Any art recognized labeled amino acid is contemplated, for example, a radiolabelled amino acid, for example, $^{35}$S-labelled methionine or cysteine.

In one embodiment, the in vitro screening assays of the invention require that after in vitro selection of an antibody or plurality of antibodies the mRNA that is physically associated with the antibody or plurality of antibodies may be reverse transcribed to generate cDNA encoding said antibody or plurality of antibodies. Any suitable method for reverse transcription is contemplated, for example, enzyme mediated, for example, Moloney murine leukemia virus reverse transcriptase.

The screening methods employed in the invention may require amplification of the nucleic acid that encodes antibodies that bind specifically to a desired target. In one embodiment, mRNA that is physically associated with an antibody or plurality of antibodies may be amplified to produce more mRNA. Any art recognized method of RNA replication is contemplated, for example, using an RNA replicase enzyme. In another embodiment, mRNA that is physically associated with an antibody or plurality of antibodies is first reverse transcribed into cDNA before being amplified by PCR. In one embodiment, PCR amplification is accomplished using a high fidelity, proof—reading polymerase, for example, the KOD1 thermostable DNA polymerase from *Thermococcus kodakaraensis* or Platinum Taq DNA Polymerase High Fidelity (Invitrogen, Carlsbad, Calif.). In another embodiment, PCR amplification may be performed under conditions that result in the introduction of mutations into amplified DNA, i.e., error-prone PCR.

Screening methods employed in the invention may also require that the stringency of the target-binding screening assay be increased to select for antibodies with improved affinity for target. Any art recognized methods of increasing the stringency of an antibody-target interaction assay are contemplated. In one embodiment, one or more of the assay conditions may be varied (for example, the salt concentration of the assay buffer) to reduce the affinity of the antibody molecules for the desired target. In another embodiment, the length of time permitted for the antibodies to bind to the desired target may be reduced. In another embodiment, a competitive binding step may be added to the antibody-target interaction assay. For example, the antibodies may first be allowed to bind to a desired immobilized target. A specific concentration of non-immobilized target may then be added, which serves to compete for binding with the immobilized target such that antibodies with the lowest affinity for antigen are eluted from the immobilized target, resulting in an enrichment for antibodies with improved antigen binding affinity. In an embodiment, the stringency of the assay conditions may further be increased by increasing the concentration of non-immobilized target that is added to the assay.

Screening methods of the invention may also require multiple rounds of selection to enrich for one or more antibodies with improved target binding. In one embodiment, at each round of selection further amino acid mutations may be introduced into the antibodies using art recognized methods. In another embodiment, at each round of selection the stringency of binding to the desired target may be increased to select for antibodies with increased affinity for a desired target.

Screening methods of the invention may require purification of RNA-antibody fusion proteins from the components of an in vitro translation system. This may be accomplished using any art recognized method of separation. In one embodiment, the RNA-antibody fusion proteins may be separated by chromatography using a polydeoxythimidine (polydT) resin. In another embodiment, the RNA-antibody fusion proteins may be separated by chromatography using an antibody specific for an epitope present in the antibody component of the RNA-antibody fusion protein. In an embodiment, the epitope may be an amino acid sequence tag, for example, FLAG or HA tags, incorporated into the amino acid sequence of the antibody component of the RNA-antibody fusion protein, for example, at the N-terminal, C-terminal or in the inter variable region linker.

Selection of antibodies from the libraries of the invention may require the use of immobilized target molecules. In one embodiment, the target molecule may be directly linked to a solid substrate for example, agarose beads. In another embodiment, the target molecule may first be modified, for example, biotinylated and the modified target molecule may be bound via the modification to a solid support, for example, streptavidin-M280, neutravidin-M280, SA-M270, NA-M270, SA-MyOne, NA-MyOne, SA-agarose, and NA-agarose.

This invention is further illustrated by the following examples that should not be construed as limiting.

EXEMPLIFICATION OF THE INVENTION

Throughout the examples, the following materials and methods were used unless otherwise stated.

Materials and Methods

In general, the practice of the present invention employs, unless otherwise indicated, conventional techniques of chemistry, molecular biology, recombinant DNA technology, immunology (especially, e.g., immunoglobulin technology), and animal husbandry. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); Current Protocols in Molecular Biology, eds. Ausubel et al., John Wiley & Sons (1992).

Figure 2:
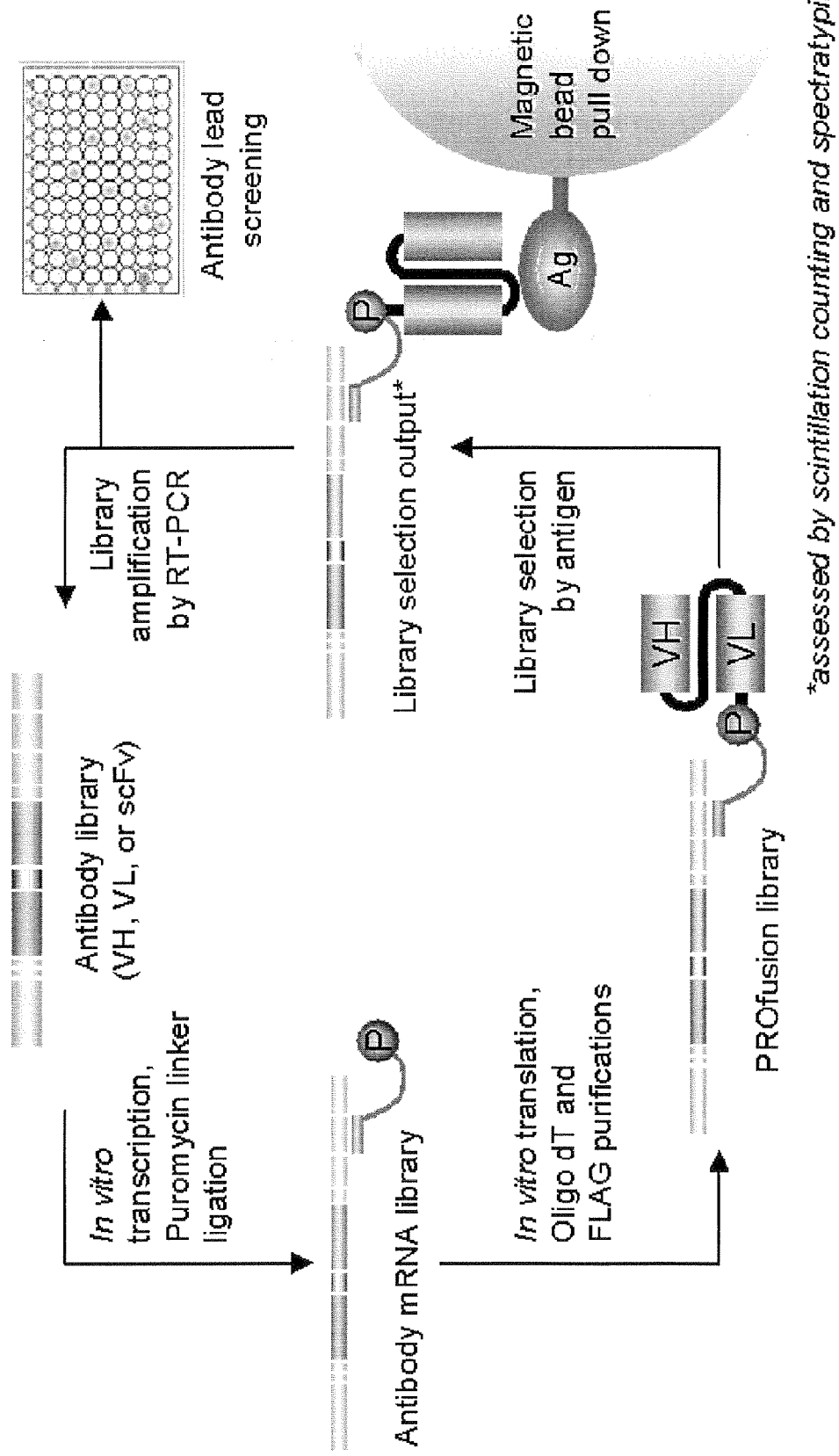
FIG. 2 depicts a general scheme for the mRNA-scFv display technology in certain embodiments of the invention.

Example 1 mRNA Display Protocol for ScFv Molecules mRNA display may be conducted according to the method shown in FIG. 2. The particular embodiments of this method are described in greater detail below. These embodiments are intended to illustrate the methods of the invention, and should not be construed as limiting.

1. Design of Antibody Library Templates

Figure 3:
FIG. 3 depicts a general depiction of a library DNA construct.

Library DNA constructs are designed according to the diagram depicted in FIG. 3. The double-stranded DNA constructs generally contain the following functional elements, from the 5' to the 3'end. A T7 promoter may be useful for the RNA transcription in vitro. A TMV-UTR (tobacco mosaic virus untranslated region) may be useful for protein translation in vitro. An optional tag contains an 8 base-pair sequence unique to each library, which may be useful for identifying constructs belonging to a given library. A Kozak consensus sequence facilitates the initiation of protein translation. The antibody library of interest may contain sequences encoding an scFv, VH, or VL. In a preferred embodiment, the antibody library encodes scFv. In one embodiment, a partial antibody constant region sequence that is invariable at the 3' end of all antibody libraries is also included. In some embodiments, constructs additionally include a FLAG tag useful for affinity purification. In other embodiments, constructs contain a linker annealing sequence comprising of an annealing site, where a psoralen and puromycin modified DNA oligonucleotide linker may be crosslinked to the construct in subsequent steps of the protocol. In an embodiment, a polyadenylation sequence with a 5' stop codon may be useful for mRNA stability and purification through oligo-dT cellulose batch purification.

2. Preparation of the Target Antigen

Generally the mRNA display antibody library may be selected against biotinylated antigens. While the best antigen for each target should be determined on a case-by-case basis, the following considerations may be used as a general guideline. A target antigen is typically well characterized, and is the relevant or dominant genetic isotype, as determined by polymorphism (SNP and haplotype) and/or pharmacogenetic analysis. A target antigen additionally may have reasonable bioactivity (comparable to the native antigen), good solubility and good chemical and physical properties, and may be prepared in sufficient quantities for library selections or screenings and downstream bioassays. Exemplary quantities of target antigen useful for library selection are noted in Table 1 below.

TABLE 1

Target antigen quantity required for library selection

| Technology | Choice of human antibody scFv libraries | Antigen requirements (to be multiplied by # of libraries) | | | Deliverables |
| | | for each library selection | for each library output screening | Contingent antigen requirement | |
|---|---|---|---|---|---|
| PROfusion mRNA Display | 2 PBMC (κ/λ) 2 Spleen (κ/λ) 2 Lymph nodes (κ/λ) | 1 nmole biotinylated | 2.5 nmole biotinylated | 2 nmole biotinylated | Bioactive IgG candidates that will likely need LO |
| Yeast Display | 2 PBMC (κ/λ) 1 Spleen (κ) 1 Lymph nodes (κ) | 6.5 nmole (preferably biotinylated) | 3 nmole biotinylated | 3 nmole biotinylated | |

3. Preparation of the Library DNA

The library DNA and its selection outputs may be amplified by PCR. Exemplary primers for library amplification are shown in Table 2.

TABLE 2

Primers for library amplification

| Primer | Amplifies | Sequence |
|---|---|---|
| *5' forward primer* | | |
| T7TMVUTR (SEQ ID NO: 1) | All scFv and VH libraries | TAATACGACTCACTATAGGGACAATT ACTATTTACAATTACA |
| VL-T7TMVTag3GS-Fwd$^a$ (SEQ ID NO: 2) | Vκ and Vλ PBMC libraries | TAATACGACTCACTATAGGGACAATT ACTATTTACAATTACAGGCTTTGGACC ATGGGGTCTGGCGGCGGAGGTAGCG |
| *3' reverse primer* | | |
| CK5FLAGA20 Rev (SEQ ID NO: 7) | All κ scFv and Vκ libraries | TTTTTTTTTTTTTTTTTTTTAAATAGCG GATGCCTTGTCGTCGTCGTCCTTGTAG TCGAAGACAGATGGTGCAGCCACA |

TABLE 2-continued

Primers for library amplification

| Primer | Amplifies | Sequence |
|---|---|---|
| CL5FLAGA20 Rev (SEQ ID NO: 12) | All λ scFv and Vλ libraries | TTTTTTTTTTTTTTTTTTTAAATAGCG GATGCCTTGTCGTCGTCGTCCTTGTAG TCAGTGACAGTGGGGTTGGCCTTG |
| VH-GSFLAGA20-Rev$^a$ (SEQ ID NO: 13) | VH library from human PBMC | TTTTTTTTTTTTTTTTTTTAAATAGCG GATGCTTTGTCATCATCATCTTTATAA TCGCTACCTCCGCCGCCAGAC |

PCR amplification may be performed using methods known in the art. PCR reactions typically contain the DNA template, a reaction buffer, dNTP, the primers used for amplification, DNA polymerase, and water. Multiple reaction tubes are set up simultaneously from a master mix to increased amplified DNA yield. 25 cycles of PCR typically give sufficient amplification, but as many as 35 cycles may be used to gain more products.

4. Library DNA Purification

If products from the above PCR are the correct size (~850 bp for scFv, ~500 bp for VH or VL library) and contain minimal non-specific products, they may be used directly in the transcription reaction. Alternatively, the products may be gel purified. If gel purification is performed for PCR products, the products may be separated on a preparative agarose gel and the specific band containing the PCR products may be cut out. DNA may then be purified from the band by gel extraction, using standard methods known in the art, and its concentration measured on a spectrophotometer.

5. RNA Transcription

The RNA transcription from library DNA may be performed using standard methods known in the art. A large reaction volume may be used to transcribe sufficient DNA templates to sample the entire library diversity. In an exemplary embodiment, $1 \times 10^{13}$ copies of library templates may be used in the RNA transcription reaction. An RNA transcription reaction typically contains 5-10 μg of PCR product, a reaction buffer, plus ATP, CTP, GTP, UTP, and T7 RNA polymerase. The RNA transcription reaction may be run at 37° C. for between 2 hours to overnight. Shorter times may be used following initial rounds of selection. After the RNA transcription, DNA templates may be removed from the reaction mixture using DNase I.

6. RNA Purification by NAP Column Chromatography

Following the RNA transcription, RNA may be fractionated using a NAP-10 column (GE Healthcare, Piscataway, N.J.). Up to 1 mL of transcription reaction may be loaded onto a NAP-10 column for RNA purification. The column may be equilibrated using diethylpyrocarbonate (DEPC)-treated dH$_2$O prior to fractionation. The total elution volume should be less than 150% of the transcription reaction volume. RNA may be additionally or alternatively fractionated using a NAP-25 column (GE Healthcare, Piscataway, N.J.).

7. RNA Quality Control and Quantitation

The size and yield of RNA samples may be monitored using gel electrophoresis. The RNA yield typically reaches a maximum at ±20 nmol/mL transcription reaction.

8. RNA Ligation to Linker

A DNA linker that contains a peptide acceptor molecule at its 3' end may be covalently ligated to the 3' ends of each RNA molecule. The peptide acceptor, which can enter the ribosomal A site and covalently couple to the carboxyl terminus of the nascent polypeptide chain, will ultimately enable the covalent association of the mRNA (genotype) to the protein encoded by this mRNA (phenotype). An exemplary PEG6/10 linker may have the following formula:

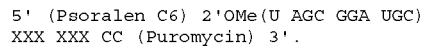

5' (Psoralen C6) 2'OMe(U AGC GGA UGC) XXX XXX CC (Puromycin) 3'.

The Psoralen C6 5' modification is light sensitive and functions to create a covalent bond between the linker and the mRNA by UV crosslinking. A 2'OMe (U AGC GGA UGC) (SEQ ID NO: 211) backbone region anneals to the linker annealing site 3' to the FLAG sequence on mRNA (see FIG. 1). In the sequence above, X denotes "Spacer 9", alternatively known as Triethylene glycol or PEG-150. This spacer has been optimized to provide flexibility for puromycin insertion into the eukaryotic ribosome A site. CC comprises a standard DNA backbone. A puromycin 3' modification inserts into the ribosome A site to create a stable link between the linker and the nascent peptide. The extinction coefficient for the linker described herein is 147.7 OD$_{260}$/μmole. Since this linker is light sensitive, solutions containing this linker should be protected from light.

For initial rounds of library selections, a large-scale ligation reaction ($3.1 \times 10^{15}$ transcribed RNA molecules) is recommended to sample a library's entire diversity. This RNA quantity may be set to ensure enough templates are put into translation reactions and produce ~10 μmol functional mRNA display molecules. In later rounds, RNA input may be reduced to 0.5 nmol per selection. In an exemplary embodiment, an RNA ligation reaction may contain the following components: the RNA, water, a chemical ligation buffer, and the PEG6/puromycin linker (1 mM). In an exemplary embodiment, the total reaction volume is 100 μL. In a preferred embodiment, the linker/RNA molar ratio may be greater than 1.5. In one embodiment, the final linker concentration in the reaction may be about 15 μM, and the RNA concentration in the reaction may range from about 3-10 μM (=0.3-1 nmol RNA input). As a reference, an 850 nt scFv RNA at 1 mg/mL=3.56 μM, and the attainable maximal ligation concentration is 3.16 μM (=0.32 nmol).

The annealing reaction (which anneals the linker to the transcribed RNA) may be performed in a thermal cycler. In a preferred embodiment, the annealing reaction may be conducted by incubating samples at about 85° C. for 30 seconds, then at about 4° C., using a ramp rate of about 0.3° C. per second. Reactions may then be held at 4° C.

Ligation of the annealed linker/RNA may be accomplished by UV crosslinking. This may be conducted using any method known to one of skill in the art. In one embodiment, reaction tubes may be placed over the center of a handheld UV lamp (long wavelength, about 365 nm) and crosslinked for about 15 minutes. A freezer pack may be placed on top of the lamp to help dissipate heat generated during UV irradiation. Typical ligation efficiency is about 50-90%, and purification is usually not required. The ligation products may be stored at −80° C.

9. Translation Reaction

In an exemplary embodiment, about ~0.1% of input RNA may be made into mRNA display molecules after all reactions and purifications. In vitro translation may be conducted using methods and reagents known to one of skill in the art. In one embodiment, the translation reaction using the scFv library may use about 5 nmol of RNA template with about 10 mL of reticulocyte lysate in a reaction volume of about 15 mL.

In preparation for the translation reaction, solutions of GSSG/GSH (oxidized glutathione/reduced glutathione) may be prepared at a final concentration of about 100 mM GSSG/10 mM GSH. PDI (Protein Disulfide Isomerase) may be prepared by dissolving PDI powder into $dH_2O$ to reach a concentration of about 1 Unit/μL. The PDI solution may be stored at −20° C.

An exemplary translation reaction may be set up as follows:

| RNA (100 pmol) | X | X μL |
|---|---|---|
| $dH_2O$ | to 73.7 | to 370 μL |
| Amino acid master mix (Met) | 15 | 75 μL |
| 100 mM GSSG/10 mM GSH | 3.3 | 16.5 μL |
| PDI (1 U/μL) | 6 | 30 μL |
| [$^{35}$S]Methionine | 2 | 10 μL |
| Reticulocyte lysate | 200 | 1000 μL |
| Total volume | 300 | 1500 μL |

Translation reactions are incubated in 30° C. water bath for 1-2 hours. A significant decrease in RNA/protein fusion yield was observed when the translation volume exceeds 1.5 mL. Therefore a master mix of the translation reaction may be prepared if the reaction volume will be larger than 1.5 mL, before dividing it to smaller aliquots.

10. RNA/Protein Fusion Formation

After the translation reaction, about 100 μL 2M KCl and about 20 μL 1M $MgCl_2$ may be added for every 300 μL of translation reaction mixture, and incubated for 1 hour at room temperature. This stabilizes the paused ribosomes at the end of mRNA templates and allows puromycin at the end of the DNA linker to enter the A sites of paused ribosomes, which permanently links the translated scFv proteins to their mRNA templates. The room temperature incubation may be shortened if the reaction will be stored at −20° C. overnight. The reaction may be terminated by adding 50 μL 0.5 M EDTA to disrupt the ribosomes. Reactions may be stored at −20° C. A 5 μL aliquot may be removed for scintillation counting later.

11. RNA/Protein Fusion Purification by Oligo-dT Cellulose

This step purifies mRNA display molecules and remaining RNA templates from the translation/fusion reaction. For oligo-dT binding, the amount of pre-washed oligo-dT cellulose needed to capture all RNA templates may be estimated. A sufficient volume of oligo-dT binding buffer may be added to the fusion reaction to reach about a 1× final concentration. Pre-washed oligo-dT cellulose may then be added, and the reactions carried out for 1 hour at 4° C. Reactions may optionally be spun down at about 1500 rpm for 5 minutes at 4° C., and the supernatant discarded. Oligo-dT cellulose beads may be transferred and washed about 6 times with 1× Oligo-dT binding buffer using spin columns, and the buffer may typically be removed by spinning columns at about 1000 rpm for 10 seconds. The flow-through may be discarded, but the last wash may be saved for scintillation counting. mRNA display molecules (and free RNA templates) may be eluted by adding $dH_2O$ to beads and incubating for 5 minutes at room temperature. The eluate may be collected by spinning at about 4000 rpm for 20 seconds. The elution may typically be repeated once, and the eluates combined. 5 μL of eluate may be removed for scintillation counting. The efficiency of oligo-dT purification may also be assessed by OD at 260 nm ($OD_{260}$) on a NanoDrop spectrophotometer machine (NanoDrop Technologies, Wilmington, Del.). All remaining RNA templates and mRNA display molecules are theoretically recovered by the oligo-dT beads. 5× FLAG binding buffer may be added to the eluates to reach about a 1× final concentration. Samples may be stored at −80° C. if not proceeding to the next FLAG purification step.

Oligo-dT recovery may be calculated as follows. About 5 μL of input (from fusion reaction), 100 μL from the last wash, and 5 μL of output (eluate from oligo-dT purification) are counted. The last wash is used to assess extent of washing, and the other two counts are used to calculate RNA/protein fusion recovery from original RNA template input. RNA/protein fusion yield (pmol)=($CPM_{output}$×$Volume_{output}$×5 μM×$Volume_{lysate}$) [$CPM_{input}$×$Volume_{input}$×(# of methionine in product)]. This formula assumes a 5 μM methionine concentration in the reticulocyte lysate, and all volumes used in calculation expressed as μL. For earlier rounds of selection the yield of mRNA display molecules is typically 0.5-2%, but may increase to 10% in later rounds.

12. RNA/Protein Fusion Purification by anti-FLAG M2 Agarose

This step purifies mRNA display molecules from remaining RNA templates. The amount of pre-washed anti-FLAG M2 agarose beads needed to capture all mRNA display molecules may be estimated. In one embodiment, the binding capacity of the beads is about 6 nmol fusion protein per mL of 50% slurry. To have a sufficient bead volume for manipulation during binding and washing, it is not recommended to use less than 200 μL of pre-washed beads. The example given below is for an initial 300 μL translation reaction.

For FLAG purification, a wide-bore pipette tip may be used to transfer 300 μL pre-washed anti-FLAG M2 agarose to the oligo-dT purified output. The mixture may be mixed and incubated by rotation for 1 hour at 4° C. Incubation with anti-FLAG M2 agarose may continue overnight. Anti-FLAG M2 agarose may optionally be spun at about 1500 rpm in a centrifuge for 1 minute at 4° C., and the supernatant may be discarded. Anti-FLAG beads may be washed about 5 times with 1× FLAG binding buffer, using spin columns and centrifugation at about 1000 rpm for 10 seconds for each wash. The flow-through may be discarded. The beads may additionally be washed 2 times with 700 μL selection buffer (see below) by centrifugation at about 1000 rpm for 10 seconds. The last wash may be saved for scintillation counting. mRNA display molecules may be eluted by adding about 400 μL 100 μg/mL FLAG peptide (in selection buffer) and incubating for 5 minutes at room temperature. The eluate may be collected by spinning at about 3000 rpm for 20 seconds and eluted one more time by adding about 400 μL 100 μg/mL FLAG peptide. Both elutes may be combined, and 5 μL of the combined elutes may be removed for scintillation counting. This volume of FLAG peptide is typically sufficient for elution from up to about 1 mL of 50% slurry, and may be cut in half (200 μL) if less slurry was used and/or higher RNA/protein fusion concentration is desired. To prevent RNA degradation during storage and antigen selection, an appropriate amount of RNase inhibitor known in the art (i.e., 1-2 U/μL RNaseOUT and 0.02 μg/mL yeast tRNA) may be added to the purified mRNA display library. Samples are stored at −80° C. if not proceeding to the next antigen selection step.

To quantitate the FLAG recovery, about 5 μL elution output and about 100 μL from the last wash may be counted on a beta counter. A recovery of 10-30% or higher may be expected, and may be calculated according to the following formula:

$$\text{PROfusion molecule recovery \%} = (CPM_{output} \times \text{Volume}_{output}) / (CPM_{input} \times \text{Volume}_{input}).$$

13. Library Selection by Biotinylated antigens

Selection is designed to enrich molecules that specifically bind to a target of interest. A negative selection (pre-clear) may be necessary to remove non-specific and matrix binders. Depending on the target format, the selection protocol varies. The following is an exemplary selection protocol for use with biotinylated targets. This protocol may be modified to accommodate target antigens in other formats, and may be scaled up or down depending on the desired output.

A. Preparations Before Selection

Streptavidin (SA) magnetic beads may be used for capture, and are typically pre-blocked prior to use. SA beads may be transferred from the original bottle to 1.5 or 2 mL tubes, and washed twice with 2 mL of 1× FLAG binding buffer. The beads may then be blocked with 2 mL of the selection buffer for 2 hours to overnight at 4° C. with rotation. Enough beads should be prepared for both pre-clear and selection capture. Pre-blocked beads are stored at 4° C. About 100 μL of beads are typically used for every 10 μmol of biotinylated antigen.

1.5 mL or 2 mL microfuge tubes are pre-blocked with 1× FLAG binding buffer for about 1 hour to overnight. The pre-blocked tubes may be used for all pre-clear and selection steps. Typically four tubes are needed for each sample: 2 for pre-clearing, 1 for the beads, and 1 for selection.

Optimal results may be obtained by pre-clearing the library. FLAG-purified mRNA display library may be added to the SA beads (separated from buffer). The volume of SA bead may be equal to half of the capture volume. The total mixture may be incubated with rotation at 30° C. for 30 minutes before the separation of pre-cleared mRNA display library from SA beads using a magnet. This pre-clearing step is repeated one more time and the second pre-clear SA beads may be washed and counted as described in above to determine if background is high. This may also serve as a "no antigen" negative control.

B. Library Selection: Binding

For first rounds of selection, biotinylated target may be added (100 nM) to the whole pre-cleared library and incubated with rotation at 30° C. for 1 hour. For later selection rounds when recovery of antigen-binding molecules is expected to exceed 1%, the pre-cleared library may be divided into 2 equal aliquots. Biotinylated antigen may be added to one aliquot, and the other serves as the "No antigen" negative control. Alternatively, the washed second pre-clear beads may also be considered as a "No antigen" control, as noted above, although these beads will have one less 'pre-clearing' procedure. The antigen concentration in later rounds may be dropped when recovery of antigen-binding molecules exceeds 5%.

C. Library Selection: Capture

Pre-blocked SA beads (separated from buffer) may be added to the binding reaction and incubated with rotation at 30° C. for 5 to 10 minutes. The amount of SA beads for capture should be calculated based on the capacity and the target concentration used in selection (see above). The amount of SA beads should be reduced when lowering the target concentration to avoid the SA bead binders, but typically not less than 50 μL of beads is used.

D. Library Selection: Washing

The SA beads may be collected using a magnet and may be washed with 1 mL of the selection buffer for 1 minute. The beads are collected again using a magnet and washed for about 5 more times (about 6 times total). The wash time may be increased in later rounds to incorporate off rate selection strategy to some targets. The beads may be washed one last time with 1 mL of 1× buffer suitable for reverse transcription. The beads are collected with a magnet and re-suspended in water (one fourth of the capture bead volume calculated above).

E. Library Selection: Counting and Recovery Calculation

Starting from Round 3, about 10-20% of the last wash and the beads are counted. Typically only less than 100 μL of beads is counted, because more beads can quench the counts. Library selection recovery is calculated according to the following formula:

$$\text{Selection recovery \%} = 100 \times CPM_{Total\ Beads} / CPM_{Total\ Input}$$

14. Reamplification of Library DNA by RT-PCR

Reverse transcription may be performed using the material captured from the library. Reagents and protocols known in the art are suitable for performing the reverse transcription reaction. The volume of the reaction may be scaled up or down according to the bead volume after selection.

Exemplary primers useful for reverse transcription are shown in Table 3, although additional primers may be designed using methods known in the art. The Cκ reverse primer is used for kappa libraries, CJL reverse primer is used for lambda libraries, and Lib-GS-Rev is used for human PBMC VH library.

TABLE 3

| Exemplary primers suitable for reverse transcription | |
|---|---|
| Cκ Reverse (SEQ ID NO: 14) | GTCGTCGTCGTCCTTGTAGTCGAAGACAGATGGTG CAGCCACAGTTCG |
| CJL Reverse (SEQ ID NO: 15) | GTCGTCGTCGTCCTTGTAGTCAGTGACAGTGGGGT TGGCCTTGGGCTGACCKAGGACGGT |
| Lib-GS-Rev (VH, PBMC) (SEQ ID NO: 16) | CGCTACCTCCGCCGCCAGAC |

An exemplary reverse transcription reaction may contain the beads from the library selection (in water), about 10 μM reverse primer, and about 10 mM dNTP. Reactions are incubated at 65° C. for 5 minutes and chilled on ice. First strand synthesis buffer, 0.1M DTT, and RNase inhibitor are then typically added to the reaction. The reverse transcription reactions are incubated at 42° C. for 2 minutes before adding the reverse transcriptase enzyme. Reactions are then incubated at 42° C. for 50 minutes with occasional agitation and further incubated at 95° C. for 5 minutes. The beads are then collected by magnet, and the supernatant transferred to new tubes, which may be pooled if it is from same selection output. The beads are resuspended in water (half of RT volume), and incubated in tubes at 95° C. for 5 minutes. The beads are again collected using a magnet, and the supernatant is pooled with the previously transferred supernatant. This contains the cDNA template for PCR amplification of selection output.

Spectratyping PCR may be used to analyze VH CDR3 size distributions in the library or its selection outputs. It is a useful tool to assess the library diversity and the progression of selections. The initial few rounds of library selection outputs and the library before selection should be very diverse and the CDR3 size distribution approximates a Gaussian distribution. Exemplary spectratyping PCR primers are shown in Table 4.

TABLE 4

Exemplary spectratyping PCR primers

| | |
|---|---|
| 6-FAM-PanVHFR3-Fwd (SEQ ID NO: 17) | GACACGGCCGTGTATTACTGT |
| PanJH-Rev (SEQ ID NO: 18) | GCTGAGGAGACGGTGACC |

An exemplary spectratyping PCR reaction is shown below in Table 5, although the reaction components may be substituted with comparable reagents known in the art, and the reaction volume may be adjusted to accommodate the scale of the selection reaction.

TABLE 5

Exemplary spectratyping PCR reaction

| | |
|---|---|
| cDNA template | 2.0 μL |
| dH$_2$O | 18.1 μL |
| 5X thermal stable DNA polymerase reaction buffer | 6.0 μL |
| 25 mM MgCl$_2$ | 1.8 μL |
| 10 mM dNTP | 0.6 μL |
| 5' forward primer (10 μM) | 0.6 μL |
| 3' reverse primer (10 μM) | 0.6 μL |
| thermal stable DNA polymerase | 0.3 μL |
| Total volume | 30.0 μL |

Thermal stable DNA polymerases known in the art are suitable for this reaction. In an exemplary embodiment, the final Mg$^{2+}$ concentration is 1.5 mM. As an exemplary thermal cycling program, the reaction is incubated at 94° C. for 2 minutes and then subjected to 30 thermal cycles to elongate the DNA. For each cycle, the reaction is incubated at 94° C. for 20 seconds, at 55° C. for 20 seconds, and then at 72° C. for 30 seconds. After 30 cycles, the reaction is further incubated at 72° C. for 5 minutes and then stored at 4° C. After PCR, 10 μL of PCR product is loaded onto a 2% agarose gel to confirm that the reaction was successful. The reaction and the remaining product are analyzed by spectratyping electrophoresis.

The amplified DNA product has the following organization:

$$5'\text{-FR3(27bp)-VH CDR3-FR4(35bp)-}3'.$$

The VH CDR3 size may be deduced from the apparent DNA product size. This may be determined by the Rox dye size marker using the following calculation:

$$\text{Size}_{VH\ CDR3} = (\text{Size}_{Apparent\ DNA\ product\ size} - 60)/3$$

Where $60 = (62_{Frameworks\ on\ both\ ends} = 1_{3'\ A\ overhang} + 3_{DNA\ marker\ underestimation})$ 15. PCR for Library DNA Template Amplification For selecting outputs from first and second rounds, cDNA (supernatants from RT reactions) may be dialyzed against water using an 8 kDa cut-off and the entire amount of cDNA may be used as the PCR template. For selecting outputs from later rounds, 10% of cDNA is used as template for PCR, and the dialysis is typically not necessary. The exemplary amplification primers are shown in Table 6.

TABLE 6

Amplification primers

| Primer | Sequence (5'-3') |
|---|---|
| Forward primer for all scFv and VH libraries | |
| T7TMVUTR$^a$ (SEQ ID NO: 1) | TAATACGACTCACTATAGGGACAATTACTATTTACAATTACA |
| Forward primer for all Vκ and Vλ libraries | |
| VL-T7TMVTag3GS-Fwd (SEQ ID NO: 2) | TAATACGACTCACTATAGGGACAATTACTATTTACAATTACAGGCTTTGGACCATGGGGTCTGGCGGCGGAGGTAGCG |
| Reverse primers for all κ scFv and Vκ libraries | |
| Ck1-FlagA20 Rev (SEQ ID NO: 3) | TTTTTTTTTTTTTTTTTTTTAAATAGCGGATGCCTTGTCGTCGTCGTCCTTGTAGTCGAA GACAGAT |
| Ck2-FlagA20 Rev (SEQ ID NO: 4) | TTTTTTTTTTTTTTTTTTTTAAATAGCGGATGCCTTGTCGTCGTCGTCCTTGTAGTCGAAGACAGATGGT |
| Ck3-FlagA20 Rev (SEQ ID NO: 5) | TTTTTTTTTTTTTTTTTTTTAAATAGCGGATGCCTTGTCGTCGTCGTCCTTGTAGTCGAAGACAGATGGTGCA |
| Ck4-FlagA20 Rev (SEQ ID NO: 6) | TTTTTTTTTTTTTTTTTTTTAAATAGCGGATGCCTTGTCGTCGTCGTCCTTGTAGTCGAAGACAGATGGTGCAGCC |
| Ck5-FlagA20 Rev $^b$ (SEQ ID NO: 7) | TTTTTTTTTTTTTTTTTTTTAAATAGCGGATGCCTTGTCGTCGTCGTCCTTGTAGTCGAAGACAGATGGTGCAGCCACA |

TABLE 6-continued

Amplification primers

| Primer | Sequence (5'-3') |
|---|---|

Reverse primers for all λ scFv and Vλ libraries

| Primer | Sequence (5'-3') |
|---|---|
| CL1FLAGA20 Rev [b] (SEQ ID NO: 8) | TTTTTTTTTTTTTTTTTTTAAATAGCGGATGCCTTGTCGTC GTCGTCCTTGTAGTCAGTGACAGTG |
| CL2FLAGA20 Rev (SEQ ID NO: 9) | TTTTTTTTTTTTTTTTTTTAAATAGCGGATGCCTTGTCGTC GTCGTCCTTGTAGTCAGTGACAGTGGGG |
| CL3FLAGA20 Rev (SEQ ID NO: 10) | TTTTTTTTTTTTTTTTTTTAAATAGCGGATGCCTTGTCGTC GTCGTCCTTGTAGTCAGTGACAGTGGGGTTG |
| CL4FLAGA20 Rev (SEQ ID NO: 11) | TTTTTTTTTTTTTTTTTTTAAATAGCGGATGCCTTGTCGTC GTCGTCCTTGTAGTCAGTGACAGTGGGGTTGGCC |
| CL5FLAGA20 Rev (SEQ ID NO: 12) | TTTTTTTTTTTTTTTTTTTAAATAGCGGATGCCTTGTCGTC GTCGTCCTTGTAGTCAGTGACAGTGGGGTTGGCCTTG |

Reverse primer for all VH libraries

| Primer | Sequence (5'-3') |
|---|---|
| VH-GSFLAGA20-Rev (SEQ ID NO: 13) | TTTTTTTTTTTTTTTTTTTAAATAGCGGATGCTTTGTCATC ATCATCTTTATAATCGCTACCTCCGCCGCCAGAC |

[a]T7TMVTag-primer (sequence of the Tag depends on the library) can also be used.
[b]Preferred primer An exemplary PCR reaction for library DNA template amplification is shown in Table 7 below.

TABLE 7

The exemplary PCR reaction for library DNA template amplification

| cDNA template | X μL |
|---|---|
| dH$_2$O | add to 790 μL |
| 10X High Fidelity Taq DNA Polymerase buffer | 100 μL |
| MgSO$_4$ (50 mM) | 40 μL |
| 10 mM dNTP | 20 μL |
| 5' forward primer (10 μM) | 20 μL |
| 3' reverse primer (10 μM) | 20 μL |
| High Fidelity Taq DNA Polymerase | 10 μL |
| Total volume | 1000 μL |

In an exemplary embodiment, 1 mL PCR reactions are used for round 1 and 2 outputs, and 0.5 mL reactions are used for outputs from later rounds. Aliquots of 100 μL reactions should be made from a master mix. The exemplary thermal cycling condition for the amplification of library DNA templates is shown in Table 8 below.

TABLE 8

Thermal cycling conditions for library DNA template amplification

| 94° C. | 2 minutes | |
|---|---|---|
| 94° C. | 20 seconds | |
| 55° C. | 20 seconds | 25 cycles* |
| 68° C. | 1 minute | |
| 68° C. | 5 minute | |
| 4° C. | Hold forever | |

*Note: 25 cycles typically gives sufficient amplification but it may be increased to as many as 35 cycles to gain more products. Non-specific products of various sizes may become more apparent with additional amplification cycles, and the product may need to be gel purified. If possible, it may be helpful to increase the DNA template input rather than the number of amplification cycles.

After PCR, 5 to 10 μL products are loaded on a 1.2% agarose gel with an appropriate DNA size marker to check the result. If products are the correct size (~850 bp for scFv, ~500 bp for VH or VL library) and have minimal non-specific products, they may be used directly in transcription reaction of the next round. The products may need to be gel purified. If gel purification will be done for PCR products, all remaining products on a preparative agarose gel are separated and the specific band containing the products may be cut out for gel extraction. Quantitation of gel purified DNA may be misleading, as residual EtBr in the DNA tends to interfere with the UV absorbance. A more extensive wash step during gel extraction may help alleviate this interference. If possible, DNA concentration should be measured on a spectrophotometer, as the UV scanning traces are quite different between a clean DNA sample and a DNA with residual EtBr. This protocol is subsequently repeated to conduct multiple rounds of selection.

16. Exemplary Reagents and Buffer Compositions

| 10X Chemical Ligation Buffer | |
|---|---|
| Tris, pH 7 | 250 mM |
| NaCl | 1 M |

| Oligo-dT Binding Buffer | 1X | 2X | 3X |
|---|---|---|---|
| Tris, pH 8 | 100 | 200 | 300 mM |
| NaCl | 1 | 2 | 3 M |
| Triton X-100 | 0.05 | 0.1 | 0.15% |

| FLAG Binding Buffer | 1X | 5X |
|---|---|---|
| Phosphate-based buffer | | |
| PBS | 1X | 5X |
| Triton X-100 | 0.025 | 0.125% |
| Alternative HEPES-based buffer | | |
| HEPES | 50 | 250 mM |
| NaCl | 150 | 750 mM |
| Triton X-100 | 0.025 | 0.125% |

| Selection Buffer | |
|---|---|
| Phosphate-based buffer | |
| PBS | 1X |
| BSA | 1 mg/mL |
| Salmon sperm DNA | 0.1 mg/mL |
| Triton X-100 | 0.025% |
| Yeast tRNA (optional, add before use) | 20 ng/mL |

| Alternative HEPES-based buffer | |
|---|---|
| HEPES | 50 mM |
| NaCl | 150 mM |
| BSA | 1 mg/mL |
| Salmon sperm DNA | 0.1 mg/mL |
| Triton X-100 | 0.025% |
| Yeast tRNA (optional, add before use) | 20 ng/mL |

| First strand buffer | |
|---|---|
| Tris-HCl, pH 8.3 | 250 mM |
| KCl | 375 mM |
| MgCl$_2$ | 15 mM |

| 50X FLAG stock solution | |
|---|---|
| FLAG peptide | 25 mg |
| Selection buffer | 5 mL |
| Make 1 mL aliquots and store at −20° C. | |

| FLAG elution solution | |
|---|---|
| 50X FLAG stock solution | 1 mL |
| Selection buffer | 49 mL |
| Make 1 mL aliquots and store at −20° C. | |

Oligo-dT Cellulose Preparation 2.5 g of oligo-dT cellulose may be transferred into a 50 mL tube and mixed with 25 mL of 0.1 N NaOH. The mixture may be spun down at 1500 rpm for 3 minutes and the supernatant discarded. The oligo-dT cellulose may then be washed with 25 mL of 1×Oligo-dT binding buffer and spun down at 1500 rpm for 3 minutes. The supernatant may be discarded. The wash step may be repeated for 3 more times and the pH of the supernatant measured. The pH should be the same as wash buffer (~pH 8.5). The oligo-dT cellulose may be re-suspended to a final volume of 25 mL by adding 1× Oligo-dT binding buffer to make an approximately 50% slurry and stored at 4° C. The Final concentration=100 mg/mL=1 nmol RNA capacity.

Anti-FLAG M2 Agarose Preparation 25 mL of M2 agarose beads may be transferred into a 50 mL of tube and spun down for 5 minutes at 1000 rpm in a Beckman centrifuge (Beckman Coulter, Fullerton, Calif.). The supernatant may be removed by aspiration. The resulting beads may be re-suspended, washed in equal volume of 10 mM glycine (pH 3.5) and spun down for 5 minutes at 1000 rpm. The supernatant is again removed by aspiration. The beads are re-suspended with one column volume of 1× FLAG binding buffer and spun down for 5 minutes at 1000 rpm. The supernatant is removed by aspiration. This wash step may be repeated 3 times and the beads re-suspended with one column volume of 1× binding buffer (containing 1 mg/mL BSA and 100 mg/mL salmon sperm DNA). The mixture may be rotated for 1 hour or overnight at 4° C. and split into aliquots in 2 mL fractions, if desired, and keep at 4° C.

Example 2

Demonstration of Functional mRNA-ScFv Molecules

Four antibodies are used to demonstrate that functional mRNA-scFv molecules can be displayed and bind to their respective antigen: D2E7 (human anti-hTNF), Y61 (human anti-hIL-12), 17/9 (mouse anti-HA), and MAK195 (mouse anti-hTNF). The MAK195 scFv is generated by PCR using the following primers in Table 9.

TABLE 9

Oligonucleotide primers used for the construction of MAK195 mRNA-scFv constructs

| Primers | Sequences |
|---|---|
| T7-MAK195VH-Fwd (SEQ ID NO: 19) | TAATACGACTCACTATAGGGACAATTACTATTT ACAATTACACCATGGAGGTGCAGCTGAAGGAG TCAGG |
| MAK195VHGS-Rev (SEQ ID NO: 20) | CGATCCGCCACCGCCAGAGCCACCTCCGCCTGA ACCGCCTCCACCTGCAGAGACAGTGACCAGAGT CC |
| MAK195VLGS-Fwd (SEQ ID NO: 21) | GGTGGAGGCGGTTCAGGCGGAGGTGGCTCTGG CGGTGGCGGATCGGACATTGTGATGACCCAGTC TC |
| MAK195VL-Rev (SEQ ID NO: 22) | GATGGTGCAGCCACCGTACGTTTTATTTCCAAC TTTGTCCCCGAG |

An anti-HA 17/9 scFv (see Schulze-Gahmen et al. (1993) J. Mol. Biol. 234(4): 1098-118) is generated by PCR using the following primers based on protein sequences A31790 and B31790 downloaded from NCBI's database (see Table 10 below).

TABLE 10

Oligonucleotide primers used for the construction of 17/9 mRNA-scFv constructs

| Primers | Sequences |
|---|---|
| T7TMVUTR-17/9 VH-1 Fwd (SEQ ID NO: 23) | GGACAATTACTATTTACAATTACACCATGGAAG TGCAGCTGGTGGAAAGCGGCGGCGATCTGGTG AAACC |
| 17/9 VH-2 Rev (SEQ ID NO: 24) | GCTGCTAAAGCTAAAGCCGCTCGCCGCGCAGCT CAGTTTCAGGCTGCCGCCCGGTTTCACCAGATC GCCG |
| 17/9 VH-3 Fwd (SEQ ID NO: 25) | GGCTTTAGCTTTAGCAGCTATGGCATGAGCTGG GTGCGCCAGACCCCGGATAAACGCCTGGAATG GGTGG |
| 17/9 VH-4 Rev (SEQ ID NO: 26) | GCCTTTCACGCTATCCGGATAATAGGTATAGCC GCCGCCGTTGCTAATGGTCGCCACCCATTCCAG GCGT |
| 17/9 VH-5 Fwd (SEQ ID NO: 27) | CCGGATAGCGTGAAAGGCCGCTTTACCATTAGC CGCGATAACGCGAAAAACACCCTGTATCTGCAG ATG |
| 17/9 VH-6 Rev (SEQ ID NO: 28) | GTTCGCGGCGCGCGCAATAATACATCGCGCTAT CTTCGCTTTTCAGGCTGCTCATCTGCAGATACA GGGT |
| 17/9 VH-7 Fwd (SEQ ID NO: 29) | ATTGCGCGCGCCGCGAACGCTATGATGAAAAC GGCTTTGCGTATTGGGGCCAGGGCACCCTGGTG ACCGT |
| 17/9 VH-8 GS Rev (SEQ ID NO: 30) | CGATCCGCCACCGCCGCTGCCACCTCCGCCTGA ACCGCCTCCACCCGCGCTCACGGTCACCAGGGT GCCC |
| GS-17/9 VL-1 Fwd (SEQ ID NO: 31) | AGCGGCGGTGGCGGATCGGATATTGTGATGACC CAGAGCCCGAGCAGCCTGACCGTGACCGCGGG CGAAA |
| 17/9 VL-2 Rev (SEQ ID NO: 32) | TGTTTGCCGCTGTTAAACAGGCTCTGGCTGCTG GTGCAGCTCATGGTCACTTTTTCGCCCGCGGTC ACGG |
| 17/9 VL-3 Fwd (SEQ ID NO: 33) | GTTTAACAGCGGCAAACAGAAAAACTATCTGA CCTGGTATCAGCAGAAACCGGGCCAGCCGCCG AAAGTG |
| 17/9 VL-4 Rev (SEQ ID NO: 34) | CGGTAAAGCGATCCGGCACGCCGCTTTCGCGGG TGCTCGCCCAATAAATCAGCACTTTCGGCGGCT GGCC |
| 17/9 VL-5 Fwd (SEQ ID NO: 35) | TGCCGGATCGCTTTACCGGCAGCGGCAGCGGCA CCGATTTTACCCTGACCATTAGCAGCGTGCAGG CGGA |
| 17/9 VL-6 Rev (SEQ ID NO: 36) | AAAGGTCAGCGGGTTGCTATAATCGTTCTGGCA ATAATACACCGCCAGATCTTCCGCCTGCACGCT GCTA |
| 17/9 VL-7 Fwd (SEQ ID NO: 37) | AGCAACCCGCTGACCTTTGGCGGCGGCACCAAA CTGGAACTGAAACGTACGGTGGCTGCACCATCT GTCT |
| 17/9 VL-8 Flag Rev (SEQ ID NO: 38) | TTAAATAGCGGATGCCTTGTCGTCGTCGTCCTT GTAGTCGATGAAGACAGATGGTGCAGCCACC |

The 17/9 antibody sequence is retrieved from NCBI database using the accession numbers A31790 and B31790.

The DNA constructs for these scFv are transcribed in vitro and then translated in the rabbit reticulocyte lysate either as a mRNA-scFv (the protein is attached to the mRNA via a linker with puromycin modification) or as a free scFv (protein is not attached to mRNA). Both types of molecules are purified and subjected to pull-down assays by corresponding biotinylated antigens (see FIG. 4).

Figure 4:
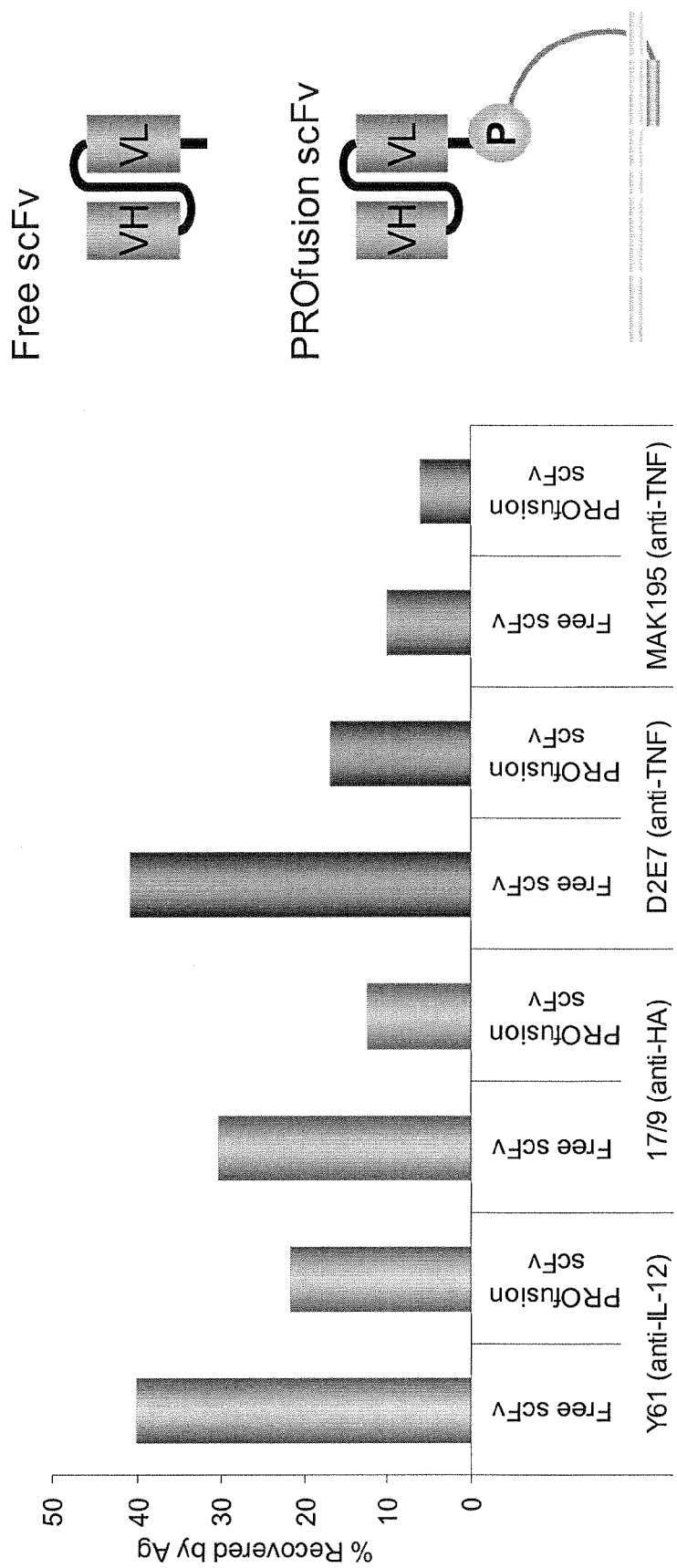
FIG. 4 depicts the functional scFv generated as mRNA-scFv molecules.

The data in FIG. 4 show that the functional mRNA-scFv (bound to biotinylated antigen) molecules are pulled down by streptavidin-magnetic beads, albeit at lower percent recovery than free scFv molecules. Further experiments show that this difference is simply due to the large RNA molecule tethered to the scFv. RNase degradation of the RNA portion from mRNA-scFv molecules restores the scFv recovery by antigens to the same level as that of free scFv molecules (see FIG. 5).

Example 3 mRNA-ScFv Library Construction

Human peripheral blood mononuclear cells (PBMC) from 18 donors are obtained from SeraCare. Table 11 below shows the PBMC analysis by the Fluorescence-activated cell sorting (FACS) method. The poly A RNA is then extracted for the library construction.

TABLE 11

PBMC analysis by FACS

| Lot | Total cell number per vial, $\times 10^6$ | CD20+ cells | | | CD27+/CD20+ total |
|---|---|---|---|---|---|
| | | CD27− | CD27+ | Total | |
| #012505 | 22 | 2.8% | 5.6% | 8.4% | 67% |
| #020805 | 21 | 12.1% | 2.4% | 14.5% | 17% |
| #022205A | 23 | 4.9% | 3.7% | 8.5% | 43% |
| #030305A | 14 | 7.6% | 3.5% | 11.1% | 32% |
| #032905A | 11 | 3.8% | 2.8% | 6.7% | 42% |
| #041205A | 23 | 4.9% | 4.8% | 9.7% | 49% |
| #041405A | 23 | 5.9% | 3.2% | 9.1% | 35% |
| #041905A | 18 | 5.1% | 2.2% | 7.3% | 30% |
| #042604B | 26 | 9.3% | 2.5% | 11.9% | 21% |
| #042805B | 24 | 11.4% | 1.9% | 13.3% | 14% |
| #050305B | 17 | 7.4% | 3.1% | 10.5% | 30% |
| #050505B | 20 | 6.2% | 2.4% | 8.6% | 28% |
| #051005B | 18 | 6.7% | 3.1% | 9.7% | 32% |
| #051205B | 17 | 7.6% | 2.4% | 10.1% | 24% |
| #051705B | 16 | 7.3% | 2.1% | 9.4% | 23% |
| #051905B | 27 | 4.8% | 0.7% | 5.5% | 13% |
| #0524051 | 28 | 7.4% | 2.2% | 9.6% | 23% |
| #122105 | 14 | 11.4% | 1.4% | 12.8% | 11% |

Example 4

Library Tag Selection

Figure 6:
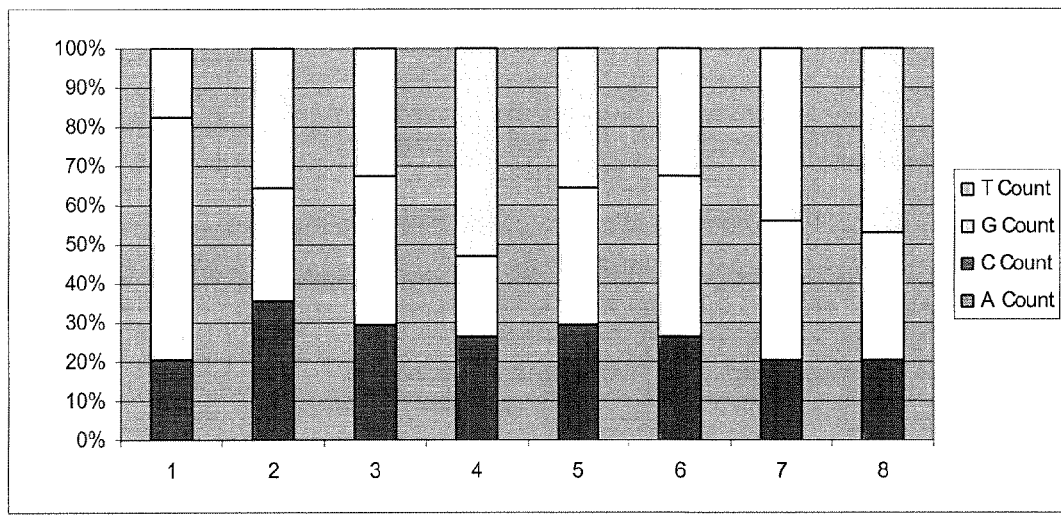
FIG. 6 depicts four 8-bp tags that were inserted between the TMV-UTR and the Kozak consensus sequence of the 17/9 mRNA-scFv construct. The four 17/9 mRNA-scFv constructs, 17_9-tag1, 17_9-tag2, 17_9-tag3, and 17_9-tag4, correspond to SEQ ID NOs: 39, 40, 41, and 42, respectively.
Figure 7:
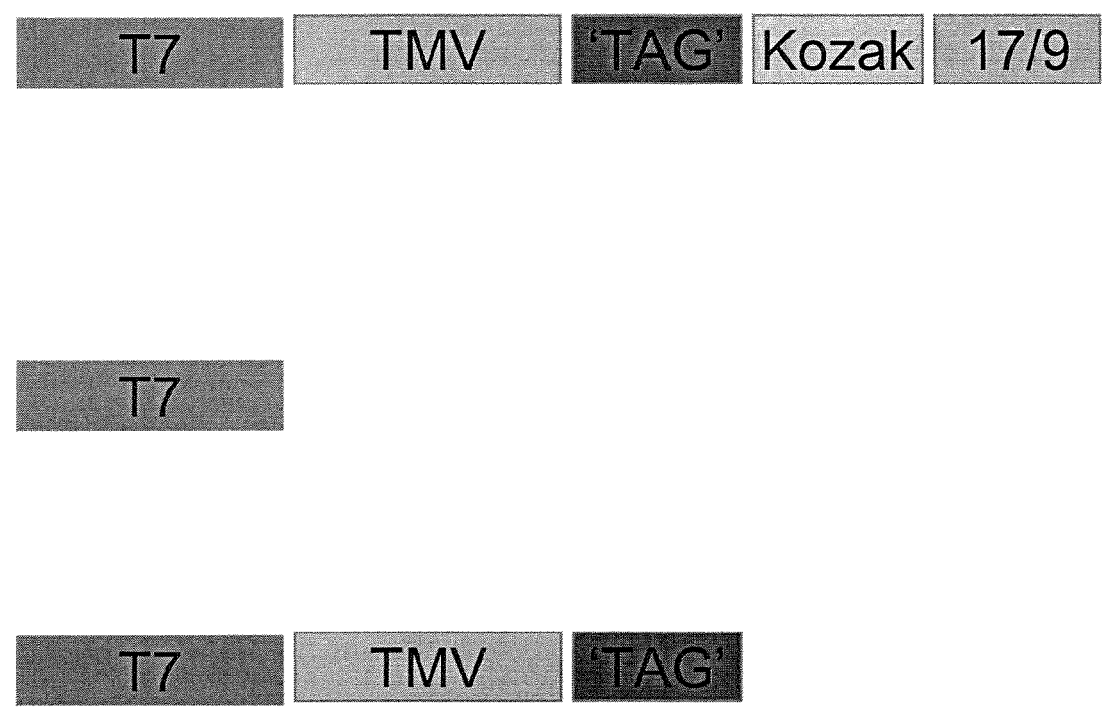

Four 8-base pair tags (SEQ ID NOs: 39-42) are selected and inserted in between TMV-UTR and Kozak consensus sequences of the 17/9 mRNA-scFv construct (see FIG. 6). The tag sequences are designed to not include adenosines and are identified after three rounds of selection. As seen in FIG. 6, the first position prefers G, and the second position prefers T. The random sequence tags are generated by designing 5' primers with eight random (B=G, C, T) nucleotide insertions between TMV and Kozak consensus sequences of 5'UTR (see FIG. 7). The 17/9 scFv is then amplified and selected through 2-3 rounds of selection, where subsequent rounds are reamplified with 5' primers. Sequence outputs are then processed to identify tags that passed through the selection process. The different output tags from each round are shown in FIG. 8. Some repeated sequences are seen inside each round, however no tag sequence is seen in multiple rounds. It should be noted that there is one possible mutation in the tag in round 2, as an ATG sequence should not be possible in a tag sequence.

Example 5

Library Selection for 17/9 ScFv

Figure 9:
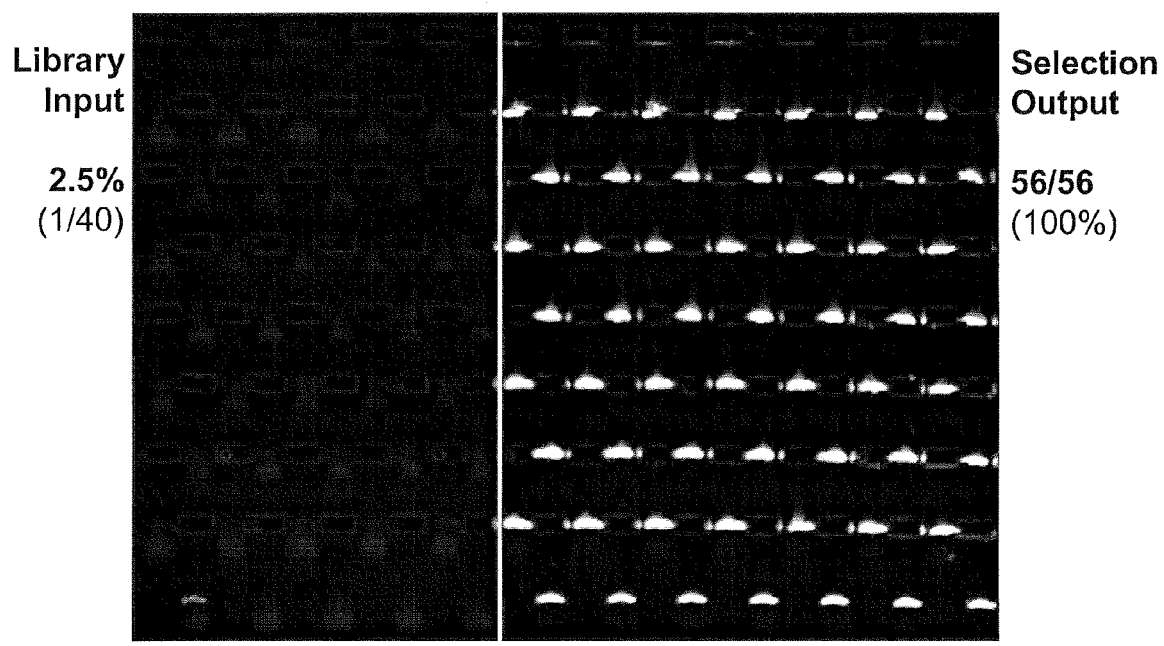
FIG. 9 depicts the results quantifying 17/9 scFv before and after one round of mRNA-scFv selection.

To demonstrate that an mRNA-scFv molecule can be enriched by several rounds of selection using the mRNA display methods described here, an scFv library with a diversity of 25 is constructed by the overlapping PCR method. To create the scFv library, the VH and VL fragments of 17/9, D2E7, 2SD4, Y61 and MAK195 are used as described above. The 17/9 scFv is then selected from this library by biotinylated HA tag. After selection, 17/9 enrichment is examined by cloning and colony PCRs. The results quantifying 17/9 scFv before and after one round of mRNA-scFv selection are shown in FIG. 9.

Example 6 mRNA Display Technology is Used to Discriminate ScFv Binders with Different Affinity To determine whether mRNA display technology, i.e., as described above, is used to discriminate scFv binders with different affinity, chimeras between D2E7 and 2SD4 are made. 2SD4 is the D2E7 scFv precursor that exhibits low affinity (KD ~200 nM as free protein) for TNFα. FIG. 10 depicts the chimeras.

Titration is performed for free proteins. FIG. 11 shows the percent of recovery after antigen binding between the different chimeras, as well as the normalized percent of recovery after antigen selection. The above results show that mRNA display technology as described herein can be used to discriminate binders with different affinity.

Example 7

Thermostability of mRNA-ScFv Molecules

Figure 12:
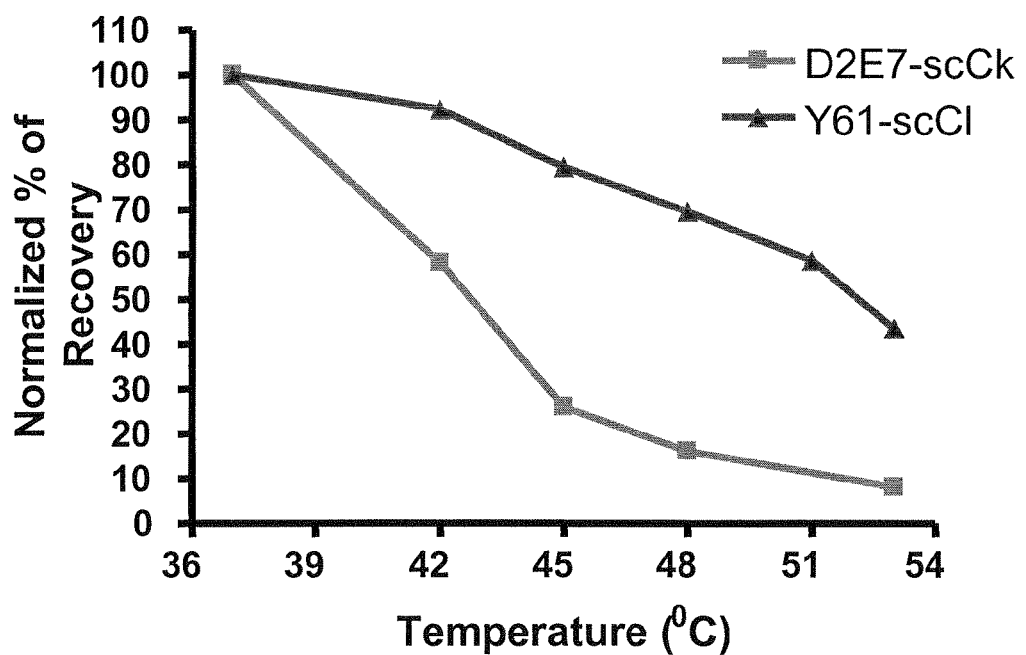
FIG. 12 depicts the thermostability of mRNA-scFv molecules.

To determine the thermostability of mRNA-scFv molecules, D2E7-scCk and Y61-scCk are translated and purified in the mRNA-scFv format, as described herein. The mRNA-scFv molecules are then incubated at different temperatures for 30 minutes prior to antigen selection. The normalized percent of recovery after antigen selection is shown in FIG. 12.

Figure 13:
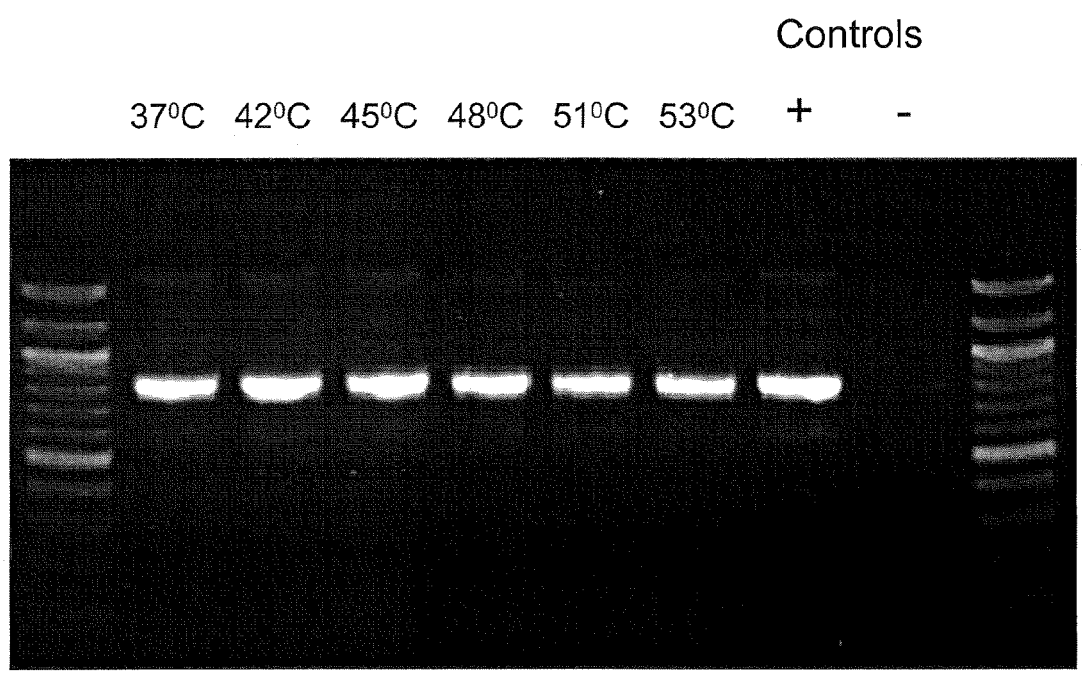
FIG. 13 depicts the results showing that RNA is recovered after high temperature treatment of mRNA-scFv molecules.

FIG. 13 shows that RNA can be recovered after the high temperature treatment of mRNA-scFv molecules. Here, RT-PCR is performed on the beads with recovered Y61-scCl mRNA-scFv molecules.

Example 8

Construction of a Naïve Kappa Profusion ScFv Library from Human PBMC RNA

The following example describes the generation of a human naïve kappa scFv library suitable for the selection using the PROfusion technology.

Human peripheral blood mononuclear cells (PBMCs) are purchased from SeraCare (Milford, Mass., cat. #72000). Cells from different donors are characterized by staining with anti-human CD20-FITC (BD Pharmingen, San Diego, Calif., cat. #556632) and anti-human CD27-PE (BD Pharmingen, cat. #555441) antibodies. Total RNA isolated from PBMCs using RNeasy Midi Kit (QIAGEN, Valencia, Calif., cat. #75144), according to manufacturer's protocol. Briefly, frozen cells are quickly thawed at 37° C., resuspended in a buffer containing guanidine isothiocyanate and homogenized by passing through a 21G needle for multiple times. Ethanol is added and lysate is applied to RNeasy midi columns (18 columns total). Columns are washed, and total RNA is eluted with RNase-free water. RNA concentration and yield are determined by measuring OD 260 nm absorbance. Then mRNA is isolated, according to the kit manual, from the total RNA using Invitrogen Fastrack MAG Maxi mRNA Isolation kit (cat #K1580-02). RNase inhibitor (Invitrogen, Carlsbad, Calif., cat #10777-019) is added during the procedure to minimize RNA degradation. Total RNA is first treated with DNase (Invitrogen, cat #18-68-015) to minimize genomic DNA contamination. Briefly, the oligo-dT-magnetic beads are first washed and then added to the total RNA, incubated at 65° C. for 10 minutes, and then allowed to bind at room temperature for 30 minutes. The beads are washed several times, and the bound mRNA is eluted by RNAse-free water. mRNA is quantified by measuring $OD_{260}$ nm absorbance.

Reverse Transcription

First strand cDNA is then synthesized from 37 μg of mRNA by the SuperScript II Reverse Transcriptase (Invitrogen, Carlsbad, Calif., cat. #18064-014) and a mixture of 15 primers (100 nM total concentration) (Table 12), according to manufacturer's protocol. Reaction is done in two aliquots of 0.9 ml each. RT reaction (1.8 ml total volume) is purified by passing through 36 MicroSpin S-200 HR columns (Amersham Biosciences, Piscataway, N.J., cat. #27-5120-01) (50 μl per column). Columns eluate is incubated with RNaseH for 20 minutes at 37° C.

TABLE 12

Reverse Transcription primers

| Name | Oligo sequence |
|---|---|
| FcγRev1 (SEQ ID NO: 43) | AGTTCCACGACACC |
| FcγRev2 (SEQ ID NO: 44) | GAAGGTGTGCACG |
| FcγRev3 (SEQ ID NO: 45) | CCACGCTGCTGAG |
| FcμRev1 (SEQ ID NO: 46) | ACTTTGCACACCAC |
| FcμRev2 (SEQ ID NO: 47) | TTTGTTGCCGTTGG |
| FcμRev3 (SEQ ID NO: 48) | GGGAATTCTCACAGG |
| FcδRev1 (SEQ ID NO: 49) | GCTGCTTGTCATGT |
| FcδRev2 (SEQ ID NO: 50) | TGCCTTTGGAGACT |
| FcδRev3 (SEQ ID NO: 51) | GACCACGCATTTGT |
| CκRev1 (SEQ ID NO: 52) | TCCACCTTCCACTG |
| CκRev2 (SEQ ID NO: 53) | CAGGCACACAACAG |
| CκRev3 (SEQ ID NO: 54) | GAGTGTCACAGAGC |
| CλRev1 (SEQ ID NO: 55) | GGGAACAGAGTGAC |
| CλRev2 (SEQ ID NO: 56) | GTGTGGCCTTGTTG |
| CλRev3 (SEQ ID NO: 57) | CCATCTGCCTTCCA |

VH cDNA Amplification

One third of above RT reaction is subjected to limited amplification by Platinum Taq DNA Polymerase High Fidelity (Invitrogen, cat. #11304-102) in reactions containing a mixture of VH leader sequence (LS)-specific forward primers (200 nM total concentration) and a mixture of JH-specific reverse primers (200 nM total concentration) (Table 13). PCR conditions are as follows: an initial 2 minutes of 94° C. denaturation; 10 cycles of 94° C. (30 seconds), 55° C. (30 seconds), and 68° C. (60 seconds); followed by 3 minutes of 68° C. extension and 4° C. storage step. PCR products are then purified by QIAquick PCR Purification Kit (QIAGEN, Valencia, Calif., cat. #28106), according to manufacturer's protocol. A small-scale pilot experiment confirms at least 100-fold amplification of cDNA.

TABLE 13

Primers used for VH fragments amplification

| Name | Oligo sequence |
|---|---|
| VH1/7LS (SEQ ID NO: 58) | ATCCTCTTYTTGGTGGSAGC |
| VH1-46LS (SEQ ID NO: 59) | GGTCTTCTGCTTGCTGGCTG |
| VH2LS (SEQ ID NO: 60) | CCTGCTGCTGACCAYCCCTTC |
| VH3LS (SEQ ID NO: 61) | GCTATTTTWVRAGGTGTCCARTGT |
| VH4LS (SEQ ID NO: 62) | GCRGCTCCCAGATGGGTCCTG |
| VH5LS (SEQ ID NO: 63) | ATGGGGTCAACCGCCATCCT |
| VH6LS (SEQ ID NO: 64) | TGGGCCTCCCATGGGGTGTC |
| JH1/2sRev (SEQ ID NO: 65) | CTGAGGAGACRGTGACCAGGGTGC |
| JH4/5sRev (SEQ ID NO: 66) | CTGAGGAGACGGTGACCAGGGTTC |
| JH6sRev (SEQ ID NO: 67) | CTGAGGAGACGGTGACCGTGGTCC |
| JH3sRev (SEQ ID NO: 68) | CTGAAGAGACGGTGACCATTGTCC |

$1/100^{th}$ of purified PCR product is used as a template for amplification of each VH family-specific cDNA. Amplification is carried out by PCR with Platinum Taq DNA Polymerase High Fidelity (Invitrogen, Carlsbad, Calif.) in a reaction containing the individual VH LS-specific forward primer (200 nM) and a mixture of JH-specific reverse primers (200 nM total concentration) (Table 13). PCR conditions are as follows: an initial 2 minutes of 94° C. denaturation; 25 cycles of 94° C. (30 seconds), 55° C. (30 seconds), and 68° C. (40 seconds); followed by 3 minutes of 68° C. extension and 4° C. storage step.

The above PCR products are purified by QIAquick PCR Purification Kit (QIAGEN, Valencia, Calif.) according to manufacturer's protocol. Each PCR product is subsequently amplified by Platinum Taq DNA Polymerase High Fidelity (Invitrogen, Carlsbad, Calif.) in a PCR reaction containing corresponding VH-specific nested forward primer (200 nM) and a mixture of JH-specific reverse primers (200 nM total concentration) (Table 14). The forward primers in each reaction carry an 8-nucleotide "tag" (underlined), which is introduced to increase the specificity during subsequent library amplifications. PCR conditions are as follows: an initial 2 minutes of 94° C. denaturation; 25 cycles of 94° C. (30 seconds), 55° C. (30 seconds), and 68° C. (40 seconds); followed by 3 minutes of 68° C. extension and 4° C. storage step.

TABLE 14

Primers used for nested VH-specific PCR

| Name | Oligo sequence |
|---|---|
| VH1Tag2Forward (SEQ ID NO: 69) | TTTACAATTACAGTGTTGCGACCATGGAGGTGCAGCTGGTGCAGTCTGGRSCT |
| VH2Tag2Forward (SEQ ID NO: 70) | TTTACAATTACAGTGTTGCGACCATGGAGRTCACCTTGARGGAGTCTGGT |
| VH3Tag2Forward (SEQ ID NO: 71) | TTTACAATTACAGTGTTGCGACCATGGAGGTGCAGCTGKTGGAGTCTSGRGGA |
| VH4Tag2Forward (SEQ ID NO: 72) | TTTACAATTACAGTGTTGCGACCATGGAGGTGCAGCTGCAGSAGTSSGGC |
| VH5Tag2Forward (SEQ ID NO: 73) | TTTACAATTACAGTGTTGCGACCATGGAGGTGCAGCTGGTGCAGTCTGGAGCA |
| VH6Tag2Forward (SEQ ID NO: 74) | TTTACAATTACAGTGTTGCGACCATGGAGGTACAGCTGCAGCAGTCAG |
| VH7Tag2Forward (SEQ ID NO: 75) | TTTACAATTACAGTGTTGCGACCATGGAGGTGCAGCTGGTGCAATCTGGGT |
| JHReverse1/2 (SEQ ID NO: 76) | CGCTACCTCCGCCGCCAGACCCGCCTCCACCTGAGGAGACRGTGACCAGGGTGC |
| JHReverse4/5 (SEQ ID NO: 77) | CGCTACCTCCGCCGCCAGACCCGCCTCCACCTGAGGAGACGGTGACCAGGGTTC |
| JHReverse6 (SEQ ID NO: 78) | CGCTACCTCCGCCGCCAGACCCGCCTCCACCTGAGGAGACGGTGACCGTGGTCC |

TABLE 14-continued

Primers used for nested VH-specific PCR

| Name | Oligo sequence |
|---|---|
| JHReverse3 (SEQ ID NO: 79) | CGCTACCTCCGCCGCCAGACCCGCCTCCACCTGAAGAGAC GGTGACCATTGTCC |

PCR products are subjected to 1% agarose gel electrophoresis, and purified by QIAquick Gel Extraction Kit (QIAGEN, Valencia, Calif., cat. #28704). Aliquots of these PCR products are further amplified on large scale in a PCR reaction by Platinum Taq DNA Polymerase High Fidelity (Invitrogen, Carlsbad, Calif.) and 200 nM of the following universal primers:

T7TMVTag2 (SEQ ID NO: 80): TAATACGACTCACTATAGGGACA
ATTACTATTTACAATTAC<u>AGTGTTGCGAC</u>

Library-GS-Reverse (SEQ ID NO: 16): CGCTACCTCCGCCG
CCAGAC.

These primers add a T7 promoter and a TMV-UTR sequence to the 5' end of PCR products, and a partial glycine-serine (G4S)-linker to the 3' end of PCR products. PCR conditions are as follows: an initial 2 minutes of 94° C. denaturation; 26 cycles of 94° C. (30 seconds), 55° C. (30 seconds), and 68° C. (40 seconds); followed by 3 minutes of 68° C. extension and 4° C. storage step.

PCR products are purified with QIAquick PCR Purification Kit (QIAGEN, Valencia, Calif.), quantified by UV absorbance at 260 nm, and aliquots of these products are visualized by 1% agarose gel-electrophoresis to confirm purity. Aliquots of VH family-specific cDNA fragments are cloned using the TOPO TA Cloning Kit (Invitrogen, cat. #45-0641), and individual clones are analyzed by sequencing.

Vκ cDNA Amplification

One third of cDNA generated from the aforementioned RT reaction is subjected to limited amplification by Platinum Taq DNA Polymerase High Fidelity (Invitrogen, Carlsbad, Calif.) in reaction containing a mix of Vκ leader sequence (LS)-specific forward primers (total concentration 200 nM) and Cκ-specific reverse primer (200 nM) (Table 15). PCR conditions are as follows: an initial 2 minutes of 94° C. denaturation; 10 cycles of 94° C. (30 seconds), 55° C. (30 seconds), and 68° C. (60 seconds); followed by 3 minutes of 68° C. extension and 4° C. storage step. A separate small-scale experiment confirms at 10 to 100-fold amplification of cDNA by such PCR.

PCR products are purified with QIAquick PCR Purification Kit (QIAGEN, Valencia, Calif.) according to manufacturer's protocol. 1/500th of purified PCR product is used as a template for amplification of each Vκ family-specific cDNA. Amplification is done by PCR with Platinum Taq DNA Polymerase High Fidelity (Invitrogen, Carlsbad, Calif.) in a reaction containing individual Vκ LS-specific forward primers (200 nM) and Cκ-specific reverse primers (200 nM) (Table 16). PCR conditions are as follows: an initial 2 minutes of 94° C. denaturation; 25 cycles of 94° C. (30 seconds), 55° C. (30 seconds), and 68° C. (40 seconds); followed by 3 minutes of 68° C. extension and 4° C. storage step.

TABLE 15

Primers used for Vκ fragments amplification

| Name | Oligo sequence |
|---|---|
| Vκ1LS (SEQ ID NO: 81) | GCTCCTGGGRCTYCTGC |
| Vκ2LS (SEQ ID NO: 82) | CTYCTGGGGCTGCTAATG |
| Vκ3LS (SEQ ID NO: 83) | CTCTGGCTCMCAGATACCAC |
| Vκ4LS (SEQ ID NO: 84) | GGATCTCTGGTGCCTACGG |
| Vκ5LS (SEQ ID NO: 85) | GGATCTCTGATACCAGGGCA |
| Vκ6LS (SEQ ID NO: 86) | CTGGGTTCCAGCCTCCAG |
| Cκ-sReverse (SEQ ID NO: 87) | GAAGACAGATGGTGCAGCCACAGTTCG |

TABLE 16

Primers used for nested Vκ-specific PCR

| Name | Oligo sequence |
|---|---|
| Vκ1 Forward (SEQ ID NO: 88) | GTCTGGCGGCGGAGGTAGCGGCGGTGGCGGATCGGACA TCCRGWTGACCCAGTCTCCWT |
| Vκ2 Forward (SEQ ID NO: 89) | GTCTGGCGGCGGAGGTAGCGGCGGTGGCGGATCGGATA TTGTGATGACYCAGW**CTCCAC |
| Vκ3 Forward (SEQ ID NO: 90) | CTGGCGGCGGAGGTAGCGGCGGTGGCGGATCGGAAATT GTGWTGACRCAGTCTCCAGSCA |
| Vκ4/6 Forward (SEQ ID NO: 91) | GTCTGGCGGCGGAGGTAGCGGCGGTGGCGGATCGGACA TCGTGMTGACYCAGTCTCCAGA |
| Vκ5 For-Redo (SEQ ID NO: 92) | CTGGCGGCGGAGGTAGCGGCGGTGGCGGATCGGAAACG ACACTCACGCAGTCTCCAGCAT |
| Vκ6 For-NEW (SEQ ID NO: 93) | CTGGCGGCGGAGGTAGCGGCGGTGGCGGATCGGATGTC GTGATGACACAGTCTCCAGCTT |
| Cκ Reverse (SEQ ID NO: 14) | GTCGTCGTCGTCCTTGTAGTCGAAGACAGATGGTGCAGC CACAGTTCG |

PCR products are purified with QIAquick PCR Purification Kit (QIAGEN) according to manufacturer's protocol. Each PCR product is subsequently amplified by Platinum Taq DNA Polymerase High Fidelity (Invitrogen, Carlsbad, Calif.) in a PCR reaction containing corresponding Vκ-specific nested forward primers (200 nM) and Cκ-specific reverse primers (200 nM) (Table 13). PCR conditions are as follows: an initial 2 minutes of 94° C. denaturation; 25 cycles of 94° C.

(30 seconds), 55° C. (30 seconds), and 68° C. (40 seconds); followed by 3 minutes of 68° C. extension and 4° C. storage step.

PCR products are subjected to 1% agarose gel-electrophoresis, and purified by QIAquick Gel Extraction Kit (QIAGEN, Valencia, Calif.). Aliquots of these PCR products are further amplified on large scale in a PCR reaction containing Platinum Taq DNA Polymerase High Fidelity (Invitrogen, Carlsbad, Calif.) and the following universal

```
Library-GS-Forward (SEQ ID NO: 94): GTCTGGCGGCGGAG
GTAGCG

FlagA20Rev (SEQ ID NO: 95): TTTTTTTTTTTTTTTTTTTA
AATAGCGGATGCCTTGTCGTCGTCGTCCTTGTAGTC.
```

These primers add a partial G4S-Linker to the 5' end of PCR product and a FLAG tag, linker annealing site and poly A tail to the 3' end of the resulting PCR products.

PCR conditions are as follows: an initial 2 minutes of 94° C. denaturation; 26 cycles of 94° C. (30 seconds), 55° C. (30 seconds), and 68° C. (30 seconds); followed by 3 minutes of 68° C. extension and 4° C. storage step. PCR products are purified with QIAquick PCR Purification Kit (QIAGEN, Valencia, Calif.), quantified by UV absorbance at 260 nm, and aliquots of these products are visualized by 1% agarose gel-electrophoresis to confirm purity. Part of the obtained Vκ family-specific cDNA fragments are cloned using TOPO TA Cloning Kit (Invitrogen, cat. #45-0641), and individual clones are analyzed by sequencing.

VH-Vκ scFv Construction

VH and Vκ cDNA fragments are mixed according to number of germlines in each family (Table 17 and 18).

TABLE 17

Mixing ratio of VH fragments

| | VH fragment | | | | | | |
|---|---|---|---|---|---|---|---|
| | VH1/7 | VH1-46 | VH2 | VH3 | VH4 | VH5 | VH6 | Total |
| # of germlines | 10 | 1 | 3 | 22 | 7 | 1 | 1 | 45 |
| % of Total | 22.2% | 2.7% | 6.7% | 48.9% | 15.5% | 2.7% | 2.7% | 100% |

TABLE 18

Mixing ration for Vκ fragments

| | Vκ fragment | | | | | |
|---|---|---|---|---|---|---|
| | Vκ1 | Vκ2 | Vκ3 | Vκ4 | Vκ5 | Vκ6 | Total |
| # of germlines | 21 | 11 | 8 | 1 | 1 | 3 | 45 |
| % of Total | 46.7% | 2.4% | 17.8% | 2.7% | 2.7% | 8.3% | 100% |

Total of 10 µg of VH cDNA fragments ($2\times10^{13}$ molecules) and total of 10 µg of Vκ cDNA fragments ($2\times10^{13}$ molecules) is used as template for overlapping PCR. PCR is done with Platinum Taq DNA Polymerase High Fidelity and primers T7TMVTag2 (200 nM) and FlagA20Rev (200 nM), in a volume of 30 ml. PCR conditions are as follows: an initial 2 minutes of 94° C. denaturation; 17 cycles of 94° C. (30 seconds), 55° C. (30 seconds), and 68° C. (60 seconds); followed by 3 minutes of 68° C. extension and 4° C. storage step. Aliquot of PCR product is cloned using TOPO TA Cloning Kit (Invitrogen, cat. #45-0641), and individual clones are analyzed by sequencing.

Spectratyping

A fluorescent dye-labeled 5' forward primer (6-FAM-Pan-VHFR3-Fwd, 5'-GACACGGCCGTGTATTACTGT-3', SEQ ID NO: 17) and a reverse primer (PanJH-Rev, 5'-GCTGAG-GAGACGGTGACC-3', SEQ ID NO: 18) that respectively anneal to the VH's framework 3 region and to the J region are used to amplify across the CDR3 regions of VH domains by PCR. Fifty ng of scFv library DNA template is used in a reaction volume of 30 µl containing 200 nM 6-FAM-Pan-VHFR3-Fwd primer, 200 nM PanJH-Rev primer, 200 µM dNTP, 1× GoTaq buffer, and 1.5 U of GoTaq (Promega, Madison, Wis.). PCR conditions are as follows: an initial 2 minutes of 94° C. denaturation; 30 cycles of 94° C. (20 seconds), 55° C. (20 seconds), and 72° C. (30 seconds); followed by 5 minutes of 72° C. extension and 4° C. storage step. After PCR, 10 µl of products is loaded onto a 2% agarose gel to confirm successful reactions and the remaining products are subjected to spectratyping electrophoresis using an ABI sequencer (Applied Biosystems, Foster City, Calif.). The CDR3 lengths are calculated by subtracting 60 bp flanking framework sequences from the product lengths that are determined by ROX-dye labeled DNA markers.

Results

Human PBMC Characterization

Figure 14:
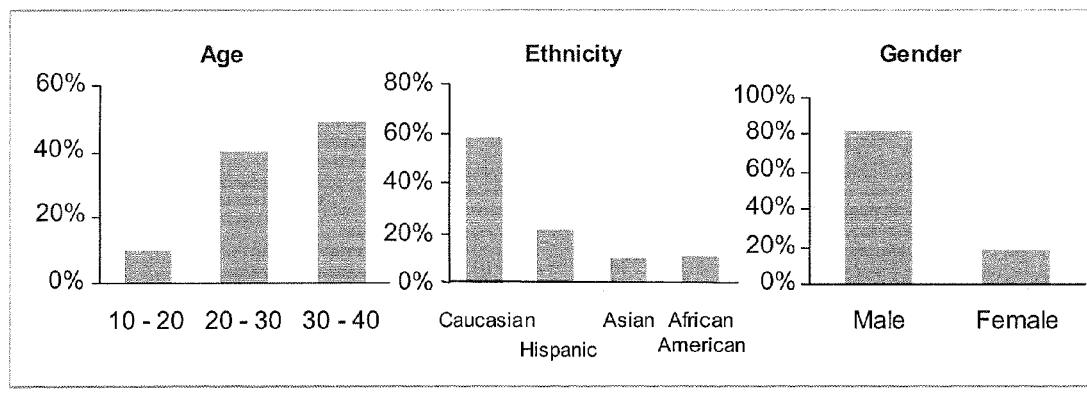
FIG. 14 depicts the age, ethnicity and gender distribution of the PBMCs donors in a naive human PBMC kappa scFv PROfusion library.

Prescreening PBMC samples from 20 donors for B (CD20+) and memory B (CD27+) cells by flow cytometry results in the selection of 10 donors (>9% B in PMBC and <35% memory B cells in total B cells) and allows for the optimization of donor age, gender, and ethnicity distribution to the best extent of donor availability (FIG. 14).

RNA Purification

To obtain antibody cDNA repertoire for library construction, 1.9 mg of total RNA is obtained from $2.3\times10^9$ human PBMCs with an estimated $2.6\times10^8$ B cells. A subsequent poly A mRNA purification from the total RNA yields 42.2 µg of mRNA.

Amplification of VH cDNA Fragments

Figure 15:
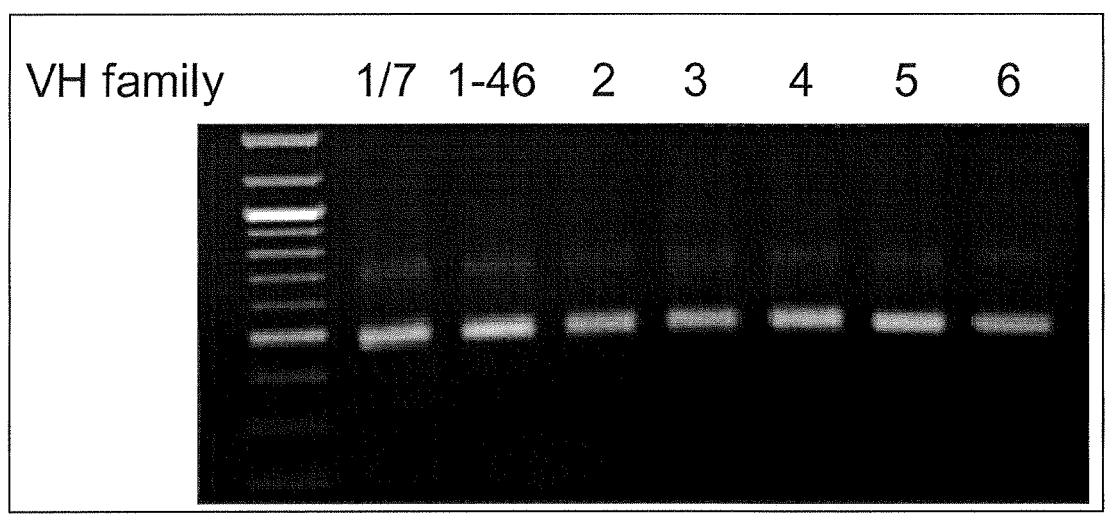
FIG. 15 depicts the VH family-specific PCR fragments in the constructed naive human PBMC kappa scFv PROfusion library.

Aliquots of VH family-specific cDNA fragments of ±500 bp amplified by the VH universal primers (T7TMVTag2, SEQ ID NO: 80 and library-GS-Rev, SEQ ID NO: 16) are visualized by agarose gel-electrophoresis (FIG. 15).

Sequencing analysis of individual VH clones is presented in Table 19. Comparison of cloned VH sequences to known VH germline sequences confirms highly specific amplifications by the VH family-specific primers.

Amplification of Vκ Fragments

Figure 16:
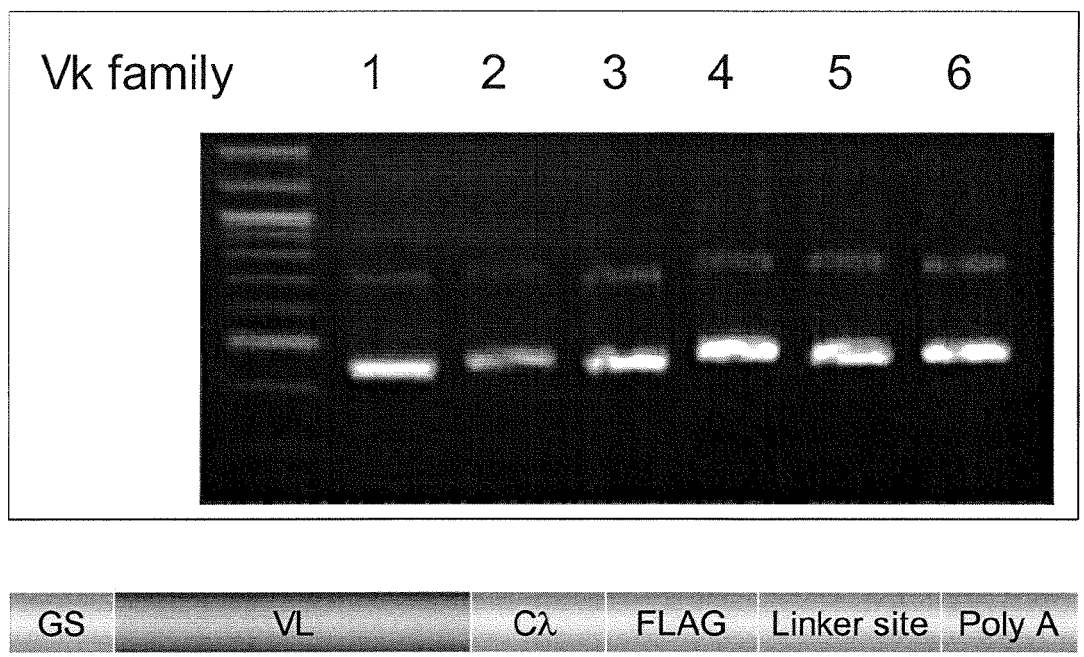
FIG. 16 depicts the Vκ family-specific PCR fragments in the constructed naive human PBMC kappa scFv PROfusion library.

Aliquots of Vκ family-specific cDNA fragments, amplified with universal primers (Library-GS-Fwd, SEQ ID NO: 94 and FlagA20Rev, SEQ ID NO: 95), are visualized by agarose gel-electrophoresis (FIG. 16). Sequencing analysis of individual Vκ clones is presented in Table 20. The data confirms the primer specificity for each of the Vκ germline family.

TABLE 19

Sequencing analysis of VH family-specific PCR products

| Fragment | # of clones | Germline match | Family |
|---|---|---|---|
| VH1/7 | 3 | VH7-4.1 | VH7 |
| | 1 | VH7-4.1/VH7-81 | VH7 |
| | 7 | VH1-8 | VH1 |
| | 4 | VH1-69 | VH1 |
| | 1 | VH1-24 | VH1 |
| VH3 | 3 | VH3-23 | VH3 |
| | 1 | VH3-21 | VH3 |

TABLE 19-continued

Sequencing analysis of VH family-specific PCR products

| Fragment | # of clones | Germline match | Family |
|---|---|---|---|
|  | 1 | VH3-48 | VH3 |
|  | 2 | VH3-9 | VH3 |
|  | 1 | VH3-43/VH3-9 | VH3 |
|  | 2 | VH3-7 | VH3 |
|  | 2 | VH3-74 | VH3 |
|  | 1 | VH3-30/VH3-33 | VH3 |
| VH4 | 3 | VH4-59 | VH4 |
|  | 2 | VH4-39 | VH4 |
|  | 8 | VH4-34 | VH4 |
|  | 2 | VH4-31 | VH4 |
|  | 1 | VH4-61 | VH4 |
| VH1-46 | 15 | VH1-46 | VH1 |
| VH2 | 12 | VH2-5 | VH2 |
|  | 3 | VH2-26 | VH2 |
| VH5 | 16 | VH5-51 | VH5 |
| VH6 | 16 | VH6-1 | VH6 |

VH-Vκ scFv Construction

Figure 17:
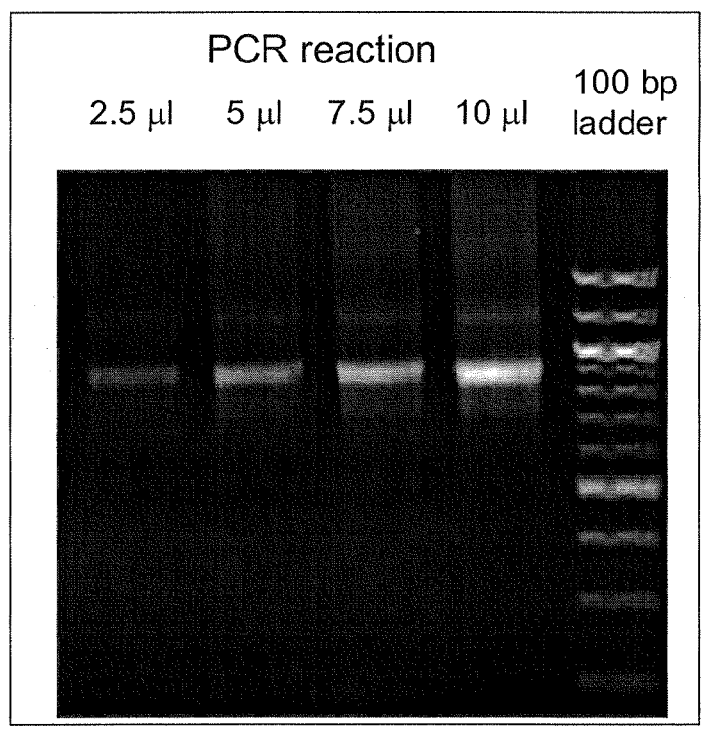
FIG. 17 depicts the VH-Vκ scFv PCR products in the constructed naive human PBMC kappa scFv PROfusion library.
Figure 18:
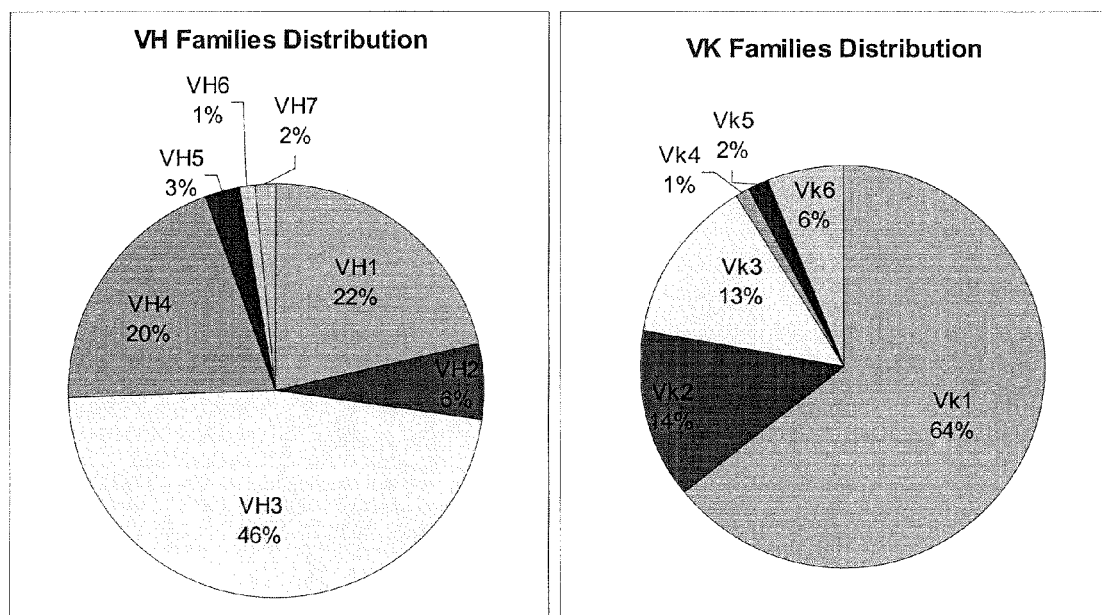
FIG. 18 depicts the VH and Vκ family distribution in the constructed naive human PBMC kappa scFv PROfusion library.

Overlapping PCR is carried out to construct VH-Vκ scFv cDNA fragments. Parts of the obtained products are visualized by agarose gel electrophoresis (FIG. 17). The generated VH-Vκ scFv fragment has all the necessary elements to be selected by the PROfusion mRNA display technology (FIG. 17). Sequencing analysis of individual VH-Vκ scFv clones confirms correct VH-Vκ recombination with a functional intervening G4S linker in a great majority. The distribution of various VH and Vκ families in the constructed scFv library is consistent with previous literature reports (FIG. 18, also see Tsuiji et al. (2006). Exp. Med.; V. 203 (2), pp. 393-400 and Arons et al. (2006) British Journal of Haematology V. 133, pp. 504-512).

TABLE 20

Sequencing analysis of Vκ family-specific PCR products

| Fragment | # of clones | Germline match | Family |
|---|---|---|---|
| Vκ1 | 3 | O18/O8 | Vκ1 |
|  | 3 | O12/O2 | Vκ1 |
|  | 2 | A20 | Vκ1 |
|  | 2 | L19/L5 | Vκ1 |
|  | 1 | L19 | Vκ1 |
|  | 1 | L1/L15 | Vκ1 |
|  | 1 | L1 | Vκ1 |
| Vκ2 | 7 | A19/A3 | Vκ2 |
|  | 3 | A1/A17 | Vκ2 |
|  | 1 | O1/O11 | Vκ2 |
| Vκ3 | 5 | A11/A27 | Vκ3 |
|  | 4 | L20/L6 | Vκ3 |
|  | 2 | L16/L2 | Vκ3 |
| Vκ4 | 14 | B3 | Vκ4 |
| Vκ5 | 13 | B2 | Vκ5 |
| Vκ6 | 12 | A10/A26 | Vκ6 |
|  | 1 | A14 | Vκ6 |

Spectratyping

Figure 19:
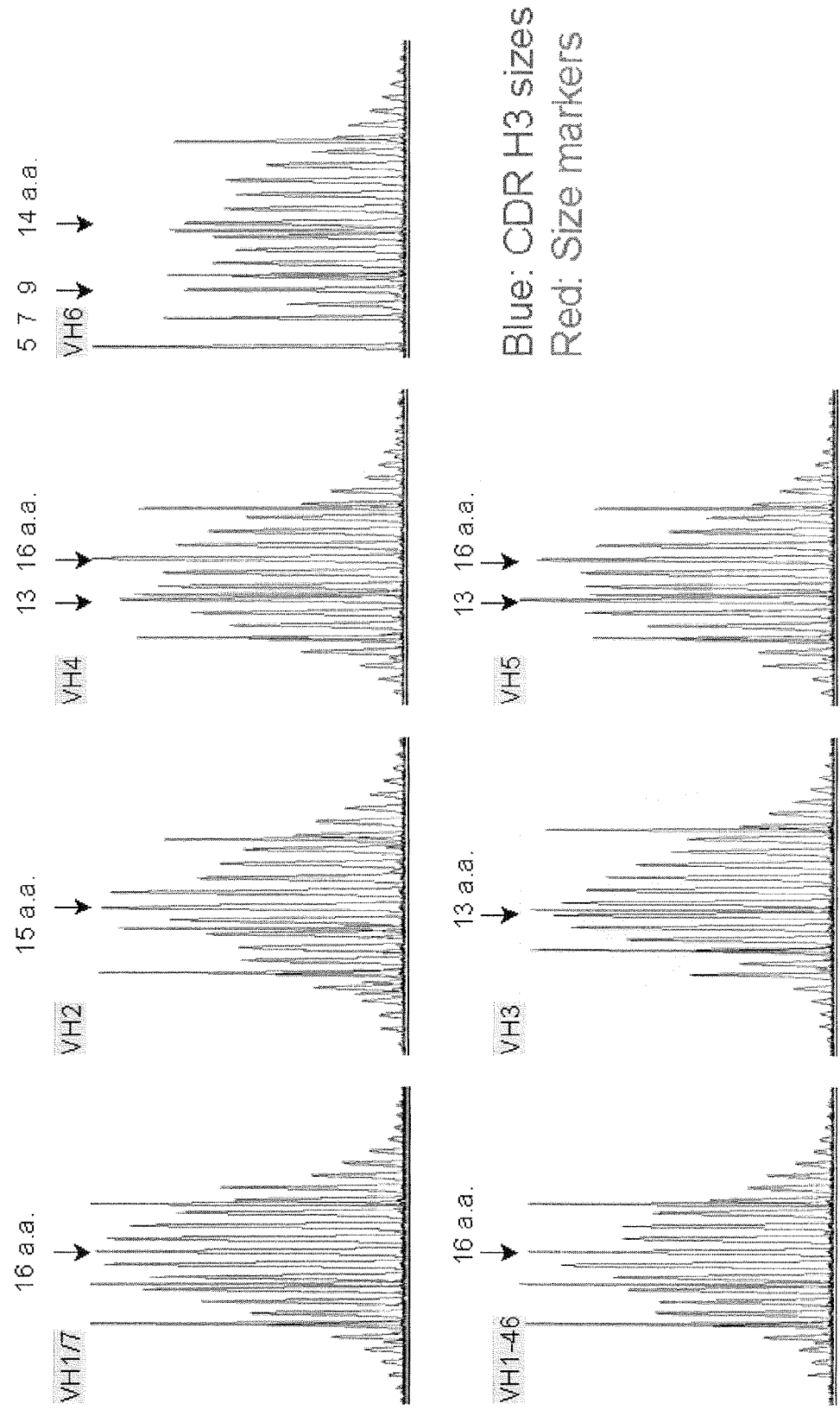
FIG. 19 depicts the spectratyping analysis of naive human PBMC antibody CDR3 sizes.

Spectratyping analysis of CDR3 size distribution among different VH families is carried out on VH cDNA fragments just prior to their assembly into scFv library (FIG. 19). As would be expected in a cDNA library with a high degree of diversity, the observed CDR3 sizes varies greatly in all families analyzed. The observed peak heights of the different CDR3 sizes assumes a bell shaped curve typical of a normal distribution and is an indication of a very large population size. This is especially evident in the results obtained from a single germline or from very small VH families such as VH1-46, VH2, VH5, and VH6. It is also interesting to note the slight difference of CDR3 sizes in different VH families. For instance, VH1 and VH2 tend to have more CDR3s of 15-16 residues, whereas VH3 have more CDR3s of 13 residues. Taken together, the spectratyping analysis of individual VH families confirms a highly diverse and very large VH sequences in the cDNA library.

Figure 20:
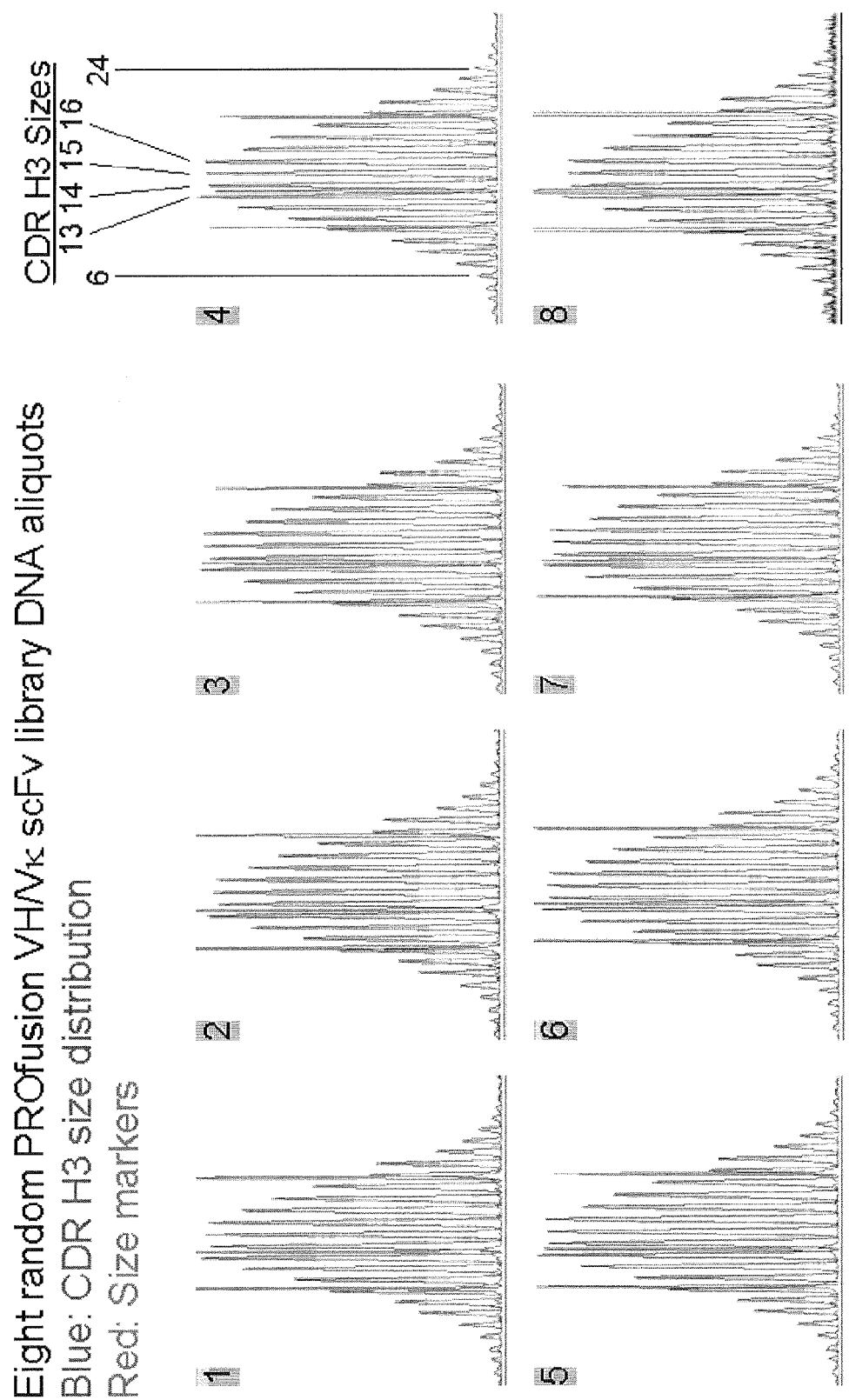
FIG. 20 depicts the quality control of VH/Vκ library by spectratyping analysis.

Eight scFv library templates are randomly sampled and subjected to spectratyping analysis as previously described. The results obtained from all eight samples are indistinguishable, suggesting the library templates in each aliquot are reproducibly similar (FIG. 20). The library VH CDR3 sizes have a normal distribution and the majority fall in between 6 to 24 residues and center in between 13 to 16 residues. This distribution is as expected and consistent with the individual VH family spectratyping results.

Conclusion

The selection of high quality human antibody leads is a prerequisite for successful therapeutic antibody drug development. In additional to a robust selection technology, the antibody library quality (source, diversity, and construction) greatly determines its usefulness to produce good leads. Many human donors were prescreened for greater diversity and PCR primers designed with extremely high specificity to cover all antibody germline sequences such that all diversity within the donor collection can be captured. The constructed antibody scFv library has a theoretical diversity greater than $2 \times 10^{12}$ from more than $2 \times 10^8$ B cells, which has been substantiated by sequencing multiple clones and by spectratyping.

Example 9

Construction of a Naïve Lambda Profusion ScFv Library From Human PBMC RNA

Total RNA and mRNA purification, mRNA reverse transcription, and VH cDNA amplification by PCR have been described in Example 1.

Vλ, cDNA Amplification

One third of cDNA generated from the aforementioned RT reaction is subjected to limited amplification by Platinum Taq DNA Polymerase High Fidelity (Invitrogen, Carlsbad, Calif.) in a reaction containing a mix of Vλ, leader sequence (LS)-specific forward primers (total concentration 200 nM) and Cλ-specific reverse primer (200 nM) (Table 21). The PCR conditions are as follows: an initial 2 minutes of 94° C. denaturation; 10 cycles of 94° C. (30 seconds), 55° C. (30 seconds), and 68° C. (60 seconds); followed by 5 minutes of 68° C. extension and 4° C. storage step. A separate small-scale experiment confirms a 10 to 100-fold amplification of cDNA by such PCR.

TABLE 21

Primers used for Vλ fragments amplification

| Name | Oligo sequence |
|---|---|
| VL1LS1 (SEQ ID NO: 96) | TCACTGTGCAGGGTCCTG |
| VL1LS3 (SEQ ID NO: 97) | TCACTGCACAGGGTCCTG |

TABLE 21-continued

Primers used for Vλ fragments amplification

| Name | Oligo sequence |
| --- | --- |
| VL2LS3 (SEQ ID NO: 98) | TCAGGRCACAGGGTCCTG |
| VL2LS4 (SEQ ID NO: 99) | TCAGGGCACAGGATCCTG |
| VL3LS2 (SEQ ID NO: 100) | TGCATAGGTTCTGTGGTTTCTTCTG |
| VL3LS3 (SEQ ID NO: 101) | ACAGGHTCTGWGGCCTCCTATG |
| VL3LS4 (SEQ ID NO: 102) | TGCACAGGCTCTGTGACCTCCTATG |
| VL3LS5 (SEQ ID NO: 103) | TACACAGGCTCTATTGCCTCCTATG |
| VL4ABLS2 (SEQ ID NO: 104) | TCCACTGSACAGGGTCTCTCT |
| VL4CLS2 (SEQ ID NO: 105) | CTTCATTTTCTCCACAGGTCTCT-GTG |
| VL5LS (SEQ ID NO: 106) | CACTGCACAGGTTCCCTC |
| VL6LS (SEQ ID NO: 107) | CTGCACAGGTTCTTGGGC |
| VL7LS (SEQ ID NO: 108) | CTCACTTGCTGCCCAGGG |
| VL8LS (SEQ ID NO: 109) | GCTTATGGATCAGGAGTGGATTC |
| VL9LS (SEQ ID NO: 110) | CACCCTCCTCAGTCTCCTC |
| VL10LS (SEQ ID NO: 111) | CTCTGCAGTGTCAGTGGTC |
| CJLS Reverse (SEQ ID NO: 112) | GCCTTGGGCTGACCKAGGACGGT |

The PCR product is purified using QIAquick PCR Purification Kit (QIAGEN) according to manufacturer's protocol. $1/250^{th}$ of the purified PCR product is used as a template for amplification of each Vλ family-specific cDNA. Amplification is done by PCR with Platinum Taq DNA Polymerase High Fidelity (Invitrogen, Carlsbad, Calif.) in a reaction containing individual Vλ LS-specific forward primer (200 nM) and Cλ-specific reverse primer (200 nM) (Table 22). The PCR conditions are as follows: an initial 2 minutes of 94° C. denaturation; 35 cycles of 94° C. (30 seconds), 55° C. (30 seconds), and 68° C. (60 seconds); followed by 5 minutes of 68° C. extension and 4° C. storage step.

TABLE 22

Primers used for nested Vλ-specific PCR

| Name | Oligo sequence |
| --- | --- |
| VL1/10 ForRedo (SEQ ID NO: 113) | GTCTGGCGGCGGAGGTAGCGGCGGTGGCGATCGCAGTCTGKGCTGACKCAGCCRC |
| VL2 For (SEQ ID NO: 114) | GTCTGGCGGCGGAGGTAGCGGCGGTGGCGGATCGCAGTCTGCCCTGACTCAGCCT |
| VL3 ForNew (SEQ ID NO: 115) | GTCTGGCGGCGGAGGTAGCGGCGGTGGCGGATCGTCCTATGAGCTGACDCAG |
| VL4ab For (SEQ ID NO: 116) | GTCTGGCGGCGGAGGTAGCGGCGGTGGCGGATCGCAGCYTGTGCTGACTCAATC |
| VL4c For (SEQ ID NO: 117) | GTCTGGCGGCGGAGGTAGCGGCGGTGGCGGATCGCTGCCTGTGCTGACTCAGCCCCCG |
| VL5/9 ForRedo (SEQ ID NO: 118) | GTCTGGCGGCGGAGGTAGCGGCGGTGGCGGATCGCAGCCTGTGCTGACTCAGCCRBT |
| VL6 For (SEQ ID NO: 119) | GTCTGGCGGCGGAGGTAGCGGCGGTGGCGGATCGAATTTTATGCTGACTCAGCCC |
| VL7/8 For (SEQ ID NO: 120) | GTCTGGCGGCGGAGGTAGCGGCGGTGGCGGATCGCAGRCTGTGGTGACYAGGAG |
| CJL Reverse (SEQ ID NO: 15) | GTCGTCGTCGTCCTTGTAGTCAGTGACAGTGGGGTTGGCCTTGGGCTGACCKAGGACGGT |

The PCR products are run on a 2% agarose gel, and purified using QuantumPrep FreezeNSqueeze Columns (Biorad, Hercules, Calif.) according to the manufacturer's protocol. Each PCR product is subsequently amplified by Platinum Taq DNA Polymerase High Fidelity (Invitrogen, Carlsbad, Calif.) in a PCR reaction containing corresponding Vλ-specific nested forward primer (200 nM) and Cλ-specific reverse primers (200 nM) (Table 13). The PCR conditions are as follows: an initial 2 minutes of 94° C. denaturation; 35 cycles of 94° C. (30 seconds), 55° C. (30 seconds), and 68° C. (60 seconds); followed by 5 minutes of 68° C. extension and 4° C. storage step.

PCR products are run on a 2% agarose gel, and purified using QuantumPrep FreezeNSqueeze Columns (Biorad, Hercules, Calif.). Aliquots of these PCR products are further amplified on a large scale in a PCR reaction containing Platinum Taq DNA Polymerase High Fidelity (Invitrogen, Carlsbad, Calif.) and the following universal primers (200 nM):

```
Library-GS-Forward (SEQ ID NO: 94): GTCTGGCGGCGGAG
GTAGCG

FlagA20Rev (SEQ ID NO: 95): TTTTTTTTTTTTTTTTTTAA
ATAGCGGATGCCTTGTCGTCGTCGTCCTTGTAGTC.
```

These primers add a partial G4S-Linker to the 5' end of PCR product and a FLAG tag, linker annealing site and poly A tail to the 3' end of the resulting PCR products. The PCR conditions are as follows: an initial 2 minutes of 94° C. denaturation; 35 cycles of 94° C. (30 seconds), 55° C. (30 seconds), and 68° C. (30 seconds); followed by 5 minutes of 68° C. extension and 4° C. storage step. The PCR products are purified using Purelink PCR Purification Kit (Invitrogen, Carlsbad, Calif.), quantified by UV absorbance at 260 nm, and aliquots of these products are visualized by 2% agarose gel-electrophoresis to confirm purity.

Part of the obtained Vλ, family-specific cDNA fragments are cloned using TOPO TA Cloning Kit (Invitrogen, cat. #45-0641), and individual clones are analyzed by sequencing.

VH-Vλ, scFv Construction

VH and Vλ, cDNA fragments are mixed according to the diversity of germlines represented by each PCR product (Tables 23 and 24).

TABLE 23

Mixing ratio of VH fragments

| VH Family | | | | | | | |
|---|---|---|---|---|---|---|---|
| VH1/7 | VH1-46 | VH2 | VH3 | VH4 | VH5 | VH6 | Total |
| % of Total 22.2% | 2.7% | 6.7% | 48.9% | 15.5% | 2.7% | 2.7% | 100% |

TABLE 24

Mixing ratio for Vλ fragments

| VL Family | | | | | | | | | | |
|---|---|---|---|---|---|---|---|---|---|---|
| VL1 | VL2 | VL3 | VL4 | VL5 | VL6 | VL7 | VL8 | VL9 | VL10 | Total |
| % of Total 18.5% | 3.70% | 33.30% | 11.10% | 11.10% | 3.70% | 7.40% | 3.70% | 3.70% | 3.70% | 100% |

A total of 10 μg of VH cDNA fragments ($2 \times 10^{13}$ molecules) and 10 μg of Vλ, cDNA fragments ($2 \times 10^{13}$ molecules) is used as the template for overlapping PCR. PCR is done with Platinum Taq DNA Polymerase High Fidelity and primers T7TMVTag2 (200 nM) and FlagA20Rev (200 nM), in a volume of 30 ml. The PCR conditions are as follows: an initial 2 minutes of 94° C. denaturation; 17 cycles of 94° C. (30 seconds), 55° C. (30 seconds), and 68° C. (60 seconds); followed by 5 minutes of 68° C. extension and 4° C. storage step. An aliquot of the PCR product is cloned using TOPO TA Cloning Kit (Invitrogen, cat. #45-0641), and individual clones are analyzed by sequencing.

Results

Amplification of Vλ Fragments

Figure 21:
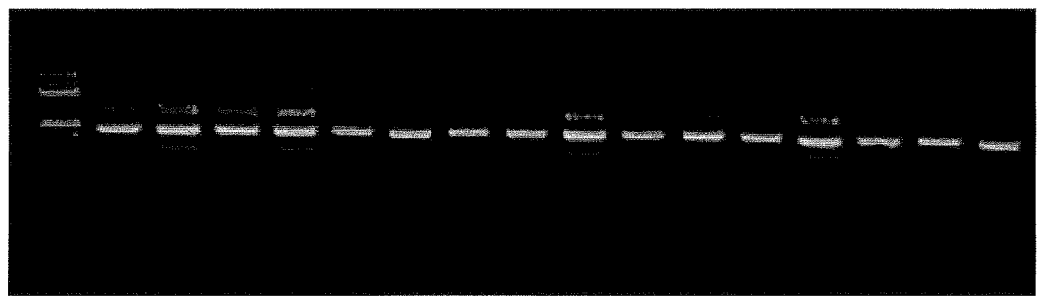
FIG. 21 depicts the Vλ, family-specific PCR fragments in a naive human PBMC lambda scFv PROfusion library.

Aliquots of Vλ, family-specific cDNA fragments, amplified with universal primers (Library-GS-Fwd and FlagA20Rev), are visualized by agarose gel-electrophoresis (FIG. 21).

Sequencing analysis of individual Vλ, clones is presented in Table 25. The data confirm the primer specificity for each of the Vλ, germline family, with one mismatch highlighted in bold (VL1 LS3, Germine V1-3).

TABLE 25

Sequencing analysis of Vλ family-specific PCR products

| VL Fragment | Germline | # of Clones |
|---|---|---|
| VL1 LS1 | V1-16 | 10 |
| | V1-17 | 2 |
| VL1 LS3 | V1-3 | 1 |
| | V1-9 | 8 |
| | V1-13 | 1 |
| VL2 LS3 | V1-3 | 11 |
| VL2 LS4 | V1-3 | 11 |
| VL3 LS2 | V2-13 | 11 |
| VL3 LS3 | V2-1 | 9 |
| | V2-14 | 1 |
| | V2-17 | 1 |
| VL3 LS4 | V2-1 | 7 |
| | V2-6 | 1 |
| | V2-14 | 2 |
| | V2-17 | 1 |
| | V2-19 | 1 |
| VL3 LS5 | V2-1 | 5 |
| | V2-6 | 3 |
| | V2-14 | 1 |
| | V2-17 | 3 |
| VL4ab LS2 | V5-4 | 3 |
| | V5-6 | 9 |
| VL3c LS2 | V5-1 | 12 |
| VL5 LS | V4-1 | 5 |
| | V4-2 | 7 |
| VL6 LS | V1-22 | 10 |
| VL7 LS | V3-2 | 10 |
| VL8 LS | V3-4 | 12 |
| VL9 LS | V5-2 | 12 |
| VL10 LS | V1-20 | 10 |

VH-Vλ scFv Construction

Figure 22:
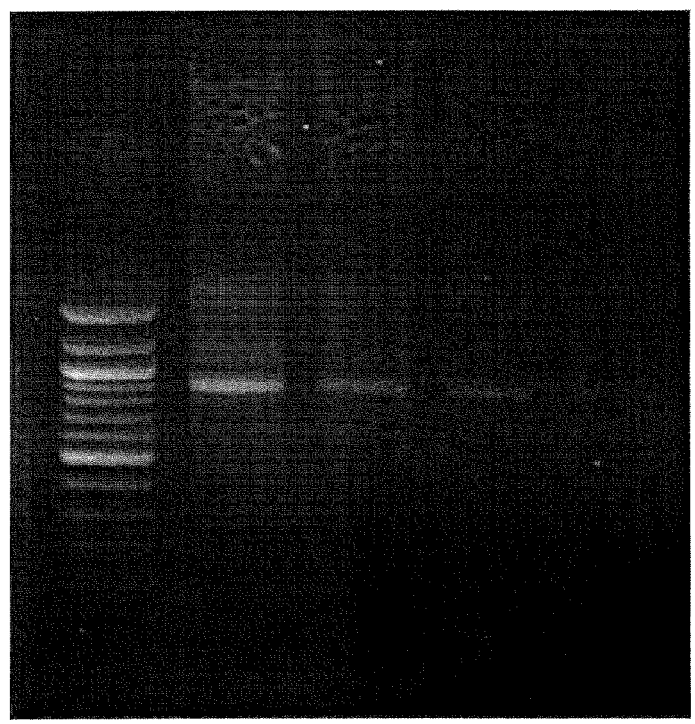
FIG. 22 depicts the VH-Vλ, scFv PCR products in the constructed naive human PBMC lambda scFv PROfusion library.

Overlapping PCR is carried out to construct VH-Vλ scFv cDNA fragments. Parts of the obtained products are visualized by agarose gel electrophoresis (FIG. 22). The generated VH-Vλ scFv fragment has all the necessary elements to be selected by the PROfusion mRNA display technology (FIG. 23).

Sequencing analysis of individual VH-Vλ scFv clones confirms correct VH-Vλ recombination with a functional intervening G4S linker in a great majority.

Example 10

Construction of a Naïve Kappa and Lambda Profusion ScFv Libraries from Human Lymph Node mRNA This Example describes the generation of PROfusion human nave scFv libraries (PBMC kappa and PBMC lambda) from lymph node mRNA.

10.1 Reverse Transcription

First strand cDNA is synthesized from 40 μg of mRNA by SuperScript II Reverse Transcriptase (Invitrogen, cat. #18064-014) and a mixture of 15 primers (100 nM total concentration) (Table 12) according to manufacturer's protocol. Reaction is done in 16 aliquots of 0.1 ml each. RT reactions are pooled (1.6 ml total volume), incubated with 20 μl of RNaseH for 20 minutes at 37° C. and then dialyzed against water.

10.2 PCR 10.2.1 VH cDNA Amplification

One third of above RT reaction is subjected to limited amplification by Platinum Taq DNA Polymerase High Fidelity (Invitrogen, cat. #11304-102) in reactions containing a mixture of VH leader sequence (LS)-specific forward primers (200 nM total concentration) and a mixture of JH-specific reverse primers (200 nM total concentration) (Table 13). PCR conditions are as follows: an initial 2 minutes of 94° C. denaturation; 10 cycles of 94° C. (20 seconds), 55° C. (20 seconds), and 68° C. (60 seconds); followed by 3 minutes of 68° C. extension and 4° C. storage step. PCR product is then purified by QIAquick PCR Purification Kit (QIAGEN, cat. #28106), according to manufacturer's protocol. A small-scale pilot experiment confirms at least 10-fold amplification of cDNA.

Half of purified PCR product is divided into 7 equal aliquots, and each aliquot is used as a template for amplification of one of VH family-specific cDNA. Amplification is carried out by PCR with Platinum Taq DNA Polymerase High Fidelity (Invitrogen, Carlsbad, Calif.) in a reaction containing individual VH LS-specific forward primer (200 nM) and a mixture of JH-specific reverse primers (200 nM total concentration) (Table 13). PCR conditions are as follows: an initial 2 minutes of 94° C. denaturation; 25 cycles of 94° C. (20 seconds), 55° C. (20 seconds), and 68° C. (40 seconds); followed by 3 minutes of 68° C. extension and 4° C. storage step.

The above PCR products are purified by QIAquick PCR Purification Kit (QIAGEN) according to manufacturer's protocol. Each PCR product is subsequently amplified by Platinum Taq DNA Polymerase High Fidelity (Invitrogen, Carlsbad, Calif.) in a PCR reaction containing corresponding VH-specific nested forward primer (200 nM) and a mixture of JH-specific reverse primers (200 nM total concentration) (Table 26). The forward primers in each reaction carry an 8-nucleotide "tag" (underlined), which is introduced to increase the specificity during subsequent library amplifications. PCR conditions are as follows: an initial 2 minutes of 94° C. denaturation; 25 cycles of 94° C. (20 seconds), 55° C. (20 seconds), and 68° C. (40 seconds); followed by 3 minutes of 68° C. extension and 4° C. storage step.

PCR products are subjected to 1% agarose gel electrophoresis, and purified by QIAquick Gel Extraction Kit (QIAGEN, cat. #28704). Aliquots of these PCR products are further amplified on large scale in a PCR reaction by Platinum Taq DNA Polymerase High Fidelity (Invitrogen, Carlsbad, Calif.) and 200 nM of the universal primers (T7TMVTag4s and Lib-GSv2-Rev). These primers add a T7 promoter and a TMV-UTR sequence to 5' end of PCR product, and partial glycine-serine (G4S)-linker to the 3' end of PCR product. PCR conditions are as follows: an initial 2 minutes of 94° C. denaturation; 25 cycles of 94° C. (20 seconds), 55° C. (20 seconds), and 68° C. (40 seconds); followed by 3 minutes of 68° C. extension and 4° C. storage step. PCR products are purified with QIAquick PCR Purification Kit (QIAGEN), quantified by UV absorbance at 260 nm, and aliquots of these products are visualized by 1% agarose gel-electrophoresis to confirm purity. Aliquots of VH family-specific cDNA fragments are cloned using the TOPO TA Cloning Kit (Invitrogen, cat. #45-0641), and individual clones are analyzed by sequencing.

TABLE 26

Primers used for nested VH-specific PCR

| Name | Oligo sequence |
|---|---|
| VH1Tag4 Forward (SEQ ID NO: 121) | TTTACAATTACA<u>GCTTCTTC</u>ACCATGGAGGTGCAGCTGG TGCAGTCTGGRSCT |
| VH2Tag4 Forward (SEQ ID NO: 122) | TTTACAATTACA<u>GCTTCTTC</u>ACCATGGAGRTCACCTTGAR GGAGTCTGGT |
| VH3Tag4 Forward (SEQ ID NO: 123) | TTTACAATTACA<u>GCTTCTTC</u>ACCATGGAGGTGCAGCTGK TGGAGTCTSGRGGA |
| VH4Tag4 Forward (SEQ ID NO: 124) | TTTACAATTACA<u>GCTTCTTC</u>ACCATGGAGGTGCAGCTGC AGSAGTSSGGC |
| VH5Tag4 Forward (SEQ ID NO: 125) | TTTACAATTACA<u>GCTTCTTC</u>ACCATGGAGGTGCAGCTGG TGCAGTCTGGAGCA |

TABLE 26-continued

Primers used for nested VH-specific PCR

| Name | Oligo sequence |
|---|---|
| VH6Tag4 Forward (SEQ ID NO: 126) | TTTACAATTACAGCTTCTTCACCATGGAGGTACAGCTGC AGCAGTCAG |
| VH7Tag4 Forward (SEQ ID NO: 127) | TTTACAATTACAGCTTCTTCACCATGGAGGTGCAGCTGG TGCAATCTGGGT |
| JH1/2 RevV2 (SEQ ID NO: 128) | CAGACCCTCCACCGCCGCTGCCGCCTCCACCTGAGGAGA CRGTGACCAGGGTGC |
| JH3 RevV2 (SEQ ID NO: 129) | CAGACCCTCCACCGCCGCTGCCGCCTCCACCTGAAGAGA CGGTGACCATTGTCC |
| JH4/5 RevV2 (SEQ ID NO: 130) | CAGACCCTCCACCGCCGCTGCCGCCTCCACCTGAGGAGA CGGTGACCAGGGTTC |
| JH6 RevV2 (SEQ ID NO: 131) | CAGACCCTCCACCGCCGCTGCCGCCTCCACCTGAGGAGA CGGTGACCGTGGTCC |
| T7TMVTag4s (SEQ ID NO: 132) | TAATACGACTCACTATAGGGACAATTACTATTTACAATT ACAGCTTCTTC |
| Lib-GSv2-Rev (SEQ ID NO: 133) | CAGACCCTCCACCGCCGCTG |

10.2.2 Vκ cDNA Amplification

One third of cDNA generated from the aforementioned RT reaction is subjected to limited amplification by Platinum Taq DNA Polymerase High Fidelity (Invitrogen, Carlsbad, Calif.) in reaction containing a mix of Vκ leader sequence (LS)-specific forward primers (total concentration 200 nM) and Cκ-specific reverse primer (200 nM) (Table 15). PCR conditions are as follows: an initial 2 minutes of 94° C. denaturation; 10 cycles of 94° C. (20 seconds), 55° C. (20 seconds), and 68° C. (60 seconds); followed by 3 minutes of 68° C. extension and 4° C. storage step. A separate small-scale experiment confirms up to 10-fold amplification of cDNA by such PCR.

PCR product is purified with QIAquick PCR Purification Kit (QIAGEN) according to manufacturer's protocol. Half of purified PCR product is divided into 6 equal aliquots, and each aliquot is used as a template for amplification of individual Vκ family-specific cDNA. Amplification is done by PCR with Platinum Taq DNA Polymerase High Fidelity (Invitrogen, Carlsbad, Calif.) in a reaction containing individual Vκ LS-specific forward primer (200 nM) and Cκ-specific reverse primer (200 nM) (Table 15). PCR conditions are as follows: an initial 2 minutes of 94° C. denaturation; 25 cycles of 94° C. (20 seconds), 55° C. (20 seconds), and 68° C. (40 seconds); followed by 3 minutes of 68° C. extension and 4° C. storage step.

PCR products are subjected to 1% agarose gel-electrophoresis and purified with QIAquick PCR Purification Kit (QIAGEN) according to manufacturer's protocol. Each PCR product is subsequently amplified by Platinum Taq DNA Polymerase High Fidelity (Invitrogen, Carlsbad, Calif.) in a PCR reaction containing corresponding Vκ-specific nested forward primer (200 nM) and Cκ-specific reverse primers (200 nM) (Table 27). PCR conditions are as follows: an initial 2 minutes of 94° C. denaturation; 25 cycles of 94° C. (20 seconds), 55° C. (20 seconds), and 68° C. (40 seconds); followed by 3 minutes of 68° C. extension and 4° C. storage step.

Aliquots of these PCR products are further amplified on large scale in a PCR reaction containing Platinum Taq DNA Polymerase High Fidelity (Invitrogen, Carlsbad, Calif.) and the 200 nM universal primers (Lib-GSv2-Fwd and CKReverse).

Primer Lib-GSv2-Fwd adds a partial G4S-linker upstream of Vκ. The sequences of universal primers encoding for G4S linker (Lib-GSv2-Fwd and Lib-GSv2-Rev) are modified from that of primers used for human PBMC libraries construction (Library-GS-Forward and Library-GS-Reverse). This modification is done to avoid the cross-priming problem of primer Library-GS-Reverse annealing to Framework 1 of VH3 family germlines, which creates truncated VH sequences.

TABLE 27

Primers used for nested Vκ-specific PCR

| Name | Oligo sequence |
|---|---|
| Vκ1FwdV2 (SEQ ID NO: 134) | CAGCGGCGGTGGAGGGTCTGGCGGTGGCGGAAGTGACA TCCRGWTGACCCAGTCTCCWT |
| Vκ2FwdV2 (SEQ ID NO: 135) | CAGCGGCGGTGGAGGGTCTGGCGGTGGCGGAAGTGATA TTGTGATGACYCAGWCTCCAC |
| Vκ3FwdV2 (SEQ ID NO: 136) | CAGCGGCGGTGGAGGGTCTGGCGGTGGCGGAAGTGAAA TTGTGWTGACRCAGTCTCCAGSCA |
| Vκ4/6FwdV2 (SEQ ID NO: 137) | CAGCGGCGGTGGAGGGTCTGGCGGTGGCGGAAGTGACA TCGTGMTGACYCAGTCTCCAGA |
| Vκ5FwdV2 (SEQ ID NO: 138) | CAGCGGCGGTGGAGGGTCTGGCGGTGGCGGAAGTGAAA CGACACTCACGCAGTCTCCAGCAT |
| Vκ6FwdV2 (SEQ ID NO: 139) | CAGCGGCGGTGGAGGGTCTGGCGGTGGCGGAAGTGATG TCGTGATGACACAGTCTCCAGCTT |

TABLE 27-continued

Primers used for nested Vκ-specific PCR

| Name | Oligo sequence |
|---|---|
| CκReverse (SEQ ID NO: 14) | GTCGTCGTCGTCCTTGTAGTCGAAGACAGATGGTGCAGC CACAGTTCG |
| Lib-GSv2-Fwd (SEQ ID NO: 140) | CAGCGGCGGTGGAGGGTCTG |

PCR conditions are as follows: an initial 2 minutes of 94° C. denaturation; 25 cycles of 94° C. (20 seconds), 55° C. (20 seconds), and 68° C. (40 seconds); followed by 3 minutes of 68° C. extension and 4° C. storage step. PCR products are purified with QIAquick PCR Purification Kit (QIAGEN), quantified by UV absorbance at 260 nm, and aliquots of these products are visualized by 1% agarose gel-electrophoresis to confirm purity. Aliquots of the obtained Vκ family-specific cDNA fragments are cloned using TOPO TA Cloning Kit (Invitrogen, cat. #45-0641), and individual clones are analyzed by sequencing.

10.2.3 Vλ, cDNA Amplification

One third of cDNA generated from the aforementioned RT reaction is subjected to limited amplification by Platinum Taq DNA Polymerase High Fidelity (Invitrogen, Carlsbad, Calif.) in a reaction containing a mix of Vλ leader sequence (LS)-specific forward primers (total concentration 200 nM) and Cλ-specific reverse primer (200 nM) (Table 21). The PCR conditions are as follows: an initial 2 minutes of 94° C. denaturation; 10 cycles of 94° C. (20 seconds), 55° C. (20 seconds), and 68° C. (40 seconds); followed by 3 minutes of 68° C. extension and 4° C. storage step. A separate small-scale experiment confirms up to 10-fold amplification of cDNA by such PCR.

The PCR product is purified using QIAquick PCR Purification Kit (QIAGEN) according to manufacturer's protocol. Half of the purified PCR product is divided into 16 equal aliquots and each aliquot is used as a template for amplification of individual Vλ family-specific cDNA. Amplification is done by PCR with Platinum Taq DNA Polymerase High Fidelity (Invitrogen, Carlsbad, Calif.) in a reaction containing individual Vλ LS-specific forward primer (200 nM) and Cλ-specific reverse primer (200 nM) (Table 21). The PCR conditions are as follows: an initial 2 minutes of 94° C. denaturation; 30 cycles of 94° C. (20 seconds), 55° C. (20 seconds), and 68° C. (40 seconds); followed by 3 minutes of 68° C. extension and 4° C. storage step.

PCR products are purified with QIAquick PCR Purification Kit (QIAGEN) according to manufacturer's protocol. The following fragments are pooled before subsequent amplification: VL-1 LS-1 and VL1 LS-3 fragments are pooled in 3:2 ratio into VL1 LS mix fragments; VL-2 LS-3 and VL2 LS-4 fragment are pooled in 3:2 ration into VL2 LS mix fragments; VL3 LS-2, VL3 LS-3, VL3 LS-4 and VL3 LS-5 fragments are pooled into 1:6:1:1 ratio into VL3 LS mix fragments. PCR product corresponding to individual families are subsequently amplified by Platinum Taq DNA Polymerase High Fidelity (Invitrogen, Carlsbad, Calif.) in a PCR reaction containing corresponding Vλ-specific nested forward primer (200 nM) and Cλ-specific reverse primers (200 nM) (Table 22). The PCR conditions are as follows: an initial 2 minutes of 94° C. denaturation; 25 cycles of 94° C. (20 seconds), 55° C. (20 seconds), and 68° C. (40 seconds); followed by 3 minutes of 68° C. extension and 4° C. storage step.

PCR products were subjected to 1% agarose gel-electrophoresis, and purified by QIAquick Gel Extraction Kit (QIAGEN). Aliquots of these PCR products were further amplified on a large scale in a PCR reaction containing Platinum Taq DNA Polymerase High Fidelity (Invitrogen, Carlsbad, Calif.) and the 200 nM universal primers (Lib-GSv2-Fwd and CJLReverse). The PCR conditions were as follows: an initial 2 minutes of 94° C. denaturation; 25 cycles of 94° C. (30 seconds), 55° C. (30 seconds), and 68° C. (30 seconds); followed by 5 minutes of 68° C. extension and 4° C. storage step.

PCR products are purified with QIAquick PCR Purification Kit (QIAGEN), quantified by UV absorbance at 260 nm, and aliquots of these products are visualized by 1% agarose gel-electrophoresis to confirm purity. The specificity of VL family-specific primers is confirmed previously.

10.2.4 VH-Vκ scFv Construction

VH and Vκ cDNA fragments are mixed according to number of germlines in each family (based on NCBI) (Tables 17 and 18)

Total of 10 μg of VH cDNA fragments ($2 \times 10^{13}$ molecules) and total of 10 μg of Vκ cDNA fragments ($2 \times 10^{13}$ molecules) is used as template for overlapping PCR. PCR is done with Platinum Taq DNA Polymerase High Fidelity and primers T7TMVUTR (200 nM) and Ck5-FlagA20 Rev (200 nM), in a volume of 30 ml, with the following steps: an initial 2 minutes of 94° C. denaturation; 12 cycles of 94° C. (20 seconds), 55° C. (20 seconds), and 68° C. (60 seconds); followed by 3 minutes of 68° C. extension and 4° C. storage step. Aliquot of PCR product is cloned using TOPO TA Cloning Kit (Invitrogen, cat. #45-0641), and individual clones are analyzed by sequencing.

T7TMVUTR (SEQ ID NO: 1): TAATACGACTCACTATAGGGACAAT
TACTATTTACAATTACA

Ck5-FlagA20 Rev (SEQ ID NO: 7): TTTTTTTTTTTTTTTTTT
TTAATAGCGGATGCCTTGTCGTCGTCGTCCTTGTAGTCGAAGACAGATGG
TGCAGCCACA.

Primer Ck5-FlagA20 Rev adds polyA tail at the 3'end of PCR product. Thus the sequence is used for Oligo-dT purification of PROfusion molecules.

10.2.5 VH-Vλ scFv Construction

VH and Vλ cDNA fragments are mixed according to the diversity of germlines represented by each PCR product (Tables 18 and 28). A total of 10 μg of VH cDNA fragments ($2 \times 10^{13}$ molecules) and 10 μg of Vλ cDNA fragments ($2 \times 10^{13}$ molecules) is used as the template for overlapping PCR. PCR is done with Platinum Taq DNA Polymerase High Fidelity and primers T7TMVUTR (200 nM) and CL5 FlagA20 (200 nM), in a volume of 30 ml. The PCR conditions are as follows: an initial 2 minutes of 94° C. denaturation; 10 cycles of 94° C. (20 seconds), 55° C. (20 seconds), and 68° C. (60 seconds); followed by 5 minutes of 68° C. extension and 4° C. storage step. Aliquot of the PCR product is cloned using TOPO TA Cloning Kit (Invitrogen, cat. #45-0641), and individual clones are analyzed by sequencing.

TABLE 28

Mixing ratio for Vλ fragments

| | VL fragment | | | | | | | | | | |
|---|---|---|---|---|---|---|---|---|---|---|---|
| | VL1 | VL2 | VL3 | VL4 | VL5 | VL6 | VL7 | VL8 | VL9 | VL10 | Total |
| # of germlines | 5 | 5 | 9 | 3 | 3 | 1 | 2 | 1 | 1 | 1 | 31 |
| % of Total | 16.1% | 16.1% | 29.0% | 9.7% | 9.7% | 3.2% | 6.4% | 3.2% | 3.2% | 3.2% | 100% |

CL5 FlagA20 (SEQ ID NO: 12): TTTTTTTTTTTTTTTTTTTA
AATAGCGGATGCCTTGTCGTCGTCGTCCTTGTAGTCAGTGACAGTGGGGT
TGGCCTTG Primer CL5-FlagA20 adds polyA tail at the 3'end of PCR product. Thus the sequence is used for Oligo-dT purification of PROfusion molecules.

10.3 Spectratyping

A fluorescent dye-labeled 5' forward primer (6-FAM-Pan-VHFR3-Fwd, 5'-GACACGGCCGTGTATTACTGT-3', SEQ ID NO: 17) and a reverse primer (PanJH-Rev, 5'-GCTGAG-GAGACGGTGACC-3', SEQ ID NO: 18) that respectively anneal to the VH's framework 3 region and to the J region are used to amplify across the CDR3 regions of VH domains by PCR. Fifty ng of scFv library DNA template is used in a reaction volume of 30 µl containing 200 nM 6-FAM-Pan-VHFR3-Fwd primer, 200 nM PanJH-Rev primer, 200 µM dNTP, 1× GoTaq buffer, and 1.5 U of GoTaq (Promega, Madison, Wis.). PCR conditions are as follows: an initial 2 minutes of 94° C. denaturation; 30 cycles of 94° C. (20 seconds), 55° C. (20 seconds), and 72° C. (30 seconds); followed by 5 minutes of 72° C. extension and 4° C. storage step. After PCR, 10 µl of products is loaded onto a 2% agarose gel to confirm successful reactions and the remaining products are subjected to spectratyping electrophoresis using an ABI sequencer. The CDR3 lengths are calculated by subtracting 60 bp flanking framework sequences from the product lengths that are determined by ROX-dye labeled DNA markers.

Results

Overview of PROfusion ScFv Library Construction

Figure 24:
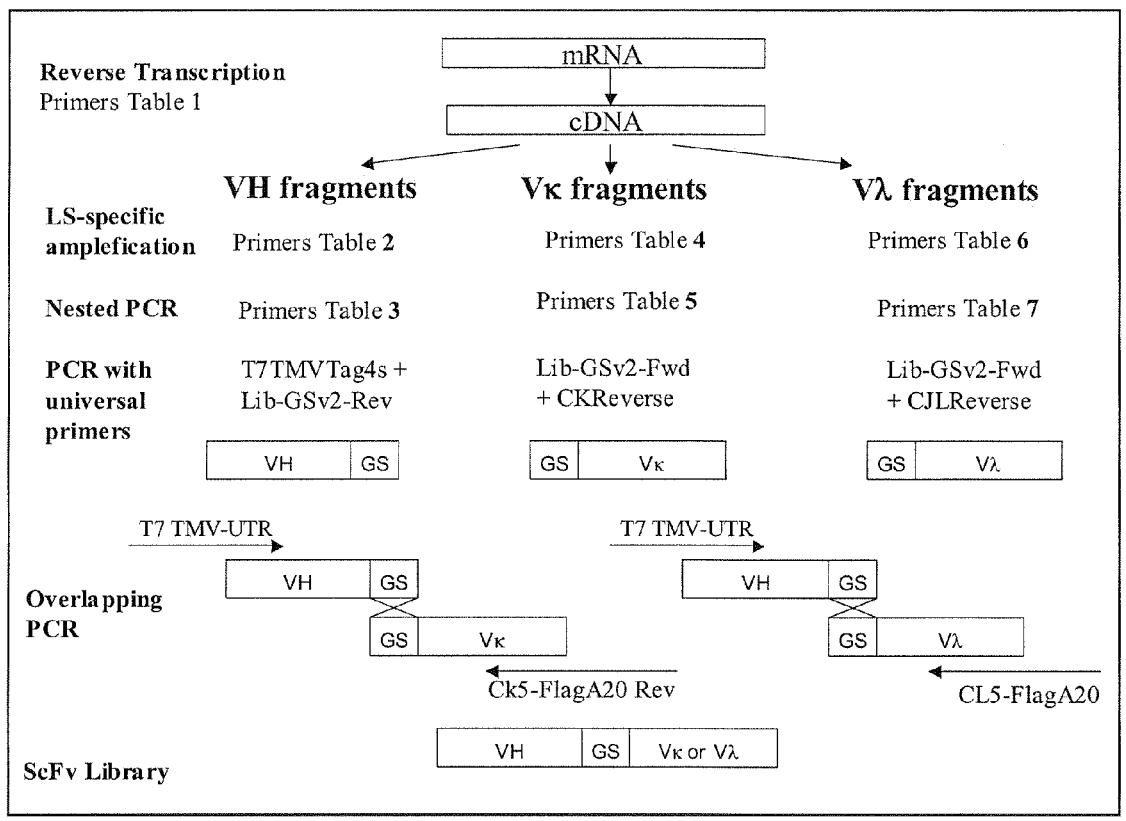
FIG. 24 depicts the schema of PROfusion library constructions in a naive human lymph node kappa and lambda scFv PROfusion libraries.

The flow chart representing different steps in PROfusion libraries construction is presented on FIG. 24.

Amplification of VH cDNA Fragments

Figure 25:
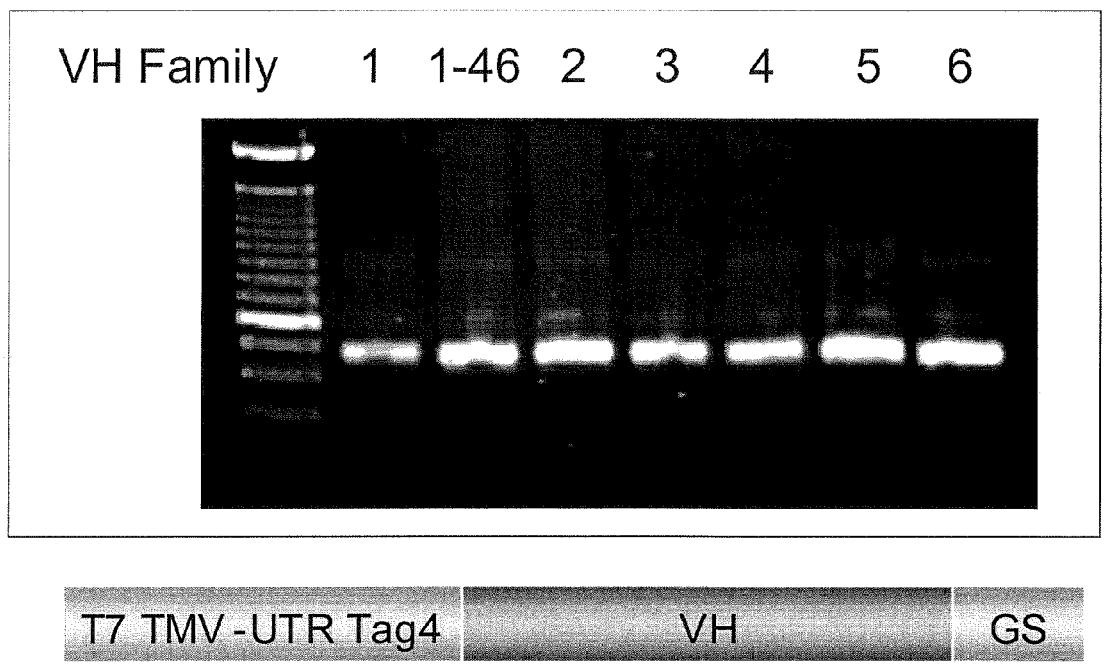
FIG. 25 depicts the VH family-specific PCR fragments in the constructed naive human lymph node kappa and lambda scFv PROfusion libraries.

Aliquots of VH family-specific cDNA fragments (~500 bp) amplified by the VH universal primers (T7TMVUTR and Lib-GSv2-Rev) are visualized by agarose gel-electrophoresis (FIG. 25). Specificity of VH family-specific primers has been previously tested and confirmed again for primers amplifying families with large number of germlines (Table 29).

Amplification of Vκ Fragments

Figure 26:
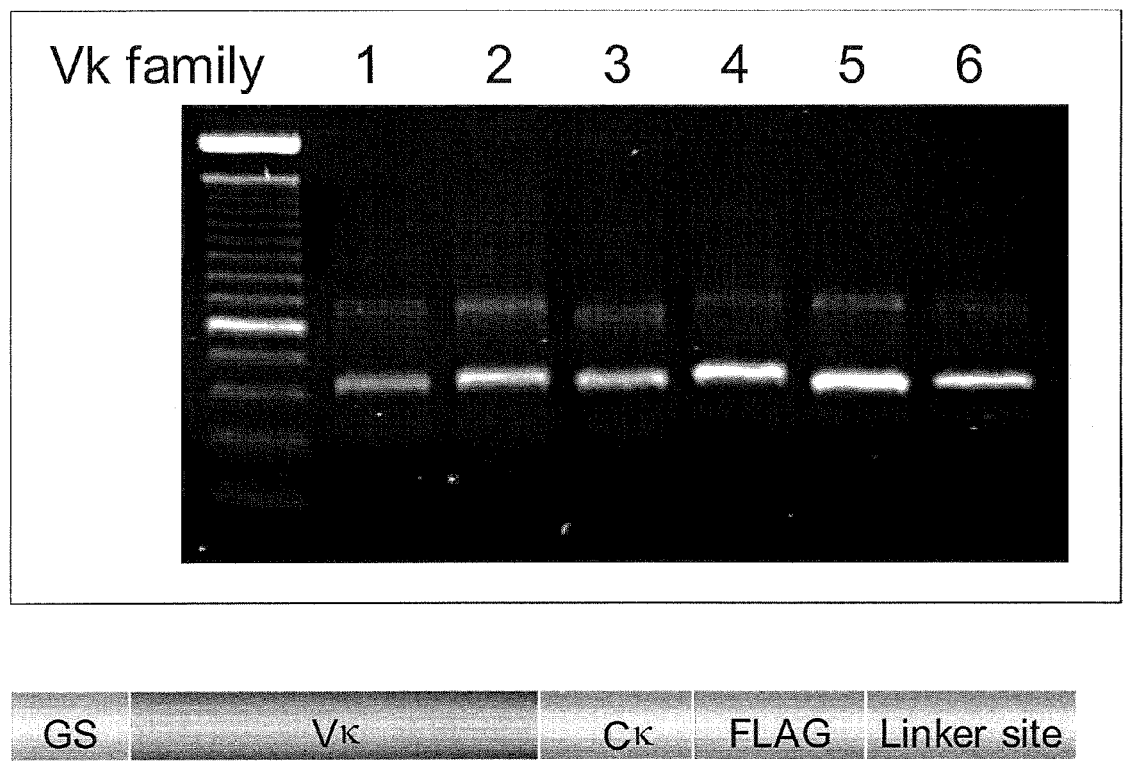
FIG. 26 depicts the Vκ family-specific PCR fragments in the constructed naive human lymph node kappa and lambda scFv PROfusion libraries.

Aliquots of Vκ family-specific cDNA fragments, amplified with universal primers (Lib-GSv2-Fwd: and CK Reverse), are visualized by agarose gel-electrophoresis (FIG. 26). Specificity of Vκ family-specific primers is tested before and confirmed again for primers amplifying families with large number of germlines (Table 30).

TABLE 29

Sequencing analysis of VH family-specific PCR products

| Fragment | # of clones | Germline match | Family |
|---|---|---|---|
| VH1/7 | 8 | VH-1-69 | VH1 |
| | 3 | VH1-8 | VH7 |
| | 2 | VH1-18 | VH1 |

TABLE 29-continued

Sequencing analysis of VH family-specific PCR products

| Fragment | # of clones | Germline match | Family |
|---|---|---|---|
| | 2 | VH1-2 | VH1 |
| | 1 | VH1-24 | VH1 |
| VH2 | 11 | VH2-5 | VH2 |
| | 4 | VH2-26 | VH2 |
| VH4 | 5 | VH4-59 | VH4 |
| | 4 | VH4-55P | VH4 |
| | 4 | VH4-39 | VH4 |
| | 3 | VH4-31 | VH4 |
| VH3 | 11 | VH3-30/VH3-33 | VH3 |
| | 11 | VH3-23 | VH3 |
| | 7 | VH3-7 | VH3 |
| | 5 | VH3-21 | VH3 |
| | 4 | VH3-15 | VH3 |
| | 2 | VH3-9 | VH3 |
| | 2 | VH3-48 | VH3 |
| | 1 | VH3-43 | VH3 |
| | 1 | VH3-53 | VH3 |

TABLE 30

Sequencing analysis of Vκ family-specific PCR products

| Fragment | # of clones | Germline match | Family |
|---|---|---|---|
| Vκ1 | 20 | O12/O2 | Vκ1 |
| | 8 | O18/O8 | Vκ1 |
| | 4 | A20 | Vκ1 |
| | 4 | A30 | Vκ1 |
| | 3 | L19/L5 | Vκ1 |
| | 2 | L1/L15 | Vκ1 |
| | 2 | L8 | Vκ1 |
| | 2 | L11 | Vκ1 |
| | 1 | L12 | Vκ1 |
| | 1 | L14 | Vκ1 |
| | 1 | L18/L4 | Vκ1 |
| Vκ2 | 13 | A19/A3 | Vκ2 |
| | 3 | A17/A1 | Vκ2 |
| | 3 | A18/A2 | Vκ2 |
| | 3 | O1/O11 | Vκ2 |
| Vκ3 | 8 | A11/A27 | Vκ3 |
| | 4 | L20/L6 | Vκ3 |
| | 3 | L16/L2 | Vκ3 |
| Vκ6 | 7 | A10/A26 | Vκ6 |

Amplification of Vλ Fragments

Aliquots of Vλ family-specific cDNA fragments, amplified with universal primers (Lib-GSv2-Fwd, SEQ ID NO: 140, and CJL Reverse, SEQ ID NO: 15), are visualized by agarose gel-electrophoresis (FIG. 27). Specificity of Vλ family-specific primers is tested before.

VH-Vκ and VH-Vλ scFv Construction

Overlapping PCRs are carried out to construct VH-Vκ and VH-Vλ scFv cDNA fragments. Part of the obtained products is visualized by agarose gel electrophoresis (FIG. 27). The generated VH-Vκ and VH-Vλ scFv fragments have all the necessary elements to be selected by the PROfusion mRNA display technology (FIG. 28).

Figure 29:
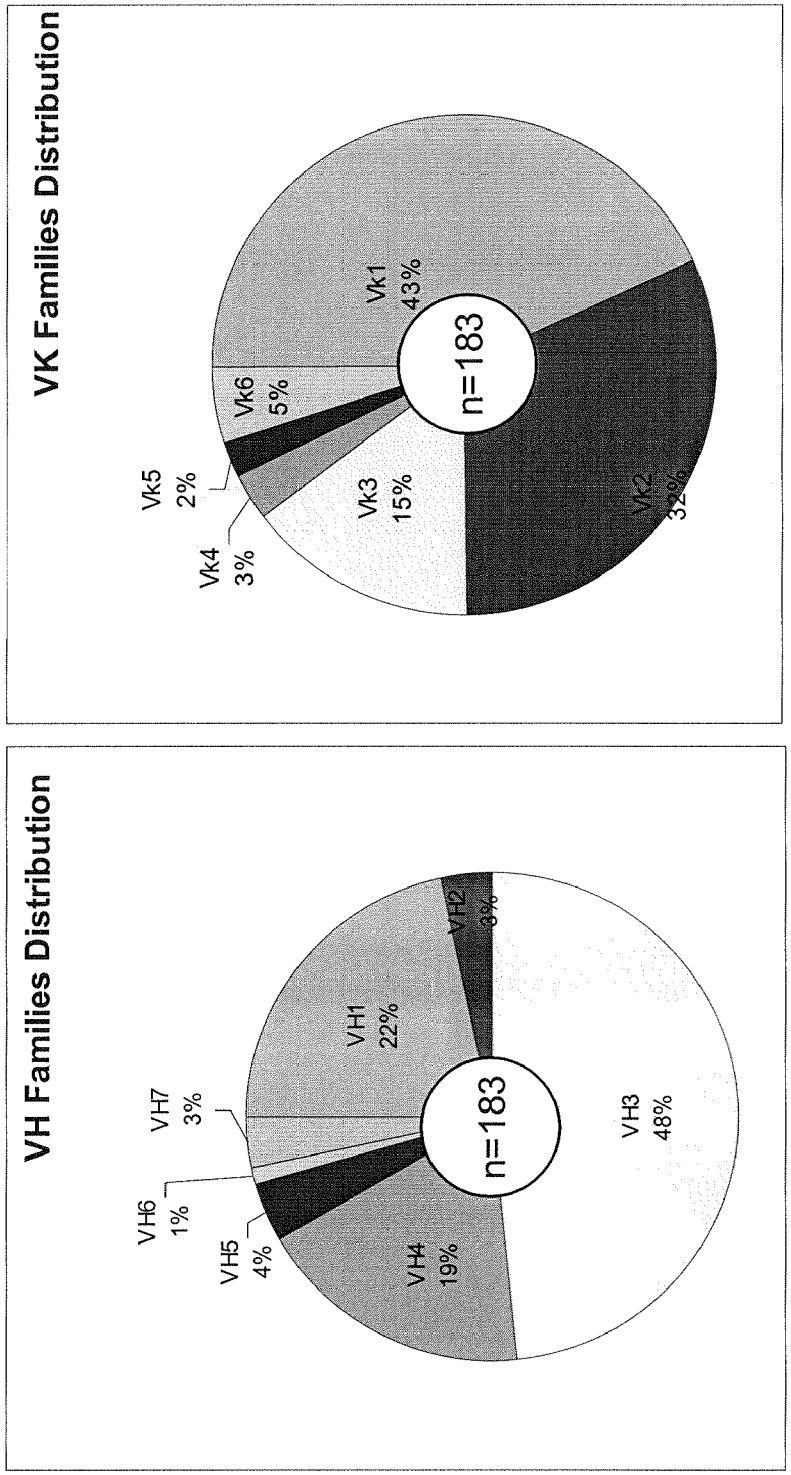
FIG. 29 depicts the VH and Vκ family distribution in a constructed VH-Vκ scFv library.

Sequencing analysis of individual VH-Vκ and VH-Vλ scFv clones confirms the correct VH-Vκ and VH-Vλ recombination with a functional intervening G4S linker in a great majority of the clones. The distribution of various VH and Vκ and Vλ families in the constructed scFv library is consistent with previous literature reports (FIG. 29, FIG. 30, also see Tsuiji et al. (2006). Exp. Med.; V. 203 (2), pp. 393-400 and Arons et al. (2006) British Journal of Haematology V. 133, pp. 504-512).

Spectratyping

Figure 31:
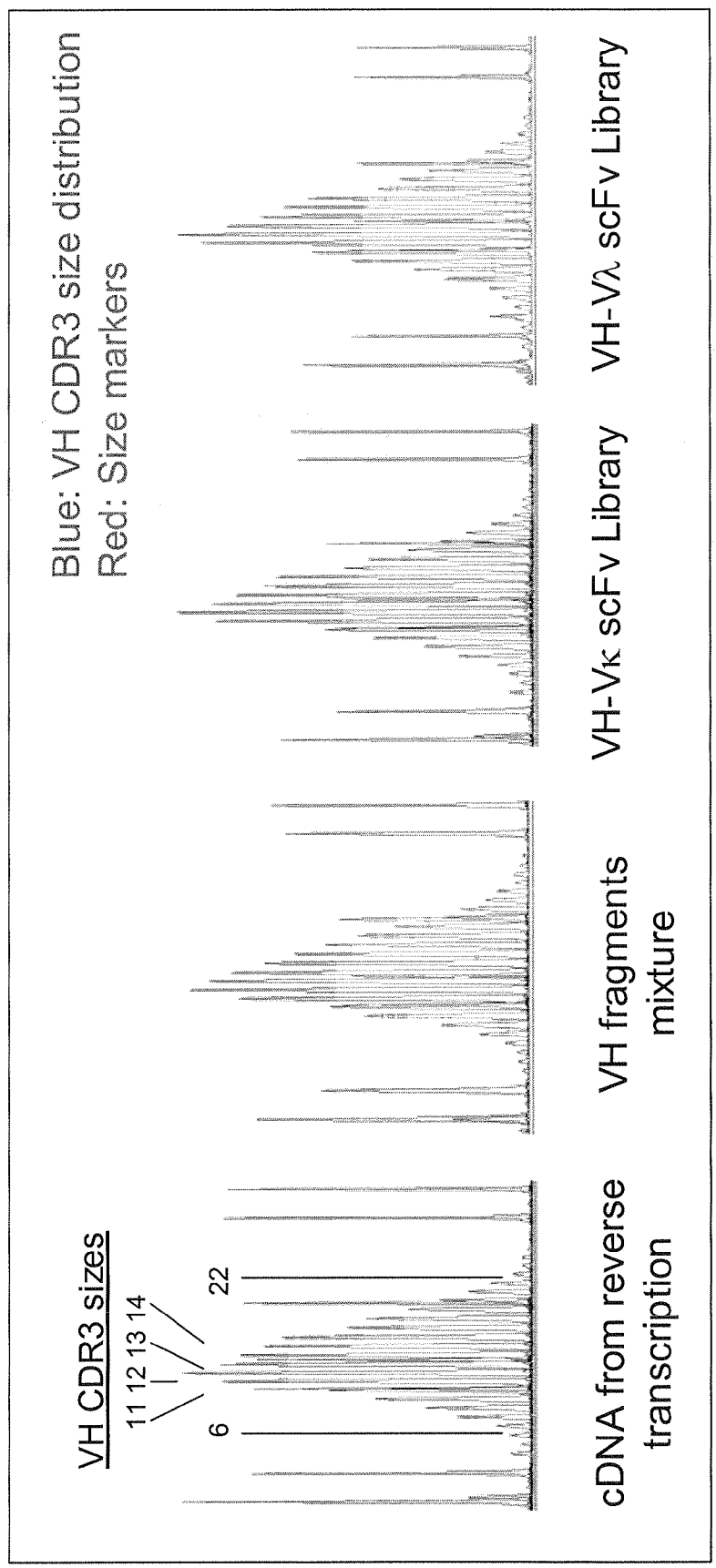
FIG. 31 depicts the quality control of VH-Vκ and VH-Vλ, libraries by spectratyping analysis in the constructed VH-Vλ, scFv library.

Spectratyping analysis of VH CDR3 size distribution is carried out on cDNA obtained from lymph node RNA by reverse transcription with mixture of reverse primers (see 10.1), on mixture of VH DNA fragments just prior to their assembly into scFv libraries, and on final VH-Vκ and VH-Vλ, scFv fragments (FIG. 31). As would be expected in a cDNA library with a high degree of diversity, the observed CDR3 sizes have a normal distribution and the majority fall in between 6 to 22 residues and centerin between 11 to 14 residues.

Conclusion

The selection of high quality human antibody leads is a prerequisite for successful therapeutic antibody drug development. In additional to a robust selection technology, the antibody library quality (source, diversity, and construction) greatly determines its usefulness to produce good leads. In this invention the mRNA from multiple donors are used to increase library diversity and highly specific PCR primers are designed to cover all antibody germline sequences such that all diversity within the donor collection can be captured. VH-Vκ and VH-Vλ, ScFv libraries are constructed separately to increase chances of selecting multiple antibodies leads from the same RNA source. Large diversity of both libraries is confirmed by spectratyping and by sequencing of multiple clones. Both libraries are used for PROfusion mRNA display selection against different targets.

Example 11

Sequencing Primers for Profusion Constructs

This Example provides the sequencing primers used for PROfusion constructs.

```
Forward primer for all scFv and VH libraries:
T7TMVUTR (SEQ ID NO: 1):
TAATACGACTCACTATAGGGACAATTACTATTTACAATTACA Forward primer for all Vκ and Vλ libraries:
VL-T7TMVTag3GS-Fwd (SEQ IN NO: 2):
TAATACGACTCACTATAGGGACAATTACTATTTACAATTACAGGCTTTGGAC

CATGGGGTCTGGCGGCGGAGGTAGCG

Reverse primers for all κ scFv and Vκ libraries:
Cκ1FLAGA20 (SEQ ID NO: 3):
TTTTTTTTTTTTTTTTTTTTAAATAGCGGATGCCTTGTCGTCGTCGTCCTTGTA

GTCGAAGACAGAT

Cκ2FLAGA20 (SEQ ID NO: 4):
TTTTTTTTTTTTTTTTTTTTAAATAGCGGATGCCTTGTCGTCGTCGTCCTTGTA

GTCGAAGACAGATGGT

Cκ3FLAGA20 (SEQ ID NO: 5):
TTTTTTTTTTTTTTTTTTTTAAATAGCGGATGCCTTGTCGTCGTCGTCCTTGTA

GTCGAAGACAGATGGTGCA

Cκ4FLAGA20 (SEQ ID NO: 6):
TTTTTTTTTTTTTTTTTTTTAAATAGCGGATGCCTTGTCGTCGTCGTCCTTGTA

GTCGAAGACAGATGGTGCAGCC

Cκ5FLAGA20 (SEQ ID NO: 7):
TTTTTTTTTTTTTTTTTTTTAAATAGCGGATGCCTTGTCGTCGTCGTCCTTGTA

GTCGAAGACAGATGGTGCAGCCACA

Reverse primers for all λ scFv and Vλ libraries:
CL1FLAGA20 (SEQ ID NO: 8):
TTTTTTTTTTTTTTTTTTTTAAATAGCGGATGCCTTGTCGTCGTCGTCCTTGTA

GTCAGTGACAGTG

CL2FLAGA20 (SEQ ID NO: 9):
TTTTTTTTTTTTTTTTTTTTAAATAGCGGATGCCTTGTCGTCGTCGTCCTTGTA

GTCAGTGACAGTGGGG
```

-continued

CL3FLAGA20 (SEQ ID NO: 10):
TTTTTTTTTTTTTTTTTTTTAAATAGCGGATGCCTTGTCGTCGTCGTCCTTGTA

GTCAGTGACAGTGGGGTTG

CL4FLAGA20 (SEQ ID NO: 11):
TTTTTTTTTTTTTTTTTTTTAAATAGCGGATGCCTTGTCGTCGTCGTCCTTGTA

GTCAGTGACAGTGGGGTTGGCC

CL5FLAGA20 (SEQ ID NO: 12):
TTTTTTTTTTTTTTTTTTTTAAATAGCGGATGCCTTGTCGTCGTCGTCCTTGTA

GTCAGTGACAGTGGGGTTGGCCTTG

Lib-GS-Rev (SEQ ID NO: 16): CGCTACCTCCGCCGCCAGAC

Reverse primer for all VH libraries:
VH-GSFLAGA20-Rev (SEQ ID NO: 13):
TTTTTTTTTTTTTTTTTTTTAAATAGCGGATGCTTTGTCATCATCATCTTTATA

ATCGCTACCTCCGCCGCCAGAC

Primers for synthesis of the first strand cDNA in reverse transcription:
Fcg:
FcγRev1 (SEQ ID NO: 43): AGTTCCACGACACC FcγRev2 (SEQ ID NO: 44): GAAGGTGTGCACG FcγRev3 (SEQ ID NO: 45): CCACGCTGCTGAG Fcm:
FcµRev1 (SEQ ID NO: 46): ACTTTGCACACCAC FcµRev2 (SEQ ID NO: 47): TTTGTTGCCGTTGG FcµRev3 (SEQ ID NO: 48): GGGAATTCTCACAGG Fcd:
FcδRev1 (SEQ ID NO: 49): GCTGCTTGTCATGT FcδRev2 (SEQ ID NO: 50): TGCCTTTGGAGACT FcδRev3 (SEQ ID NO: 51): GACCACGCATTTGT Cκ-RT Primers:
CκRev1 (SEQ ID NO: 52): TCCACCTTCCACTG CκRev2 (SEQ ID NO: 53): CAGGCACACAACAG CκRev3 (SEQ ID NO: 54): GAGTGTCACAGAGC CLRTPrimers
CλRev1 (SEQ ID NO: 55) GGGAACAGAGTGAC CλRev2 (SEQ ID NO: 56): GTGTGGCCTTGTTG CλRev3. (SEQ ID NO: 57): CCATCTGCCTTCCA Primers used for VH fragments amplification:
VH1/7LS (SEQ ID NO: 58): ATCCTCTTYTTGGTGGSAGC

VH1-46LS (SEQ ID NO: 59): GGTCTTCTGCTTGCTGGCTG

VH2LS (SEQ ID NO: 60): CCTGCTGCTGACCAYCCCTTC

VH3LS (SEQ ID NO: 61): GCTATTTTWVRAGGTGTCCARTGT

VH4LS (SEQ ID NO: 62): GCRGCTCCCAGATGGGTCCTG

VH5LS (SEQ ID NO: 63): ATGGGGTCAACCGCCATCCT

VH6LS (SEQ ID NO: 64): TGGGCCTCCCATGGGGTGTC

-continued

```
Primers used for nested VH-specific PCR:
VHPrimersTag2:
VH1Forward (SEQ ID NO: 69):
tttacaattacagtgttgcgaccatggAGGTGCAGCTGGTGCAGTCTGGRSCT VH2Forward (SEQ ID NO: 70):
tttacaattacagtgttgcgaccatggAGRTCACCTTGARGGAGTCTGGT VH3Forward (SEQ ID NO: 71):
tttacaattacagtgttgcgaccatggGAGGTGCAGCTGKTGGAGTCTSGRGGA VH4Forward (SEQ ID NO: 72):
tttacaattacagtgttgcgaccatggAGGTGCAGCTGCAGSAGTSSGGC VH5Forward (SEQ ID NO: 73):
tttacaattacagtgttgcgaccatggGAGGTGCAGCTGGTGCAGTCTGGAGCA VH6Forward (SEQ ID NO: 74):
tttacaattacagtgttgcgaccatggAGGTACAGCTGCAGCAGTCAG VH7Forward (SEQ ID NO: 75):
tttacaattacagtgttgcgaccatggAGGTGCAGCTGGTGCAATCTGGGT Primers used for Vκ fragments amplification:
T7TMVTag2 (SEQ ID NO: 80):
TAATACGACTCACTATAGGGACAATTACTATTTACAATTACAG TGTTGCGAC

Vκ1LS (SEQ ID NO: 81): GCTCCTGGGRCTYCTGC

Vκ2LS (SEQ ID NO: 82): CTYCTGGGGCTGCTAATG

Vκ3LS (SEQ ID NO: 83): CTCTGGCTCMCAGATACCAC

Vκ4LS (SEQ ID NO: 84): GGATCTCTGGTGCCTACGG

Vκ5LS (SEQ ID NO: 85): GGATCTCTGATACCAGGGCA

Vκ6LS (SEQ ID NO: 86): CTGGGTTCCAGCCTCCAG

Library Gly-Ser overlapping primers:
Lib-GS-Fwd (SEQ ID NO: 94): GTCTGGCGGCGGAGGTAGCG FLAG-A20.Rev (SEQ ID NO: 95):
TTTTTTTTTTTTTTTTTTTTAAATAGCGGATGCCTTGTCGTCGT

CGTCCTTGTAGTC

Primers used for Vλ fragments amplification:
VL1LS-1 (SEQ ID NO: 96): TCACTGTGCAGGGTCCTG

VL1LS-3 (SEQ ID NO: 97): TCACTGCACAGGGTCCTG

VL2LS-3 (SEQ ID NO: 98): TCAGGRCACAGGGTCCTG

VL2LS-4 (SEQ ID NO: 99): TCAGGGCACAGGATCCTG

VL3LS-2 (SEQ ID NO: 100): TGCATAGGTTCTGTGGTTTCTTCTG

VL3LS-3 (SEQ ID NO: 101): ACAGGHTCTGWGGCCTCCTATG

VL3LS-4 (SEQ ID NO: 102): TGCACAGGCTCTGTGACCTCCTATG

VL3LS-5 (SEQ ID NO: 103): TACACAGGCTCTATTGCCTCCTATG

VL4Cls-2 (SEQ ID NO: 104): CTTCATTTTCTCCACAGGTCTCTGTG

VL4abLS-2 (SEQ ID NO: 105): TCCACTGSACAGGGTCTCTCT

VL5LS (SEQ ID NO: 106): CACTGCACAGGTTCCCTC

VL6LS (SEQ ID NO: 107): CTGCACAGGTTCTTGGGC

VL7LS (SEQ ID NO: 108): CTCACTTGCTGCCCAGGG

VL8LS (SEQ ID NO: 109): GCTTATGGATCAGGAGTGGATTC

VL9LS (SEQ ID NO: 110): CACCCTCCTCAGTCTCCTC

VL10LS (SEQ ID NO: 111): CTCTGCAGTGTCAGTGGTC
```

```
Primers used for nested VH-specific PCR:
VHPrimersTag4:
VH1Forward (SEQ ID NO: 121):
tttacaattacagcttcttcaccatggAGGTGCAGCTGGTGCAGTCTGGRSCT VH2Forward (SEQ ID NO: 122):
tttacaattacagcttcttcaccatggAGRTCACCTTGARGGAGTCTGGT VH3Forward (SEQ ID NO: 123):
ttacaattacagcttcttcaccatgGAGGTGCAGCTGKTGGAGTCTSGRGGA VH4Forward (SEQ ID NO: 124):
tttacaattacagcttcttcaccatggAGGTGCAGCTGCAGSAGTSSGGC VH5Forward (SEQ ID NO: 125):
tttacaattacagcttcttcaccatggAGGTGCAGCTGGTGCAGTCTGGAGCA VH6Forward (SEQ ID NO: 126):
tttacaattacagcttcttcaccatggAGGTACAGCTGCAGCAGTCAG VH7Forward (SEQ ID NO: 127):
tttacaattacagcttcttcaccatggAGGTGCAGCTGGTGCAATCTGGGT JHReverse1/2 (SEQ ID NO: 128):
CGCTACCTCCGCCGCCAGACCCGCCTCCACCTGAGGAGACRGT

GACCAGGGTGC

JHReverse3 (SEQ ID NO: 129):
CGCTACCTCCGCCGCCAGACCCGCCTCCACCTGAAGAGACGGTG

ACCATTGTCC

JHReverse4/5 (SEQ ID NO: 130):
CGCTACCTCCGCCGCCAGACCCGCCTCCACCTGAGGAGACGGT

GACCAGGGTTC

JHReverse6 (SEQ ID NO: 131):
CGCTACCTCCGCCGCCAGACCCGCCTCCACCTGAGGAGACGGTG

ACCGTGGTCC

Primers used for Vλ fragments amplification:
VκPrimersV2:
Vκ1FwdV2 (SEQ ID NO: 134):
CAGCGGCGGTGGAGGGTCTGGCGGTGGCGGAAGTGACATCCRGWTGACCC

AGTCTCCWT

Vκ2FwdV2 (incl.L10ofVK3) (SEQ ID NO: 135):
CAGCGGCGGTGGAGGGTCTGGCGGTGGCGGAAGTGATATTGTGATGACYC

AGWCTCCAC

Vκ3FwdV2 (except L10) (SEQ ID NO: 136):
CAGCGGCGGTGGAGGGTCTGGCGGTGGCGGAAGTGAAATTGTGWTGACRC

AGTCTCCAGSCA

Vκ4/6FwdV2 (SEQ ID NO: 137):
CAGCGGCGGTGGAGGGTCTGGCGGTGGCGGAAGTGACATCGTGMTGACYC

AGTCTCCAGA

Vκ5FwdV2 (SEQ ID NO: 138):
CAGCGGCGGTGGAGGGTCTGGCGGTGGCGGAAGTGAAACGACACTCACGC

AGTCTCCAGCAT

Vκ6FwdV2 (SEQ ID NO: 139):
CAGCGGCGGTGGAGGGTCTGGCGGTGGCGGAAGTGATGTCGTGATGACAC

AGTCTCCAGCTT

T7-TMV-Seq (9970) (SEQ ID NO: 148): CTC ACT ATA GGG ACA ATT AC

T7TMVTag3 (SEQ ID NO: 149):
TAATACGACTCACTATAGGGACAATTACTATTTACAATTACAGGCTTTGGAC
```

-continued

T7TMVTag4 (SEQ ID NO: 150):
TAATACGACTCACTATAGGGACAATTACTATTTACAATTACAGCTTCTTCAC

T7TMVTag2s (SEQ ID NO: 151):
TAATACGACTCACTATAGGGACAATTACTATTTACAATTACAG TGTTGCG

T7TMVTag3s (SEQ ID NO: 152):
TAATACGACTCACTATAGGGACAATTACTATTTACAATTACAGGCTTTGG

T7TMVTag4s (SEQ ID NO: 132):
TAATACGACTCACTATAGGGACAATTACTATTTACAATTACAGCTTCTTC

T7TMVTag4L (SEQ ID NO: 153):
TAATACGACTCACTATAGGGACAATTACTATTTACAATTACA

GCTTCTTCACCATGG

TMVTag4L (SEQ ID NO: 154):
ACAATTACTATTTACAATTACAGCTTCTTCACCATGG

TMVTag4 (SEQ ID NO: 155): ACAATTACTATTTACAATTACAGCTTCTTCAC

TMVTag4s (SEQ ID NO: 156): ACAATTACTATTTACAATTACAGCTTCTTC phylflag3's (no poly A) (SEQ ID NO: 157): CCTTGTCGTCGTCGTCCTTGTAGTC VH-FLAGA20-Rev (FLAG is recoded to minimize X-priming with VL's FLAG
sequence) (SEQ ID NO: 158):
TTTTTTTTTTTTTTTTTTTAAATAGCGGATGCTTTGTCATCATCATCTTTATA

ATC

Primers to Make VH Domain Library with Cμ Spacer:
JH1/2Cm-Rev (SEQ ID NO: 159):
GGTTGGGGCGGATGCACTCCC<u>CTGAGGAGACRGTGACCAGGGTGC</u>

JH4/5Cm-Rev (SEQ ID NO: 160):
GGTTGGGGCGGATGCACTCCCCTGAGGAGACGGTGACCAGGGTTC

JH6Cm-Rev (SEQ ID NO: 161):
GGTTGGGGCGGATGCACTCCCCTGAGGAGACGGTGACCGTGG TCC

JH3Cm-Rev (SEQ ID NO: 162):
GGTTGGGGCGGATGCACTCCC<u>CTGAAGAGACGGTGACCATTG TCC</u>

JH1/2sRev (SEQ ID NO: 65): CTGAGGAGACRGTGACCAGGGTGC

JH4/5sRev (SEQ ID NO: 66): CTGAGGAGACGGTGACCAGGGTTC

JH6sRev (SEQ ID NO: 67): CTGAGGAGACGGTGACCGTGGTCC

JH3sRev (SEQ ID NO:68): CTGAAGAGACGGTGACCATTGTCC

Vκ Primers:
Vκ1 Forward (SEQ ID NO: 88):
GTCTGGCGGCGGAGGTAGCGGCGGTGGCGGATCG<u>GACATCCRGWTGACCCA</u>

<u>GTCTCCWT</u>

Vκ2 Forward (including L10 of Vκ3) (SEQ ID NO: 89):
GTCTGGCGGCGGAGGTAGCGGCGGTGGCGGATCG<u>GATATTGTGATGACYCA</u>

<u>GWCTCCAC</u>

Vκ3 Forward (except L10) (SEQ ID NO: 90):
CTGGCGGCGGAGGTAGCGGCGGTGGCGGATCG<u>GAAATTGTGWTGACRCAGT</u>

<u>CTCCAGSCA</u>

Vκ4/6 Forward (SEQ ID NO: 91):
GTCTGGCGGCGGAGGTAGCGGCGGTGGCGGATCG<u>GACATCGTGMTGACYCA</u>

<u>GTCTCCAGA</u>

Vκ5 For-NEW (SEQ ID NO: 92):
CTGGCGGCGGAGGTAGCGGCGGTGGCGGATCG<u>GAAACGACACTCACGCAGT</u>

CTCCAGCAT

Vκ6 For-NEW (SEQ ID NO: 93):
CTGGCGGCGGAGGTAGCGGCGGTGGCGGATCGGATGTCGTGATGACACAGT

CTCCAGCTT

Vκ5 Forward (SEQ ID NO: 168):
GTCTGGCGGCGGAGGTAGCGGCGGTGGCGGATCGGAAACGACACTCACGCA

GTCTC

Vκ6 Forward (SEQ ID NO: 169):
CTGGCGGCGGAGGTAGCGGCGGTGGCGGATCGGATGTCGTGATGACACAGT

CTCCAGCT

Cκ Reverse (SEQ ID NO: 14):
GTCGTCGTCGTCCTTGTAGTCGAAGACAGATGGTGCAGCCACAGTTCG

Cκ5 FLAGA20 (SEQ ID NO: 7):
TTTTTTTTTTTTTTTTTTTTAAATAGCGGATGCCTTGTCGTCGTCGTCCTTGTA

GTCGAAGACAGATGGTGCAGCCACA

Cκ-s Reverse primer: (SEQ ID NO: 87): GAAGACAGATGGTGCAGCCACAGTTCG

Cκ-Long-Reverse primer(SEQ ID NO: 170): Long Cκ Reverse Primer to add 7 A.A. before FLAG:
gtcgtcgtcgtccttgtagtcCTCATCAGATGGCGGGAAGATGAAGACAGATGGTGCAGC

CACAGTTCG

FLAG hCκ primers:
CκL4-FlagA20-Rev (SEQ ID NO: 171):
TTTTTTTTTTTTTTTTTTTTAAATAGCGGATGCCTTGTCGTCGTCGTCCTTGTA

GTCCTCATCAGATGGCGGGAAGAT

CκL3-FlagA20-Rev (SEQ ID NO: 172):
TTTTTTTTTTTTTTTTTTTTAAATAGCGGATGCCTTGTCGTCGTCGTCCTTGTA

GTCCTCATCAGATGGCGGGAA

CκL2-FlagA20-Rev (SEQ ID NO: 173):
TTTTTTTTTTTTTTTTTTTTAAATAGCGGATGCCTTGTCGTCGTCGTCCTTGTA

GTCCTCATCAGATGGCGG

CκL1-FlagA20-Rev (SEQ ID NO: 174):
TTTTTTTTTTTTTTTTTTTTAAATAGCGGATGCCTTGTCGTCGTCGTCCTTGTA

GTCCTCATCAGATGG

VL Primers:
VL1/10 Forward (SEQ ID NO: 175):
GTCTGGCGGCGGAGGTAGCGGCGGTGGCGGATCGCAGTCTGKGCTGACKCA

GCCRC

VL2 Forward (SEQ ID NO: 114):
GTCTGGCGGCGGAGGTAGCGGCGGTGGCGGATCGCAGTCTGCCCTGACTCA

GCCT

VL3 Forward-New (SEQ ID NO: 115):
GTCTGGCGGCGGAGGTAGCGGCGGTGGCGGATCGTCCTATGAGCTGACDCAG VL4ab Forward (SEQ ID NO: 116):
GTCTGGCGGCGGAGGTAGCGGCGGTGGCGGATCGCAGYTGTGCTGACTCA

ATC

VL4c Forward (SEQ ID NO: 117):
GTCTGGCGGCGGAGGTAGCGGCGGTGGCGGATCGCTGCCTGTGCTGACTCA

GCCCCCG

VL5/9 Forward (SEQ ID NO: 118):
GTCTGGCGGCGGAGGTAGCGGCGGTGGCGGATCGCAGCCTGTGCTGACTCA -continued

GCCRBCT

VL6 Forward (SEQ ID NO: 119):
GTCTGGCGGCGGAGGTAGCGGCGGTGGCGGATCGAATTTTATGCTGACTCA

GCCC

VL7/8 Forward (SEQ ID NO: 120):
GTCTGGCGGCGGAGGTAGCGGCGGTGGCGGATCGCAGRCTGTGGTGACYCA

GGAG

CJL Reverse (SEQ ID NO: 15):
GTCGTCGTCGTCCTTGTAGTCAGTGACAGTGGGGTTGGCCTTGGGCTGACCK

AGGACGGT

CJL-sReverse (SEQ ID NO: 112): GCCTTGGGCTGACCKAGGACGGT

VH Primers Tag3:
VH1FwdTag3 (SEQ ID NO: 176):
tttacaattacaGGCTTTGGaccatggAGGTGCAGCTGGTGCAGTCTGGRSCT VH2FwdTag3 (SEQ ID NO: 177):
tttacaattacaGGCTTTGGaccatggAGRTCACCTTGARGGAGTCTGGT VH3FwdTag3 (SEQ ID NO: 178):
tttacaattacaGGCTTTGGaccatggGAGGTGCAGCTGKTGGAGTCTSGR GGA VH4FwdTag3 (SEQ ID NO: 179):
tttacaattacaGGCTTTGGaccatggAGGTGCAGCTGCAGSAGTSSGGC VH5FwdTag3 (SEQ ID NO: 180):
tttacaattacaGGCTTTGGaccatggAGGTGCAGCTGGTGCAGTCTGGA GCA VH6FwdTag3 (SEQ ID NO: 181):
tttacaattacaGGCTTTGGaccatggAGGTACAGCTGCAGCAGTCAG VH7FwdTag3 (SEQ ID NO: 182):
TttacaattacaGGCTTTGGaccatggAGGTGCAGCTGGTGCAATCT GGGT VLPrimers:
VL1/10FwdV2 (SEQ ID NO: 183):
CAGCGGCGGTGGAGGGTCTGGCGGTGGCGGAAGTCAGTCTGKGCTGACKC

AGCCRC

VL2FwdV2 (SEQ ID NO: 184):
CAGCGGCGGTGGAGGGTCTGGCGGTGGCGGAAGTCAGTCTGCCCTGACTCA

GCCT

VL3FwdV2 (SEQ ID NO: 185):
CAGCGGCGGTGGAGGGTCTGGCGGTGGCGGAAGTTCCTATGAGCTGACDCAG

VL4abFwdV2 (SEQ ID NO: 186):
CAGCGGCGGTGGAGGGTCTGGCGGTGGCGGAAGTCAGCYTGTGCTGACTCA

ATC

VL4cFwdV2 (SEQ ID NO: 187):
CAGCGGCGGTGGAGGGTCTGGCGGTGGCGGAAGTCTGCCTGTGCTGACTCA

GCCCCCG

VL5/9FwdV2 (SEQ ID NO: 188):
CAGCGGCGGTGGAGGGTCTGGCGGTGGCGGAAGTCAGCCTGTGCTGACTCA

GCCRBCT

VL6FwdV2 (SEQ ID NO: 189):
CAGCGGCGGTGGAGGGTCTGGCGGTGGCGGAAGTAATTTTATGCTGACTCA

G CCC

VL7/8FwdV2 (SEQ ID NO: 190):
CAGCGGCGGTGGAGGGTCTGGCGGTGGCGGAAGTCAGRCTGTGGTGACYC

AGGAG

Lib-GSv2-Fwd (SEQ ID NO: 140): CAGCGGCGGTGGAGGGTCTG

Lib-GSv2-Rev (SEQ ID NO: 133): CAGACCCTCCACCGCCGCTG

JH1/2RevV2 (SEQ ID NO: 128):
cagaccctccaccgccgctgccgcctccacCTGAGGAGACRGTGACCAGGGTGC JH4/5RevV2 (SEQ ID NO: 130):
cagaccctccaccgccgctgccgcctccacCTGAGGAGACGGTGACCAGGGTTC JH6RevV2 (SEQ ID NO: 131):
cagaccctccaccgccgctgccgcctccacCTGAGGAGACGGTGACCGTGGTCC JH3RevV2 (SEQ ID NO: 129):
cagaccctccaccgccgctgccgcctccacCTGAAGAGACGGTGACCATTGTCC Library GlySer linker v2:
Library GS Fwd:
C AGC GGC GGT GGA GGG TCT G -----> (SEQ ID NO: 145)
TCC TCA GGT GGA GGC GGC AGC GGC GGT GGA GGG TCT GGC GGT GGC

GGA AGT (SEQ ID NO: 146)

AGG AGT CCA CCT CCG CCG TCG CCG CCA CCT CCC AGA CCG CCA CCG

CCT TCA (SEQ ID NO: 147)

Library GS Rev: <----- G TCG CCG CCA CCT CCC AGA C (SEQ ID NO: 163)
S S G G G G S G G G G S G GG G S (SEQ ID NO: 164)
Overlapping during PCR
VH3 FR1: CAG CTG GTG GAG TCT GGG GGA GGC TTG GTC CAG CCT GGG

GGG TTC (SEQ ID NO: 165)

TCC TCA GGT GGA GGC GGC AGC GGC GGT GGA GGG TCT G (SEQ ID NO: 166)

G TCG CCG CCA CCT CCC AGA CCG CCA CCG CCT TCA (SEQ ID NO: 167)

(for Vk3, Vk6) <-----CG CCG CCA CCT CCC AGA CCG CCA CCG

CCT TCA (SEQ ID NO: 212)

Primers with New Tag for Human Tonsil Libraries
VH PrimersTag5:
VH1FwdTag5 (SEQ ID NO: 191):
tttacaattacaGTGTCTGTaccatggAGGTGCAGCTGGTGCAGTCTGGR SCT VH2FwdTag5 (SEQ ID NO: 192):
tttacaattacaGTGTCTGTaccatggAGRTCACCTTGARGGAGTC TGGT VH3FwdTag5 (SEQ ID NO: 193):
tttacaattacaGTGTCTGTaccatggAGGTGCAGCTGKTGGAGTCTSGR GGA VH4FwdTag5 (SEQ ID NO: 194):
tttacaattacaGTGTCTGTaccatggAGGTGCAGCTGCAGSAGTSSGGC VH5FwdTag5 (SEQ ID NO: 195):
tttacaattacaGTGTCTGTaccatggAGGTGCAGCTGGTGCAGTCTGGA GCA VH6FwdTag5 (SEQ ID NO: 196):
tttacaattacaGTGTCTGTaccatggAGGTACAGCTGCAGCAGTCAG VH7FwdTag5 (SEQ ID NO: 197):
TttacaattacaGTGTCTGTaccatggAGGTGCAGCTGGTGCAATCTGGGT Primers with New Tag for Human Bone Marrow Libraries
VHPrimersTag6:
VH1FwdTag6 (SEQ ID NO: 198):
tttacaattacaGTTTGGCTaccatggAGGTGCAGCTGGTGCAGTCTGGRS CT VH2FwdTag6 (SEQ ID NO: 199):
tttacaattacaGTTTGGCTaccatggAGRTCACCTTGARGGAGTCTGGT VH3FwdTag6 (SEQ ID NO: 200):
tttacaattacaGTTTGGCTCaccatggAGGTGCAGCTGKTGGAGTCTSG RGGA VH4FwdTag6 (SEQ ID NO: 201):
tttacaattacaGTTTGGCTaccatggAGGTGCAGCTGCAGSAGTSSGGC VH5FwdTag6 (SEQ ID NO: 202):
tttacaattacaGTTTGGCTaccatgGAGGTGCAGCTGGTGCAGTCTGGA GCA VH6FwdTag6 (SEQ ID NO: 203):
tttacaattacaGTTTGGCTaccatggAGGTACAGCTGCAGCAGTCAG VH7FwdTag6 (SEQ ID NO: 204):
TttacaattacaGTTTGGCTaccatggAGGTGCAGCTGGTGCAATCTGG GT Reamplifying Tag5 Forward Primers
TMVTag5s (SEQ ID NO: 205): ACAATTACTATTTACAATTACAGTGTCTGT TMVTag6s (SEQ ID NO: 206): ACAATTACTATTTACAATTACAGTTTGGCT TMVTag5 (SEQ ID NO: 207): ACAATTACTATTTACAATTACAGTGTCTGTacc TMVTag6 (SEQ ID NO: 208): ACAATTACTATTTACAATTACAGTTTGGCTacc T7TMVTag5s (SEQ ID NO: 209):
TAATACGACTCACTATAGGGACAATTACTATTT ACA AT TA CAGTGTCTGT T7TMVTag6s (SEQ ID NO: 210):
TAATACGACTCACTATAGGGACAATTACTATTTACAATTAC AGTTTGGCT

INCORPORATION BY REFERENCE

The contents of all cited references (including literature references, patents, patent applications, and websites) that may be cited throughout this application are hereby expressly incorporated by reference in their entirety, as are the references cited therein. The practice of the present invention will employ, unless otherwise indicated, conventional techniques of immunology, molecular biology and cell biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

The invention claimed is:

1. A method of producing a polynucleotide library for expression of single chain antibodies (scFv) comprising:
   providing a polynucleotide composition, wherein at least a portion of the polynucleotides in said composition comprise at least one open reading frame encoding an antibody variable domain; and,
   amplifying a plurality of polynucleotides encoding antibody variable domains with one or more oligonucleotides comprising the oligonucleotide sequence(s) of SEQ ID NO: 133 or SEQ ID NO: 140, thereby producing a polynucleotide library.

2. The method of claim 1, wherein the one or more oligonucleotide(s) are selected from the group consisting of SEQ ID NO: 134, 135, 136, 137, 138, 139, 140, 145, 146, 166, 183, 184, 185, 186, 187, 188, 189 and 190, or combinations thereof.

3. The method of claim 1, wherein the one or more oligonucleotide(s) are selected from the group consisting of SEQ ID NOs 133, 141, 142, 143, 144, 147, 163 and 167, or combinations thereof.

4. The method of claim 1, said library comprising a repertoire of sequences encoding heavy chain variable domains and light chain variable domains, wherein each member of said library contains an open reading frame comprising a heavy chain variable domain, a light chain variable domain, and a linker region.

5. The method of claim 4, wherein the linker region encodes less than 20 amino acids.

6. The method of claim 4, wherein the linker region encodes 15 amino acids.

7. The method of claim 4, wherein each member of said library further comprises a promoter operably linked to the open reading frame.

8. The method of claim 7, wherein said promoter is a promoter selected from the group consisting of T7, SP6, and T3.

9. The method of claim 8, wherein said promoter is a T7 promoter.

10. The method of claim 4, wherein each member of said library further comprises a 5' untranslated region (5'UTR) capable of enhancing transcription of a gene to which it is operably linked.

11. The method of claim 10, wherein said 5'UTR is a Tobacco Mosaic Virus 5'UTR or active fragment thereof.

12. The method of claim 4, wherein each member of said library further comprises a polyadenine sequence.

13. The method of claim 4, wherein each member of said library further comprises a nucleic acid barcode.

14. The method of claim 13, wherein said nucleic acid barcode comprises 8 nucleotides.

15. The method of claim 4, wherein each member of said library further comprises a nucleic acid sequence encoding an epitope tag.

16. The method of claim 15, wherein said nucleic acid sequence is part of the linker region of the scFv.

17. The method of claim 4, wherein each member of said library further comprises a nucleic acid sequence encoding an antibody constant region or fragment thereof.

18. The method of claim 4, wherein each member of said library further comprises a ribosome pause sequence.

19. The method of claim 4, wherein each member of said library further comprises a peptide acceptor.

20. The method of claim 19, wherein the peptide acceptor is covalently attached via a linker comprising a Psoralen C6 molecule.

21. The method of claim 20, wherein the linker is 5' (Psoralen C6) 2'Ome (U AGC GGA UGC) (SEQ ID NO: 211) XXX XXX CC (Puromycin), wherein X is a triethylene glycol linker or PEG-150 and CC is a DNA backbone.

22. An oligonucleotide comprising the oligonucleotide sequence of SEQ ID NO: 133.

23. The oligonucleotide of claim 22, wherein the oligonucleotide comprises the oligonucleotide sequence of SEQ ID NO: 141.

24. The oligonucleotide of claim 22, wherein the oligonucleotide comprises the oligonucleotide sequence of SEQ ID NO: 142.

25. The oligonucleotide of claim 22, wherein the oligonucleotide comprises the oligonucleotide sequence of SEQ ID NO: 143.

26. The oligonucleotide of claim 22, wherein the oligonucleotide comprises the oligonucleotide sequence of SEQ ID NO: 144.

27. The oligonucleotide of claim 22, wherein the oligonucleotide comprises the oligonucleotide sequence of SEQ ID NO: 147.

28. The oligonucleotide of claim 22, wherein the oligonucleotide comprises the oligonucleotide sequence of SEQ ID NO: 167.

29. An oligonucleotide comprising the oligonucleotide sequence of SEQ ID NO: 140.

30. The oligonucleotide of claim 29, wherein the oligonucleotide comprises the oligonucleotide sequence of SEQ ID NO: 134.

31. The oligonucleotide of claim 29, wherein the oligonucleotide comprises the oligonucleotide sequence of SEQ ID NO: 135.

32. The oligonucleotide of claim 29, wherein the oligonucleotide comprises the oligonucleotide sequence of SEQ ID NO: 136.

33. The oligonucleotide of claim 29, wherein the oligonucleotide comprises the oligonucleotide sequence of SEQ ID NO: 137.

34. The oligonucleotide of claim 29, wherein the oligonucleotide comprises the oligonucleotide sequence of SEQ ID NO: 138.

35. The oligonucleotide of claim 29, wherein the oligonucleotide comprises the oligonucleotide sequence of SEQ ID NO: 139.

36. The oligonucleotide of claim 29, wherein the oligonucleotide comprises the oligonucleotide sequence of SEQ ID NO: 146.

37. The oligonucleotide of claim 29, wherein the oligonucleotide comprises the oligonucleotide sequence of SEQ ID NO: 166.

38. The oligonucleotide of claim 29, wherein the oligonucleotide comprises the oligonucleotide sequence of SEQ ID NO: 183.

39. The oligonucleotide of claim 29, wherein the oligonucleotide comprises the oligonucleotide sequence of SEQ ID NO: 184.

40. The oligonucleotide of claim 29, wherein the oligonucleotide comprises the oligonucleotide sequence of SEQ ID NO: 185.

41. The oligonucleotide of claim 29, wherein the oligonucleotide comprises the oligonucleotide sequence of SEQ ID NO: 186.

42. The oligonucleotide of claim 29, wherein the oligonucleotide comprises the oligonucleotide sequence of SEQ ID NO: 187.

43. The oligonucleotide of claim 29, wherein the oligonucleotide comprises the oligonucleotide sequence of SEQ ID NO: 188.

44. The oligonucleotide of claim 29, wherein the oligonucleotide comprises the oligonucleotide sequence of SEQ ID NO: 189.

45. The oligonucleotide of claim 29, wherein the oligonucleotide comprises the oligonucleotide sequence of SEQ ID NO: 190.

* * * * *

SEQUENCE LISTING

<160> NUMBER OF SEQ ID NOS: 212

<210> SEQ ID NO 1
<211> LENGTH: 42
<212> TYPE: DNA
<213> ORGANISM: Artificial Sequence
<220> FEATURE:
<223> OTHER INFORMATION: Synthetic oligonucleotide: T7TMVUTR

<400> SEQUENCE: 1
taatacgact cactataggg acaattacta tttacaatta ca      42

<210> SEQ ID NO 2
<211> LENGTH: 78
<212> TYPE: DNA
<213> ORGANISM: Artificial Sequence
<220> FEATURE:
<223> OTHER INFORMATION: Synthetic oligonucleotide: VL-T7TMVTag3GS-Fwd

<400> SEQUENCE: 2
taatacgact cactataggg acaattacta tttacaatta caggctttgg accatggggt      60
ctggcggcgg aggtagcg      78

<210> SEQ ID NO 3
<211> LENGTH: 67
<212> TYPE: DNA
<213> ORGANISM: Artificial Sequence

```
<220> FEATURE:
<223> OTHER INFORMATION: Synthetic oligonucleotide: C(kappa)1FLAGA20

<400> SEQUENCE: 3
tttttttttt tttttttttt aaatagcgga tgccttgtcg tcgtcgtcct tgtagtcgaa     60
gacagat                                                              67

<210> SEQ ID NO 4
<211> LENGTH: 70
<212> TYPE: DNA
<213> ORGANISM: Artificial Sequence
<220> FEATURE:
<223> OTHER INFORMATION: Synthetic oligonucleotide: C(kappa)2FLAGA20

<400> SEQUENCE: 4
tttttttttt tttttttttt aaatagcgga tgccttgtcg tcgtcgtcct tgtagtcgaa     60
gacagatggt                                                           70

<210> SEQ ID NO 5
<211> LENGTH: 73
<212> TYPE: DNA
<213> ORGANISM: Artificial Sequence
<220> FEATURE:
<223> OTHER INFORMATION: Synthetic oligonucleotide: C(kappa)3FLAGA20

<400> SEQUENCE: 5
tttttttttt tttttttttt aaatagcgga tgccttgtcg tcgtcgtcct tgtagtcgaa     60
gacagatggt gca                                                       73

<210> SEQ ID NO 6
<211> LENGTH: 76
<212> TYPE: DNA
<213> ORGANISM: Artificial Sequence
<220> FEATURE:
<223> OTHER INFORMATION: Synthetic oligonucleotide: C(kappa)4FLAGA20

<400> SEQUENCE: 6
tttttttttt tttttttttt aaatagcgga tgccttgtcg tcgtcgtcct tgtagtcgaa     60
gacagatggt gcagcc                                                    76

<210> SEQ ID NO 7
<211> LENGTH: 79
<212> TYPE: DNA
<213> ORGANISM: Artificial Sequence
<220> FEATURE:
<223> OTHER INFORMATION: Synthetic oligonucleotide: C(kappa)5FLAGA20

<400> SEQUENCE: 7
tttttttttt tttttttttt aaatagcgga tgccttgtcg tcgtcgtcct tgtagtcgaa     60
gacagatggt gcagccaca                                                 79

<210> SEQ ID NO 8
<211> LENGTH: 67
<212> TYPE: DNA
<213> ORGANISM: Artificial Sequence
<220> FEATURE:
<223> OTHER INFORMATION: Synthetic oligonucleotide: CL1FLAGA20

<400> SEQUENCE: 8
tttttttttt tttttttttt aaatagcgga tgccttgtcg tcgtcgtcct tgtagtcagt     60
gacagtg                                                              67
```

<210> SEQ ID NO 9
<211> LENGTH: 70
<212> TYPE: DNA
<213> ORGANISM: Artificial Sequence
<220> FEATURE:
<223> OTHER INFORMATION: Synthetic oligonucleotide: CL2FLAGA20

<400> SEQUENCE: 9
tttttttttt tttttttttt aaatagcgga tgccttgtcg tcgtcgtcct tgtagtcagt    60
gacagtgggg                                                          70

<210> SEQ ID NO 10
<211> LENGTH: 73
<212> TYPE: DNA
<213> ORGANISM: Artificial Sequence
<220> FEATURE:
<223> OTHER INFORMATION: Synthetic oligonucleotide: CL3FLAGA20

<400> SEQUENCE: 10
tttttttttt tttttttttt aaatagcgga tgccttgtcg tcgtcgtcct tgtagtcagt    60
gacagtgggg ttg                                                      73

<210> SEQ ID NO 11
<211> LENGTH: 76
<212> TYPE: DNA
<213> ORGANISM: Artificial Sequence
<220> FEATURE:
<223> OTHER INFORMATION: Synthetic oligonucleotide: CL4FLAGA20

<400> SEQUENCE: 11
tttttttttt tttttttttt aaatagcgga tgccttgtcg tcgtcgtcct tgtagtcagt    60
gacagtgggg ttggcc                                                   76

<210> SEQ ID NO 12
<211> LENGTH: 79
<212> TYPE: DNA
<213> ORGANISM: Artificial Sequence
<220> FEATURE:
<223> OTHER INFORMATION: Synthetic oligonucleotide: CL5FLAGA20

<400> SEQUENCE: 12
tttttttttt tttttttttt aaatagcgga tgccttgtcg tcgtcgtcct tgtagtcagt    60
gacagtgggg ttggccttg                                                79

<210> SEQ ID NO 13
<211> LENGTH: 76
<212> TYPE: DNA
<213> ORGANISM: Artificial Sequence
<220> FEATURE:
<223> OTHER INFORMATION: Synthetic oligonucleotide: VH-GSFLAGA20-Rev

<400> SEQUENCE: 13
tttttttttt tttttttttt aaatagcgga tgctttgtca tcatcatctt tataatcgct    60
acctccgccg ccagac                                                   76

<210> SEQ ID NO 14
<211> LENGTH: 48
<212> TYPE: DNA
<213> ORGANISM: Artificial Sequence
<220> FEATURE:
<223> OTHER INFORMATION: Synthetic oligonucleotide: C(kappa) Reverse

<400> SEQUENCE: 14

```
gtcgtcgtcg tccttgtagt cgaagacaga tggtgcagcc acagttcg                48

<210> SEQ ID NO 15
<211> LENGTH: 60
<212> TYPE: DNA
<213> ORGANISM: Artificial Sequence
<220> FEATURE:
<223> OTHER INFORMATION: Synthetic oligonucleotide: CJL Reverse

<400> SEQUENCE: 15
gtcgtcgtcg tccttgtagt cagtgacagt ggggttggcc ttgggctgac ckaggacggt    60

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide: Lib-GS-Rev

<400> SEQUENCE: 16
cgctacctcc gccgccagac                                                20

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide: 6-FAM-PanVHFR3-Fwd

<400> SEQUENCE: 17
gacacggccg tgtattactg t                                              21

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide: PanJH-Rev

<400> SEQUENCE: 18
gctgaggaga cggtgacc                                                  18

<210> SEQ ID NO 19
<211> LENGTH: 70
<212> TYPE: DNA
<213> ORGANISM: Artificial Sequence
<220> FEATURE:
<223> OTHER INFORMATION: Synthetic oligonucleotide: T7-MAK195VH-Fwd

<400> SEQUENCE: 19
taatacgact cactataggg acaattacta tttacaatta caccatggag gtgcagctga    60
aggagtcagg                                                           70

<210> SEQ ID NO 20
<211> LENGTH: 68
<212> TYPE: DNA
<213> ORGANISM: Artificial Sequence
<220> FEATURE:
<223> OTHER INFORMATION: Synthetic oligonucleotide: MAK195VHGS-Rev

<400> SEQUENCE: 20
cgatccgcca ccgccagagc cacctccgcc tgaaccgcct ccacctgcag agacagtgac    60
cagagtcc                                                             68
```

<210> SEQ ID NO 21
<211> LENGTH: 67
<212> TYPE: DNA
<213> ORGANISM: Artificial Sequence
<220> FEATURE:
<223> OTHER INFORMATION: Synthetic oligonucleotide: MAK195VLGS-Fwd

<400> SEQUENCE: 21
ggtggaggcg gttcaggcgg aggtggctct ggcggtggcg gatcggacat tgtgatgacc    60
cagtctc                                                             67

<210> SEQ ID NO 22
<211> LENGTH: 45
<212> TYPE: DNA
<213> ORGANISM: Artificial Sequence
<220> FEATURE:
<223> OTHER INFORMATION: Synthetic oligonucleotide: MAK195VL-Rev

<400> SEQUENCE: 22
gatggtgcag ccaccgtacg ttttatttcc aactttgtcc ccgag                   45

<210> SEQ ID NO 23
<211> LENGTH: 70
<212> TYPE: DNA
<213> ORGANISM: Artificial Sequence
<220> FEATURE:
<223> OTHER INFORMATION: Synthetic oligonucleotide: T7TMVUTR-17/9 VH-1
      Fwd

<400> SEQUENCE: 23
ggacaattac tatttacaat tacaccatgg aagtgcagct ggtggaaagc ggcggcgatc    60
tggtgaaacc                                                          70

<210> SEQ ID NO 24
<211> LENGTH: 70
<212> TYPE: DNA
<213> ORGANISM: Artificial Sequence
<220> FEATURE:
<223> OTHER INFORMATION: Synthetic oligonucleotide: 17/9 VH-2 Rev

<400> SEQUENCE: 24
gctgctaaag ctaaagccgc tcgccgcgca gctcagtttc aggctgccgc ccggtttcac    60
cagatcgccg                                                          70

<210> SEQ ID NO 25
<211> LENGTH: 70
<212> TYPE: DNA
<213> ORGANISM: Artificial Sequence
<220> FEATURE:
<223> OTHER INFORMATION: Synthetic oligonucleotide: 17/9 VH-3 Fwd

<400> SEQUENCE: 25
ggctttagct ttagcagcta tggcatgagc tgggtgcgcc agaccccgga taaacgcctg    60
gaatgggtgg                                                          70

<210> SEQ ID NO 26
<211> LENGTH: 70
<212> TYPE: DNA
<213> ORGANISM: Artificial Sequence
<220> FEATURE:
<223> OTHER INFORMATION: Synthetic oligonucleotide: 17/9 VH-4 Rev

<400> SEQUENCE: 26
gcctttcacg ctatccggat aataggtata gccgccgccg ttgctaatgg tcgccaccca    60
ttccaggcgt                                                          70

<210> SEQ ID NO 27
<211> LENGTH: 69
<212> TYPE: DNA
<213> ORGANISM: Artificial Sequence
<220> FEATURE:
<223> OTHER INFORMATION: Synthetic oligonucleotide: 17/9 VH-5 Fwd

<400> SEQUENCE: 27
ccggatagcg tgaaaggccg ctttaccatt agccgcgata cgcgaaaaa caccctgtat     60 ctgcagatg                                                           69

<210> SEQ ID NO 28
<211> LENGTH: 70
<212> TYPE: DNA
<213> ORGANISM: Artificial Sequence
<220> FEATURE:
<223> OTHER INFORMATION: Synthetic oligonucleotide: 17/9 VH-6 Rev

<400> SEQUENCE: 28
gttcgcggcg cgcgcaataa tacatcgcgc tatcttcgct tttcaggctg ctcatctgca    60
gatacagggt                                                          70

<210> SEQ ID NO 29
<211> LENGTH: 70
<212> TYPE: DNA
<213> ORGANISM: Artificial Sequence
<220> FEATURE:
<223> OTHER INFORMATION: Synthetic oligonucleotide: 17/9 VH-7 Fwd

<400> SEQUENCE: 29
attgcgcgcg ccgcgaacgc tatgatgaaa acggctttgc gtattggggc cagggcaccc    60
tggtgaccgt                                                          70

<210> SEQ ID NO 30
<211> LENGTH: 70
<212> TYPE: DNA
<213> ORGANISM: Artificial Sequence
<220> FEATURE:
<223> OTHER INFORMATION: Synthetic oligonucleotide: 17/9 VH-8 GS Rev

<400> SEQUENCE: 30
cgatccgcca ccgccgctgc cacctccgcc tgaaccgcct ccaccgcgc tcacggtcac    60 cagggtgccc                                                          70

<210> SEQ ID NO 31
<211> LENGTH: 70
<212> TYPE: DNA
<213> ORGANISM: Artificial Sequence
<220> FEATURE:
<223> OTHER INFORMATION: Synthetic oligonucleotide: GS-17/9 VL-1 Fwd

<400> SEQUENCE: 31
agcggcggtg gcggatcgga tattgtgatg acccagagcc cgagcagcct gaccgtgacc    60
gcgggcgaaa                                                          70

<210> SEQ ID NO 32
<211> LENGTH: 70

<212> TYPE: DNA
<213> ORGANISM: Artificial Sequence
<220> FEATURE:
<223> OTHER INFORMATION: Synthetic oligonucleotide: 17/9 VL-2 Rev

<400> SEQUENCE: 32
tgtttgccgc tgttaaacag gctctggctg ctggtgcagc tcatggtcac tttttcgccc    60
gcggtcacgg    70

<210> SEQ ID NO 33
<211> LENGTH: 70
<212> TYPE: DNA
<213> ORGANISM: Artificial Sequence
<220> FEATURE:
<223> OTHER INFORMATION: Synthetic oligonucleotide: 17/9 VL-3 Fwd

<400> SEQUENCE: 33
gtttaacagc ggcaaacaga aaaactatct gacctggtat cagcagaaac cgggccagcc    60
gccgaaagtg    70

<210> SEQ ID NO 34
<211> LENGTH: 70
<212> TYPE: DNA
<213> ORGANISM: Artificial Sequence
<220> FEATURE:
<223> OTHER INFORMATION: Synthetic oligonucleotide: 17/9 VL-4 Rev

<400> SEQUENCE: 34
cggtaaagcg atccggcacg ccgctttcgc gggtgctcgc ccaataaatc agcactttcg    60
gcggctggcc    70

<210> SEQ ID NO 35
<211> LENGTH: 70
<212> TYPE: DNA
<213> ORGANISM: Artificial Sequence
<220> FEATURE:
<223> OTHER INFORMATION: Synthetic oligonucleotide: 17/9 VL-5 Fwd

<400> SEQUENCE: 35
tgccggatcg ctttaccggc agcggcagcg gcaccgattt taccctgacc attagcagcg    60
tgcaggcgga    70

<210> SEQ ID NO 36
<211> LENGTH: 70
<212> TYPE: DNA
<213> ORGANISM: Artificial Sequence
<220> FEATURE:
<223> OTHER INFORMATION: Synthetic oligonucleotide: 17/9 VL-6 Rev

<400> SEQUENCE: 36
aaaggtcagc gggttgctat aatcgttctg gcaataatac accgccagat cttccgcctg    60
cacgctgcta    70

<210> SEQ ID NO 37
<211> LENGTH: 70
<212> TYPE: DNA
<213> ORGANISM: Artificial Sequence
<220> FEATURE:
<223> OTHER INFORMATION: Synthetic oligonucleotide: 17/9 VL-7 Fwd

<400> SEQUENCE: 37
agcaacccgc tgacctttgg cggcggcacc aaactggaaa tgaaacgtac ggtggctgca    60
ccatctgtct    70

<210> SEQ ID NO 38
<211> LENGTH: 64
<212> TYPE: DNA
<213> ORGANISM: Artificial Sequence
<220> FEATURE:
<223> OTHER INFORMATION: Synthetic oligonucleotide: 17/9 VL-8 Flag Rev

<400> SEQUENCE: 38
ttaaatagcg gatgccttgt cgtcgtcgtc cttgtagtcg atgaagacag atggtgcagc    60
cacc    64

<210> SEQ ID NO 39
<211> LENGTH: 60
<212> TYPE: DNA
<213> ORGANISM: Artificial Sequence
<220> FEATURE:
<223> OTHER INFORMATION: Synthetic oligonucleotide: 17_9-tag1

<400> SEQUENCE: 39
taatacgact cactataggg acaattacta tttacaatta cagcgtgggt accatggaag    60

<210> SEQ ID NO 40
<211> LENGTH: 60
<212> TYPE: DNA
<213> ORGANISM: Artificial Sequence
<220> FEATURE:
<223> OTHER INFORMATION: Synthetic oligonucleotide: 17_9-tag2

<400> SEQUENCE: 40
taatacgact cactataggg acaattacta tttacaatta cagtgttgcg accatggaag    60

<210> SEQ ID NO 41
<211> LENGTH: 60
<212> TYPE: DNA
<213> ORGANISM: Artificial Sequence
<220> FEATURE:
<223> OTHER INFORMATION: Synthetic oligonucleotide: 17_9-tag3

<400> SEQUENCE: 41
taatacgact cactataggg acaattacta tttacaatta caggctttgg accatggaag    60

<210> SEQ ID NO 42
<211> LENGTH: 60
<212> TYPE: DNA
<213> ORGANISM: Artificial Sequence
<220> FEATURE:
<223> OTHER INFORMATION: Synthetic oligonucleotide: 17_9-tag4

<400> SEQUENCE: 42
taatacgact cactataggg acaattacta tttacaatta cagcttcttc accatggaag    60

<210> SEQ ID NO 43
<211> LENGTH: 14
<212> TYPE: DNA
<213> ORGANISM: Artificial Sequence
<220> FEATURE:
<223> OTHER INFORMATION: Synthetic oligonucleotide: Fc(gamma)Rev1

<400> SEQUENCE: 43
agttccacga cacc    14

<210> SEQ ID NO 44
<211> LENGTH: 13
<212> TYPE: DNA
<213> ORGANISM: Artificial Sequence

```
<220> FEATURE:
<223> OTHER INFORMATION: Synthetic oligonucleotide: Fc(gamma)Rev2

<400> SEQUENCE: 44
gaaggtgtgc acg                                                    13

<210> SEQ ID NO 45
<211> LENGTH: 13
<212> TYPE: DNA
<213> ORGANISM: Artificial Sequence
<220> FEATURE:
<223> OTHER INFORMATION: Synthetic oligonucleotide: Fc(gamma)Rev3

<400> SEQUENCE: 45
ccacgctgct gag                                                    13

<210> SEQ ID NO 46
<211> LENGTH: 14
<212> TYPE: DNA
<213> ORGANISM: Artificial Sequence
<220> FEATURE:
<223> OTHER INFORMATION: Synthetic oligonucleotide: Fc(mu)Rev1

<400> SEQUENCE: 46
actttgcaca ccac                                                   14

<210> SEQ ID NO 47
<211> LENGTH: 14
<212> TYPE: DNA
<213> ORGANISM: Artificial Sequence
<220> FEATURE:
<223> OTHER INFORMATION: Synthetic oligonucleotide: Fc(mu)Rev2

<400> SEQUENCE: 47
tttgttgccg ttgg                                                   14

<210> SEQ ID NO 48
<211> LENGTH: 15
<212> TYPE: DNA
<213> ORGANISM: Artificial Sequence
<220> FEATURE:
<223> OTHER INFORMATION: Synthetic oligonucleotide: Fc(mu)Rev3

<400> SEQUENCE: 48
gggaattctc acagg                                                  15

<210> SEQ ID NO 49
<211> LENGTH: 14
<212> TYPE: DNA
<213> ORGANISM: Artificial Sequence
<220> FEATURE:
<223> OTHER INFORMATION: Synthetic oligonucleotide: Fc(delta)Rev1

<400> SEQUENCE: 49
gctgcttgtc atgt                                                   14

<210> SEQ ID NO 50
<211> LENGTH: 14
<212> TYPE: DNA
<213> ORGANISM: Artificial Sequence
<220> FEATURE:
<223> OTHER INFORMATION: Synthetic oligonucleotide: Fc(delta)Rev2

<400> SEQUENCE: 50
tgcctttgga gact                                                   14
```

<210> SEQ ID NO 51
<211> LENGTH: 14
<212> TYPE: DNA
<213> ORGANISM: Artificial Sequence
<220> FEATURE:
<223> OTHER INFORMATION: Synthetic oligonucleotide: Fc(delta)Rev3

<400> SEQUENCE: 51
gaccacgcat ttgt                                                        14

<210> SEQ ID NO 52
<211> LENGTH: 14
<212> TYPE: DNA
<213> ORGANISM: Artificial Sequence
<220> FEATURE:
<223> OTHER INFORMATION: Synthetic oligonucleotide: C(kappa)Rev1

<400> SEQUENCE: 52
tccaccttcc actg                                                        14

<210> SEQ ID NO 53
<211> LENGTH: 14
<212> TYPE: DNA
<213> ORGANISM: Artificial Sequence
<220> FEATURE:
<223> OTHER INFORMATION: Synthetic oligonucleotide: C(kappa)Rev2

<400> SEQUENCE: 53
caggcacaca acag                                                        14

<210> SEQ ID NO 54
<211> LENGTH: 14
<212> TYPE: DNA
<213> ORGANISM: Artificial Sequence
<220> FEATURE:
<223> OTHER INFORMATION: Synthetic oligonucleotide: C(kappa)Rev3

<400> SEQUENCE: 54
gagtgtcaca gagc                                                        14

<210> SEQ ID NO 55
<211> LENGTH: 14
<212> TYPE: DNA
<213> ORGANISM: Artificial Sequence
<220> FEATURE:
<223> OTHER INFORMATION: Synthetic oligonucleotide: C(lambda)Rev1

<400> SEQUENCE: 55
gggaacagag tgac                                                        14

<210> SEQ ID NO 56
<211> LENGTH: 14
<212> TYPE: DNA
<213> ORGANISM: Artificial Sequence
<220> FEATURE:
<223> OTHER INFORMATION: Synthetic oligonucleotide: C(lambda)Rev2

<400> SEQUENCE: 56
gtgtggcctt gttg                                                        14

<210> SEQ ID NO 57
<211> LENGTH: 14
<212> TYPE: DNA
<213> ORGANISM: Artificial Sequence
<220> FEATURE:
<223> OTHER INFORMATION: Synthetic oligonucleotide: C(lambda)Rev3.

```
<400> SEQUENCE: 57
ccatctgcct tcca                                                     14

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide: VH1/7LS

<400> SEQUENCE: 58
atcctcttyt tggtggsagc                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide: VH1-46LS

<400> SEQUENCE: 59
ggtcttctgc ttgctggctg                                               20

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide: VH2LS

<400> SEQUENCE: 60
cctgctgctg accayccctt c                                             21

<210> SEQ ID NO 61
<211> LENGTH: 24
<212> TYPE: DNA
<213> ORGANISM: Artificial Sequence
<220> FEATURE:
<223> OTHER INFORMATION: Synthetic oligonucleotide: VH3LS

<400> SEQUENCE: 61
gctattttwv raggtgtcca rtgt                                          24

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide: VH4LS

<400> SEQUENCE: 62
gcrgctccca gatgggtcct g                                             21

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide: VH5LS

<400> SEQUENCE: 63
atggggtcaa ccgccatcct                                               20

<210> SEQ ID NO 64
<211> LENGTH: 20
```

```
<212> TYPE: DNA
<213> ORGANISM: Artificial Sequence
<220> FEATURE:
<223> OTHER INFORMATION: Synthetic oligonucleotide: VH6LS

<400> SEQUENCE: 64
tgggcctccc atggggtgtc                                              20

<210> SEQ ID NO 65
<211> LENGTH: 24
<212> TYPE: DNA
<213> ORGANISM: Artificial Sequence
<220> FEATURE:
<223> OTHER INFORMATION: Synthetic oligonucleotide: JH1/2sRev

<400> SEQUENCE: 65
ctgaggagac rgtgaccagg gtgc                                         24

<210> SEQ ID NO 66
<211> LENGTH: 24
<212> TYPE: DNA
<213> ORGANISM: Artificial Sequence
<220> FEATURE:
<223> OTHER INFORMATION: Synthetic oligonucleotide: JH4/5sRev

<400> SEQUENCE: 66
ctgaggagac ggtgaccagg gttc                                         24

<210> SEQ ID NO 67
<211> LENGTH: 24
<212> TYPE: DNA
<213> ORGANISM: Artificial Sequence
<220> FEATURE:
<223> OTHER INFORMATION: Synthetic oligonucleotide: JH6sRev

<400> SEQUENCE: 67
ctgaggagac ggtgaccgtg gtcc                                         24

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide: JH3sRev

<400> SEQUENCE: 68
ctgaagagac ggtgaccatt gtcc                                         24

<210> SEQ ID NO 69
<211> LENGTH: 53
<212> TYPE: DNA
<213> ORGANISM: Artificial Sequence
<220> FEATURE:
<223> OTHER INFORMATION: Synthetic oligonucleotide: VH1Forward

<400> SEQUENCE: 69
tttacaatta cagtgttgcg accatggagg tgcagctggt gcagtctggr sct         53

<210> SEQ ID NO 70
<211> LENGTH: 50
<212> TYPE: DNA
<213> ORGANISM: Artificial Sequence
<220> FEATURE:
<223> OTHER INFORMATION: Synthetic oligonucleotide: VH2Forward
```

<400> SEQUENCE: 70
tttacaatta cagtgttgcg accatggagr tcaccttgar ggagtctggt          50

<210> SEQ ID NO 71
<211> LENGTH: 53
<212> TYPE: DNA
<213> ORGANISM: Artificial Sequence
<220> FEATURE:
<223> OTHER INFORMATION: Synthetic oligonucleotide: VH3Forward

<400> SEQUENCE: 71
tttacaatta cagtgttgcg accatggagg tgcagctgkt ggagtctsgr gga      53

<210> SEQ ID NO 72
<211> LENGTH: 50
<212> TYPE: DNA
<213> ORGANISM: Artificial Sequence
<220> FEATURE:
<223> OTHER INFORMATION: Synthetic oligonucleotide: VH4Forward

<400> SEQUENCE: 72
tttacaatta cagtgttgcg accatggagg tgcagctgca gsagtssggc          50

<210> SEQ ID NO 73
<211> LENGTH: 53
<212> TYPE: DNA
<213> ORGANISM: Artificial Sequence
<220> FEATURE:
<223> OTHER INFORMATION: Synthetic oligonucleotide: VH5Forward

<400> SEQUENCE: 73
tttacaatta cagtgttgcg accatggagg tgcagctggt gcagtctgga gca      53

<210> SEQ ID NO 74
<211> LENGTH: 48
<212> TYPE: DNA
<213> ORGANISM: Artificial Sequence
<220> FEATURE:
<223> OTHER INFORMATION: Synthetic oligonucleotide: VH6Forward

<400> SEQUENCE: 74
tttacaatta cagtgttgcg accatggagg tacagctgca gcagtcag            48

<210> SEQ ID NO 75
<211> LENGTH: 51
<212> TYPE: DNA
<213> ORGANISM: Artificial Sequence
<220> FEATURE:
<223> OTHER INFORMATION: Synthetic oligonucleotide: VH7Forward

<400> SEQUENCE: 75
tttacaatta cagtgttgcg accatggagg tgcagctggt gcaatctggg t        51

<210> SEQ ID NO 76
<211> LENGTH: 54
<212> TYPE: DNA
<213> ORGANISM: Artificial Sequence
<220> FEATURE:
<223> OTHER INFORMATION: Synthetic oligonucleotide: JHReverse1/2

<400> SEQUENCE: 76
cgctacctcc gccgccagac ccgcctccac ctgaggagac rgtgaccagg gtgc     54

<210> SEQ ID NO 77
<211> LENGTH: 54

```
<212> TYPE: DNA
<213> ORGANISM: Artificial Sequence
<220> FEATURE:
<223> OTHER INFORMATION: Synthetic oligonucleotide: JHReverse4/5

<400> SEQUENCE: 77
cgctacctcc gccgccagac ccgcctccac ctgaggagac ggtgaccagg gttc        54

<210> SEQ ID NO 78
<211> LENGTH: 54
<212> TYPE: DNA
<213> ORGANISM: Artificial Sequence
<220> FEATURE:
<223> OTHER INFORMATION: Synthetic oligonucleotide: JHReverse6

<400> SEQUENCE: 78
cgctacctcc gccgccagac ccgcctccac ctgaggagac ggtgaccgtg gtcc        54

<210> SEQ ID NO 79
<211> LENGTH: 54
<212> TYPE: DNA
<213> ORGANISM: Artificial Sequence
<220> FEATURE:
<223> OTHER INFORMATION: Synthetic oligonucleotide: JHReverse3

<400> SEQUENCE: 79
cgctacctcc gccgccagac ccgcctccac ctgaagagac ggtgaccatt gtcc        54

<210> SEQ ID NO 80
<211> LENGTH: 52
<212> TYPE: DNA
<213> ORGANISM: Artificial Sequence
<220> FEATURE:
<223> OTHER INFORMATION: Synthetic oligonucleotide: T7TMVTag2

<400> SEQUENCE: 80
taatacgact cactataggg acaattacta tttacaatta cagtgttgcg ac          52

<210> SEQ ID NO 81
<211> LENGTH: 17
<212> TYPE: DNA
<213> ORGANISM: Artificial Sequence
<220> FEATURE:
<223> OTHER INFORMATION: Synthetic oligonucleotide: V(kappa)1LS

<400> SEQUENCE: 81
gctcctgggr ctyctgc                                                 17

<210> SEQ ID NO 82
<211> LENGTH: 18
<212> TYPE: DNA
<213> ORGANISM: Artificial Sequence
<220> FEATURE:
<223> OTHER INFORMATION: Synthetic oligonucleotide: V(kappa)2LS

<400> SEQUENCE: 82
ctyctggggc tgctaatg                                                18

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide: V(kappa)3LS
```

<400> SEQUENCE: 83
ctctggctcm cagataccac                                            20

<210> SEQ ID NO 84
<211> LENGTH: 19
<212> TYPE: DNA
<213> ORGANISM: Artificial Sequence
<220> FEATURE:
<223> OTHER INFORMATION: Synthetic oligonucleotide: V(kappa)4LS

<400> SEQUENCE: 84
ggatctctgg tgcctacgg                                             19

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide: V(kappa)5LS

<400> SEQUENCE: 85
ggatctctga taccagggca                                            20

<210> SEQ ID NO 86
<211> LENGTH: 18
<212> TYPE: DNA
<213> ORGANISM: Artificial Sequence
<220> FEATURE:
<223> OTHER INFORMATION: Synthetic oligonucleotide: V(kappa)6LS

<400> SEQUENCE: 86
ctgggttcca gcctccag                                              18

<210> SEQ ID NO 87
<211> LENGTH: 27
<212> TYPE: DNA
<213> ORGANISM: Artificial Sequence
<220> FEATURE:
<223> OTHER INFORMATION: Synthetic oligonucleotide: C(kappa)-s Reverse
      primer:

<400> SEQUENCE: 87
gaagacagat ggtgcagcca cagttcg                                    27

<210> SEQ ID NO 88
<211> LENGTH: 59
<212> TYPE: DNA
<213> ORGANISM: Artificial Sequence
<220> FEATURE:
<223> OTHER INFORMATION: Synthetic oligonucleotide: V(kappa)1 Forward

<400> SEQUENCE: 88
gtctggcggc ggaggtagcg gcggtggcgg atcggacatc crgwtgaccc agtctccwt   59

<210> SEQ ID NO 89
<211> LENGTH: 59
<212> TYPE: DNA
<213> ORGANISM: Artificial Sequence
<220> FEATURE:
<223> OTHER INFORMATION: Synthetic oligonucleotide: V(kappa)2 Forward

<400> SEQUENCE: 89
gtctggcggc ggaggtagcg gcggtggcgg atcggatatt gtgatgacyc agwctccac   59

<210> SEQ ID NO 90

```
<211> LENGTH: 60
<212> TYPE: DNA
<213> ORGANISM: Artificial Sequence
<220> FEATURE:
<223> OTHER INFORMATION: Synthetic oligonucleotide: V(kappa)3 Forward

<400> SEQUENCE: 90
ctggcggcgg aggtagcggc ggtggcggat cggaaattgt gwtgacrcag tctccagsca    60

<210> SEQ ID NO 91
<211> LENGTH: 60
<212> TYPE: DNA
<213> ORGANISM: Artificial Sequence
<220> FEATURE:
<223> OTHER INFORMATION: Synthetic oligonucleotide: V(kappa)4/6 Forward

<400> SEQUENCE: 91
gtctggcggc ggaggtagcg gcggtggcgg atcggacatc gtgmtgacyc agtctccaga    60

<210> SEQ ID NO 92
<211> LENGTH: 60
<212> TYPE: DNA
<213> ORGANISM: Artificial Sequence
<220> FEATURE:
<223> OTHER INFORMATION: Synthetic oligonucleotide: V(kappa)5 For-NEW

<400> SEQUENCE: 92
ctggcggcgg aggtagcggc ggtggcggat cggaaacgac actcacgcag tctccagcat    60

<210> SEQ ID NO 93
<211> LENGTH: 60
<212> TYPE: DNA
<213> ORGANISM: Artificial Sequence
<220> FEATURE:
<223> OTHER INFORMATION: Synthetic oligonucleotide: V(kappa)6 For-NEW

<400> SEQUENCE: 93
ctggcggcgg aggtagcggc ggtggcggat cggatgtcgt gatgacacag tctccagctt    60

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide: Lib-GS-Fwd

<400> SEQUENCE: 94
gtctggcggc ggaggtagcg                                                20

<210> SEQ ID NO 95
<211> LENGTH: 57
<212> TYPE: DNA
<213> ORGANISM: Artificial Sequence
<220> FEATURE:
<223> OTHER INFORMATION: Synthetic oligonucleotide: FLAG-A20.Rev

<400> SEQUENCE: 95
tttttttttt tttttttttt aaatagcgga tgccttgtcg tcgtcgtcct tgtagtc       57

<210> SEQ ID NO 96
<211> LENGTH: 18
<212> TYPE: DNA
<213> ORGANISM: Artificial Sequence
```

```
<220> FEATURE:
<223> OTHER INFORMATION: Synthetic oligonucleotide: VL1LS-1

<400> SEQUENCE: 96
tcactgtgca gggtcctg                                                 18

<210> SEQ ID NO 97
<211> LENGTH: 18
<212> TYPE: DNA
<213> ORGANISM: Artificial Sequence
<220> FEATURE:
<223> OTHER INFORMATION: Synthetic oligonucleotide: VL1LS-3

<400> SEQUENCE: 97
tcactgcaca gggtcctg                                                 18

<210> SEQ ID NO 98
<211> LENGTH: 18
<212> TYPE: DNA
<213> ORGANISM: Artificial Sequence
<220> FEATURE:
<223> OTHER INFORMATION: Synthetic oligonucleotide: VL2LS-3

<400> SEQUENCE: 98
tcaggrcaca gggtcctg                                                 18

<210> SEQ ID NO 99
<211> LENGTH: 18
<212> TYPE: DNA
<213> ORGANISM: Artificial Sequence
<220> FEATURE:
<223> OTHER INFORMATION: Synthetic oligonucleotide: VL2LS-4

<400> SEQUENCE: 99
tcagggcaca ggatcctg                                                 18

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide: VL3LS-2

<400> SEQUENCE: 100
tgcataggtt ctgtggtttc ttctg                                         25

<210> SEQ ID NO 101
<211> LENGTH: 22
<212> TYPE: DNA
<213> ORGANISM: Artificial Sequence
<220> FEATURE:
<223> OTHER INFORMATION: Synthetic oligonucleotide: VL3LS-3

<400> SEQUENCE: 101
acagghtctg wggcctccta tg                                            22

<210> SEQ ID NO 102
<211> LENGTH: 25
<212> TYPE: DNA
<213> ORGANISM: Artificial Sequence
<220> FEATURE:
<223> OTHER INFORMATION: Synthetic oligonucleotide: VL3LS-4
```

<400> SEQUENCE: 102
tgcacaggct ctgtgacctc ctatg                               25

<210> SEQ ID NO 103
<211> LENGTH: 25
<212> TYPE: DNA
<213> ORGANISM: Artificial Sequence
<220> FEATURE:
<223> OTHER INFORMATION: Synthetic oligonucleotide: VL3LS-5

<400> SEQUENCE: 103
tacacaggct ctattgcctc ctatg                               25

<210> SEQ ID NO 104
<211> LENGTH: 26
<212> TYPE: DNA
<213> ORGANISM: Artificial Sequence
<220> FEATURE:
<223> OTHER INFORMATION: Synthetic oligonucleotide: VL4Cls-2

<400> SEQUENCE: 104
cttcattttc tccacaggtc tctgtg                              26

<210> SEQ ID NO 105
<211> LENGTH: 21
<212> TYPE: DNA
<213> ORGANISM: Artificial Sequence
<220> FEATURE:
<223> OTHER INFORMATION: Synthetic oligonucleotide: VL4abLS-2

<400> SEQUENCE: 105
tccactgsac agggtctctc t                                   21

<210> SEQ ID NO 106
<211> LENGTH: 18
<212> TYPE: DNA
<213> ORGANISM: Artificial Sequence
<220> FEATURE:
<223> OTHER INFORMATION: Synthetic oligonucleotide: VL5LS

<400> SEQUENCE: 106
cactgcacag gttccctc                                       18

<210> SEQ ID NO 107
<211> LENGTH: 18
<212> TYPE: DNA
<213> ORGANISM: Artificial Sequence
<220> FEATURE:
<223> OTHER INFORMATION: Synthetic oligonucleotide: VL6LS

<400> SEQUENCE: 107
ctgcacaggt tcttgggc                                       18

<210> SEQ ID NO 108
<211> LENGTH: 18
<212> TYPE: DNA
<213> ORGANISM: Artificial Sequence
<220> FEATURE:
<223> OTHER INFORMATION: Synthetic oligonucleotide: VL7LS

<400> SEQUENCE: 108
ctcacttgct gcccaggg                                       18

<210> SEQ ID NO 109
<211> LENGTH: 23

```
<212> TYPE: DNA
<213> ORGANISM: Artificial Sequence
<220> FEATURE:
<223> OTHER INFORMATION: Synthetic oligonucleotide: VL8LS

<400> SEQUENCE: 109
gcttatggat caggagtgga ttc                                              23

<210> SEQ ID NO 110
<211> LENGTH: 19
<212> TYPE: DNA
<213> ORGANISM: Artificial Sequence
<220> FEATURE:
<223> OTHER INFORMATION: Synthetic oligonucleotide: VL9LS

<400> SEQUENCE: 110
caccctcctc agtctcctc                                                    19

<210> SEQ ID NO 111
<211> LENGTH: 19
<212> TYPE: DNA
<213> ORGANISM: Artificial Sequence
<220> FEATURE:
<223> OTHER INFORMATION: Synthetic oligonucleotide: VL10LS

<400> SEQUENCE: 111
ctctgcagtg tcagtggtc                                                    19

<210> SEQ ID NO 112
<211> LENGTH: 23
<212> TYPE: DNA
<213> ORGANISM: Artificial Sequence
<220> FEATURE:
<223> OTHER INFORMATION: Synthetic oligonucleotide: CJL-sReverse

<400> SEQUENCE: 112
gccttgggct gacckaggac ggt                                              23

<210> SEQ ID NO 113
<211> LENGTH: 55
<212> TYPE: DNA
<213> ORGANISM: Artificial Sequence
<220> FEATURE:
<223> OTHER INFORMATION: Synthetic oligonucleotide: VL1/10 ForRedo

<400> SEQUENCE: 113
gtctggcggc ggaggtagcg gcggtggcga tcgcagtctg kgctgackca gccrc           55

<210> SEQ ID NO 114
<211> LENGTH: 55
<212> TYPE: DNA
<213> ORGANISM: Artificial Sequence
<220> FEATURE:
<223> OTHER INFORMATION: Synthetic oligonucleotide: VL2 Forward

<400> SEQUENCE: 114
gtctggcggc ggaggtagcg gcggtggcgg atcgcagtct gccctgactc agcct           55

<210> SEQ ID NO 115
<211> LENGTH: 52
<212> TYPE: DNA
<213> ORGANISM: Artificial Sequence
<220> FEATURE:
<223> OTHER INFORMATION: Synthetic oligonucleotide: VL3 Forward-New
```

-continued

<400> SEQUENCE: 115
gtctggcggc ggaggtagcg gcggtggcgg atcgtcctat gagctgacdc ag        52

<210> SEQ ID NO 116
<211> LENGTH: 54
<212> TYPE: DNA
<213> ORGANISM: Artificial Sequence
<220> FEATURE:
<223> OTHER INFORMATION: Synthetic oligonucleotide: VL4ab Forward

<400> SEQUENCE: 116
gtctggcggc ggaggtagcg gcggtggcgg atcgcagcyt gtgctgactc aatc      54

<210> SEQ ID NO 117
<211> LENGTH: 58
<212> TYPE: DNA
<213> ORGANISM: Artificial Sequence
<220> FEATURE:
<223> OTHER INFORMATION: Synthetic oligonucleotide: VL4c Forward

<400> SEQUENCE: 117
gtctggcggc ggaggtagcg gcggtggcgg atcgctgcct gtgctgactc agccccccg    58

<210> SEQ ID NO 118
<211> LENGTH: 58
<212> TYPE: DNA
<213> ORGANISM: Artificial Sequence
<220> FEATURE:
<223> OTHER INFORMATION: Synthetic oligonucleotide: VL5/9 Forward

<400> SEQUENCE: 118
gtctggcggc ggaggtagcg gcggtggcgg atcgcagcct gtgctgactc agccrbct     58

<210> SEQ ID NO 119
<211> LENGTH: 55
<212> TYPE: DNA
<213> ORGANISM: Artificial Sequence
<220> FEATURE:
<223> OTHER INFORMATION: Synthetic oligonucleotide: VL6 Forward

<400> SEQUENCE: 119
gtctggcggc ggaggtagcg gcggtggcgg atcgaatttt atgctgactc agccc       55

<210> SEQ ID NO 120
<211> LENGTH: 55
<212> TYPE: DNA
<213> ORGANISM: Artificial Sequence
<220> FEATURE:
<223> OTHER INFORMATION: Synthetic oligonucleotide: VL7/8 Forward

<400> SEQUENCE: 120
gtctggcggc ggaggtagcg gcggtggcgg atcgcagrct gtggtgacyc aggag       55

<210> SEQ ID NO 121
<211> LENGTH: 53
<212> TYPE: DNA
<213> ORGANISM: Artificial Sequence
<220> FEATURE:
<223> OTHER INFORMATION: Synthetic oligonucleotide: VH1Forward

<400> SEQUENCE: 121
tttacaatta cagcttcttc accatggagg tgcagctggt gcagtctggr sct         53

<210> SEQ ID NO 122
<211> LENGTH: 50

```
<212> TYPE: DNA
<213> ORGANISM: Artificial Sequence
<220> FEATURE:
<223> OTHER INFORMATION: Synthetic oligonucleotide: VH2Forward

<400> SEQUENCE: 122
tttacaatta cagcttcttc accatggagr tcaccttgar ggagtctggt                 50

<210> SEQ ID NO 123
<211> LENGTH: 52
<212> TYPE: DNA
<213> ORGANISM: Artificial Sequence
<220> FEATURE:
<223> OTHER INFORMATION: Synthetic oligonucleotide: VH3Forward

<400> SEQUENCE: 123
ttacaattac agcttcttca ccatggaggt gcagctgktg gagtctsgrg ga              52

<210> SEQ ID NO 124
<211> LENGTH: 50
<212> TYPE: DNA
<213> ORGANISM: Artificial Sequence
<220> FEATURE:
<223> OTHER INFORMATION: Synthetic oligonucleotide: VH4Forward

<400> SEQUENCE: 124
tttacaatta cagcttcttc accatggagg tgcagctgca gsagtssggc                 50

<210> SEQ ID NO 125
<211> LENGTH: 53
<212> TYPE: DNA
<213> ORGANISM: Artificial Sequence
<220> FEATURE:
<223> OTHER INFORMATION: Synthetic oligonucleotide: VH5Forward

<400> SEQUENCE: 125
tttacaatta cagcttcttc accatggagg tgcagctggt gcagtctgga gca             53

<210> SEQ ID NO 126
<211> LENGTH: 48
<212> TYPE: DNA
<213> ORGANISM: Artificial Sequence
<220> FEATURE:
<223> OTHER INFORMATION: Synthetic oligonucleotide: VH6Forward

<400> SEQUENCE: 126
tttacaatta cagcttcttc accatggagg tacagctgca gcagtcag                   48

<210> SEQ ID NO 127
<211> LENGTH: 51
<212> TYPE: DNA
<213> ORGANISM: Artificial Sequence
<220> FEATURE:
<223> OTHER INFORMATION: Synthetic oligonucleotide: VH7Forward

<400> SEQUENCE: 127
tttacaatta cagcttcttc accatggagg tgcagctggt gcaatctggg t               51

<210> SEQ ID NO 128
<211> LENGTH: 54
<212> TYPE: DNA
<213> ORGANISM: Artificial Sequence
<220> FEATURE:
<223> OTHER INFORMATION: Synthetic oligonucleotide: JHReverse1/2

<400> SEQUENCE: 128
cgctacctcc gccgccagac ccgcctccac ctgaggagac rgtgaccagg gtgc            54
```

<210> SEQ ID NO 129
<211> LENGTH: 54
<212> TYPE: DNA
<213> ORGANISM: Artificial Sequence
<220> FEATURE:
<223> OTHER INFORMATION: Synthetic oligonucleotide: JHReverse3

<400> SEQUENCE: 129
cgctacctcc gccgccagac ccgcctccac ctgaagagac ggtgaccatt gtcc       54

<210> SEQ ID NO 130
<211> LENGTH: 54
<212> TYPE: DNA
<213> ORGANISM: Artificial Sequence
<220> FEATURE:
<223> OTHER INFORMATION: Synthetic oligonucleotide: JHReverse4/5

<400> SEQUENCE: 130
cgctacctcc gccgccagac ccgcctccac ctgaggagac ggtgaccagg gttc       54

<210> SEQ ID NO 131
<211> LENGTH: 54
<212> TYPE: DNA
<213> ORGANISM: Artificial Sequence
<220> FEATURE:
<223> OTHER INFORMATION: Synthetic oligonucleotide: JHReverse6

<400> SEQUENCE: 131
cgctacctcc gccgccagac ccgcctccac ctgaggagac ggtgaccgtg gtcc       54

<210> SEQ ID NO 132
<211> LENGTH: 50
<212> TYPE: DNA
<213> ORGANISM: Artificial Sequence
<220> FEATURE:
<223> OTHER INFORMATION: Synthetic oligonucleotide: T7TMVTag4s

<400> SEQUENCE: 132
taatacgact cactataggg acaattacta tttacaatta cagcttcttc             50

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide: Lib-GSv2-Rev

<400> SEQUENCE: 133
cagaccctcc accgccgctg                                              20

<210> SEQ ID NO 134
<211> LENGTH: 59
<212> TYPE: DNA
<213> ORGANISM: Artificial Sequence
<220> FEATURE:
<223> OTHER INFORMATION: Synthetic oligonucleotide: V(kappa)1FwdV2

<400> SEQUENCE: 134
cagcggcggt ggagggtctg gcggtggcgg aagtgacatc crgwtgaccc agtctccwt   59

<210> SEQ ID NO 135
<211> LENGTH: 59
<212> TYPE: DNA
<213> ORGANISM: Artificial Sequence
<220> FEATURE:

<223> OTHER INFORMATION: Synthetic oligonucleotide: V(kappa)2FwdV2

<400> SEQUENCE: 135
cagcggcggt ggagggtctg gcggtggcgg aagtgatatt gtgatgacyc agwctccac    59

<210> SEQ ID NO 136
<211> LENGTH: 62
<212> TYPE: DNA
<213> ORGANISM: Artificial Sequence
<220> FEATURE:
<223> OTHER INFORMATION: Synthetic oligonucleotide: V(kappa)3FwdV2

<400> SEQUENCE: 136
cagcggcggt ggagggtctg gcggtggcgg aagtgaaatt gtgwtgacrc agtctccags    60
ca    62

<210> SEQ ID NO 137
<211> LENGTH: 60
<212> TYPE: DNA
<213> ORGANISM: Artificial Sequence
<220> FEATURE:
<223> OTHER INFORMATION: Synthetic oligonucleotide: V(kappa)4/6FwdV2

<400> SEQUENCE: 137
cagcggcggt ggagggtctg gcggtggcgg aagtgacatc gtgmtgacyc agtctccaga    60

<210> SEQ ID NO 138
<211> LENGTH: 62
<212> TYPE: DNA
<213> ORGANISM: Artificial Sequence
<220> FEATURE:
<223> OTHER INFORMATION: Synthetic oligonucleotide: V(kappa)5FwdV2

<400> SEQUENCE: 138
cagcggcggt ggagggtctg gcggtggcgg aagtgaaacg acactcacgc agtctccagc    60
at    62

<210> SEQ ID NO 139
<211> LENGTH: 62
<212> TYPE: DNA
<213> ORGANISM: Artificial Sequence
<220> FEATURE:
<223> OTHER INFORMATION: Synthetic oligonucleotide: V(kappa)6FwdV2

<400> SEQUENCE: 139
cagcggcggt ggagggtctg gcggtggcgg aagtgatgtc gtgatgacac agtctccagc    60
tt    62

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide: Lib-GSv2-Fwd

<400> SEQUENCE: 140
cagcggcggt ggagggtctg    20

<210> SEQ ID NO 141
<211> LENGTH: 54
<212> TYPE: DNA
<213> ORGANISM: Artificial Sequence
<220> FEATURE:
<223> OTHER INFORMATION: Synthetic oligonucleotide: JH1/2RevV2

<400> SEQUENCE: 141
cagaccctcc accgccgctg ccgcctccac ctgaggagac rgtgaccagg gtgc         54

<210> SEQ ID NO 142
<211> LENGTH: 54
<212> TYPE: DNA
<213> ORGANISM: Artificial Sequence
<220> FEATURE:
<223> OTHER INFORMATION: Synthetic oligonucleotide: JH3RevV2

<400> SEQUENCE: 142
cagaccctcc accgccgctg ccgcctccac ctgaagagac ggtgaccatt gtcc         54

<210> SEQ ID NO 143
<211> LENGTH: 54
<212> TYPE: DNA
<213> ORGANISM: Artificial Sequence
<220> FEATURE:
<223> OTHER INFORMATION: Synthetic oligonucleotide: JH4/5RevV2

<400> SEQUENCE: 143
cagaccctcc accgccgctg ccgcctccac ctgaggagac ggtgaccagg gttc         54

<210> SEQ ID NO 144
<211> LENGTH: 54
<212> TYPE: DNA
<213> ORGANISM: Artificial Sequence
<220> FEATURE:
<223> OTHER INFORMATION: Synthetic oligonucleotide: JH6RevV2

<400> SEQUENCE: 144
cagaccctcc accgccgctg ccgcctccac ctgaggagac ggtgaccgtg gtcc         54

<210> SEQ ID NO 145
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 145
cagcggcggt ggagggtctg                                               20

<210> SEQ ID NO 146
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 146
tcctcaggtg gaggcggcag cggcggtgga gggtctggcg gtggcggaag t            51

<210> SEQ ID NO 147
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 147
acttccgcca ccgccagacc ctccaccgcc gctgccgcct ccacctgagg a            51

<210> SEQ ID NO 148
<211> LENGTH: 20

```
<212> TYPE: DNA
<213> ORGANISM: Artificial Sequence
<220> FEATURE:
<223> OTHER INFORMATION: Synthetic oligonucleotide: T7-TMV-Seq

<400> SEQUENCE: 148
ctcactatag ggacaattac                                               20

<210> SEQ ID NO 149
<211> LENGTH: 52
<212> TYPE: DNA
<213> ORGANISM: Artificial Sequence
<220> FEATURE:
<223> OTHER INFORMATION: Synthetic oligonucleotide: T7TMVTag3

<400> SEQUENCE: 149
taatacgact cactataggg acaattacta tttacaatta caggctttgg ac           52

<210> SEQ ID NO 150
<211> LENGTH: 52
<212> TYPE: DNA
<213> ORGANISM: Artificial Sequence
<220> FEATURE:
<223> OTHER INFORMATION: Synthetic oligonucleotide: T7TMVTag4

<400> SEQUENCE: 150
taatacgact cactataggg acaattacta tttacaatta cagcttcttc ac           52

<210> SEQ ID NO 151
<211> LENGTH: 50
<212> TYPE: DNA
<213> ORGANISM: Artificial Sequence
<220> FEATURE:
<223> OTHER INFORMATION: Synthetic oligonucleotide: T7TMVTag2s

<400> SEQUENCE: 151
taatacgact cactataggg acaattacta tttacaatta cagtgttgcg              50

<210> SEQ ID NO 152
<211> LENGTH: 50
<212> TYPE: DNA
<213> ORGANISM: Artificial Sequence
<220> FEATURE:
<223> OTHER INFORMATION: Synthetic oligonucleotide: T7TMVTag3s

<400> SEQUENCE: 152
taatacgact cactataggg acaattacta tttacaatta caggctttgg              50

<210> SEQ ID NO 153
<211> LENGTH: 57
<212> TYPE: DNA
<213> ORGANISM: Artificial Sequence
<220> FEATURE:
<223> OTHER INFORMATION: Synthetic oligonucleotide: T7TMVTag4L

<400> SEQUENCE: 153
taatacgact cactataggg acaattacta tttacaatta cagcttcttc accatgg      57

<210> SEQ ID NO 154
<211> LENGTH: 37
<212> TYPE: DNA
<213> ORGANISM: Artificial Sequence
<220> FEATURE:
<223> OTHER INFORMATION: Synthetic oligonucleotide: TMVTag4L
```

<400> SEQUENCE: 154
acaattacta tttacaatta cagcttcttc accatgg                                37

<210> SEQ ID NO 155
<211> LENGTH: 32
<212> TYPE: DNA
<213> ORGANISM: Artificial Sequence
<220> FEATURE:
<223> OTHER INFORMATION: Synthetic oligonucleotide: TMVTag4

<400> SEQUENCE: 155
acaattacta tttacaatta cagcttcttc ac                                    32

<210> SEQ ID NO 156
<211> LENGTH: 30
<212> TYPE: DNA
<213> ORGANISM: Artificial Sequence
<220> FEATURE:
<223> OTHER INFORMATION: Synthetic oligonucleotide: TMVTag4s

<400> SEQUENCE: 156
acaattacta tttacaatta cagcttcttc                                       30

<210> SEQ ID NO 157
<211> LENGTH: 25
<212> TYPE: DNA
<213> ORGANISM: Artificial Sequence
<220> FEATURE:
<223> OTHER INFORMATION: Synthetic oligonucleotide: phylflag3's

<400> SEQUENCE: 157
ccttgtcgtc gtcgtccttg tagtc                                            25

<210> SEQ ID NO 158
<211> LENGTH: 57
<212> TYPE: DNA
<213> ORGANISM: Artificial Sequence
<220> FEATURE:
<223> OTHER INFORMATION: Synthetic oligonucleotide: VH-FLAGA20-Rev

<400> SEQUENCE: 158 ttttttttttt tttttttttt aaatagcgga tgctttgtca tcatcatctt tataatc        57

<210> SEQ ID NO 159
<211> LENGTH: 45
<212> TYPE: DNA
<213> ORGANISM: Artificial Sequence
<220> FEATURE:
<223> OTHER INFORMATION: Synthetic oligonucleotide: JH1/2Cm-Rev

<400> SEQUENCE: 159
ggttggggcg gatgcactcc cctgaggaga crgtgaccag ggtgc                      45

<210> SEQ ID NO 160
<211> LENGTH: 45
<212> TYPE: DNA
<213> ORGANISM: Artificial Sequence
<220> FEATURE:
<223> OTHER INFORMATION: Synthetic oligonucleotide: JH4/5Cm-Rev

<400> SEQUENCE: 160
ggttggggcg gatgcactcc cctgaggaga cggtgaccag ggttc                      45

<210> SEQ ID NO 161
<211> LENGTH: 45

```
<212> TYPE: DNA
<213> ORGANISM: Artificial Sequence
<220> FEATURE:
<223> OTHER INFORMATION: Synthetic oligonucleotide: JH6Cm-Rev

<400> SEQUENCE: 161
ggttggggcg gatgcactcc cctgaggaga cggtgaccgt ggtcc                45

<210> SEQ ID NO 162
<211> LENGTH: 45
<212> TYPE: DNA
<213> ORGANISM: Artificial Sequence
<220> FEATURE:
<223> OTHER INFORMATION: Synthetic oligonucleotide: JH3Cm-Rev

<400> SEQUENCE: 162
ggttggggcg gatgcactcc cctgaagaga cggtgaccat tgtcc                45

<210> SEQ ID NO 163
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 163
cagaccctcc accgccgctg                                            20

<210> SEQ ID NO 164
<211> LENGTH: 17
<212> TYPE: PRT
<213> ORGANISM: Artificial Sequence
<220> FEATURE:
<223> OTHER INFORMATION: Synthetic amino acid

<400> SEQUENCE: 164

Ser Ser Gly Gly Gly Gly Ser Gly Gly Gly Gly Ser Gly Gly Gly Gly
1               5                   10                  15

Ser

<210> SEQ ID NO 165
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 165
cagctggtgg agtctggggg aggcttggtc cagcctgggg ggttc                45

<210> SEQ ID NO 166
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 166
tcctcaggtg gaggcggcag cggcggtgga gggtctg                         37

<210> SEQ ID NO 167
<211> LENGTH: 34
<212> TYPE: DNA
<213> ORGANISM: Artificial Sequence
<220> FEATURE:
<223> OTHER INFORMATION: Synthetic oligonucleotide
```

```
<400> SEQUENCE: 167
acttccgcca ccgccagacc ctccaccgcc gctg                                34

<210> SEQ ID NO 168
<211> LENGTH: 56
<212> TYPE: DNA
<213> ORGANISM: Artificial Sequence
<220> FEATURE:
<223> OTHER INFORMATION: Synthetic oligonucleotide: V(kappa)5 Forward

<400> SEQUENCE: 168
gtctggcggc ggaggtagcg gcggtggcgg atcggaaacg acactcacgc agtctc        56

<210> SEQ ID NO 169
<211> LENGTH: 59
<212> TYPE: DNA
<213> ORGANISM: Artificial Sequence
<220> FEATURE:
<223> OTHER INFORMATION: Synthetic oligonucleotide: V(kappa)6 Forward

<400> SEQUENCE: 169
ctggcggcgg aggtagcggc ggtggcggat cggatgtcgt gatgacacag tctccagct     59

<210> SEQ ID NO 170
<211> LENGTH: 69
<212> TYPE: DNA
<213> ORGANISM: Artificial Sequence
<220> FEATURE:
<223> OTHER INFORMATION: Synthetic oligonucleotide: C(kappa)-Long-
      Reverse primer

<400> SEQUENCE: 170
gtcgtcgtcg tccttgtagt cctcatcaga tggcgggaag atgaagacag atggtgcagc    60
cacagttcg                                                           69

<210> SEQ ID NO 171
<211> LENGTH: 78
<212> TYPE: DNA
<213> ORGANISM: Artificial Sequence
<220> FEATURE:
<223> OTHER INFORMATION: Synthetic oligonucleotide: C(kappa)L4-
      FlagA20-Rev

<400> SEQUENCE: 171
tttttttttt tttttttttt aaatagcgga tgccttgtcg tcgtcgtcct tgtagtcctc    60
atcagatggc gggaagat                                                 78

<210> SEQ ID NO 172
<211> LENGTH: 75
<212> TYPE: DNA
<213> ORGANISM: Artificial Sequence
<220> FEATURE:
<223> OTHER INFORMATION: Synthetic oligonucleotide: C(kappa)L3-
      FlagA20-Rev

<400> SEQUENCE: 172
tttttttttt tttttttttt aaatagcgga tgccttgtcg tcgtcgtcct tgtagtcctc    60
atcagatggc gggaa                                                    75

<210> SEQ ID NO 173
<211> LENGTH: 72
<212> TYPE: DNA
<213> ORGANISM: Artificial Sequence
<220> FEATURE:
```

<223> OTHER INFORMATION: Synthetic oligonucleotide: C(kappa)L2-
     FlagA20-Rev

<400> SEQUENCE: 173
tttttttttt tttttttttt aaatagcgga tgccttgtcg tcgtcgtcct tgtagtcctc    60
atcagatggc gg                                                        72

<210> SEQ ID NO 174
<211> LENGTH: 69
<212> TYPE: DNA
<213> ORGANISM: Artificial Sequence
<220> FEATURE:
<223> OTHER INFORMATION: Synthetic oligonucleotide: C(kappa)L1-
     FlagA20-Rev

<400> SEQUENCE: 174
tttttttttt tttttttttt aaatagcgga tgccttgtcg tcgtcgtcct tgtagtcctc    60
atcagatgg                                                            69

<210> SEQ ID NO 175
<211> LENGTH: 56
<212> TYPE: DNA
<213> ORGANISM: Artificial Sequence
<220> FEATURE:
<223> OTHER INFORMATION: Synthetic oligonucleotide: VL1/10 Forward

<400> SEQUENCE: 175
gtctggcggc ggaggtagcg gcggtggcgg atcgcagtct gkgctgackc agccrc        56

<210> SEQ ID NO 176
<211> LENGTH: 53
<212> TYPE: DNA
<213> ORGANISM: Artificial Sequence
<220> FEATURE:
<223> OTHER INFORMATION: Synthetic oligonucleotide: VH1FwdTag3

<400> SEQUENCE: 176
tttacaatta caggctttgg accatggagg tgcagctggt gcagtctggr sct           53

<210> SEQ ID NO 177
<211> LENGTH: 50
<212> TYPE: DNA
<213> ORGANISM: Artificial Sequence
<220> FEATURE:
<223> OTHER INFORMATION: Synthetic oligonucleotide: VH2FwdTag3

<400> SEQUENCE: 177
tttacaatta caggctttgg accatggagr tcaccttgar ggagtctggt               50

<210> SEQ ID NO 178
<211> LENGTH: 53
<212> TYPE: DNA
<213> ORGANISM: Artificial Sequence
<220> FEATURE:
<223> OTHER INFORMATION: Synthetic oligonucleotide: VH3FwdTag3

<400> SEQUENCE: 178
tttacaatta caggctttgg accatggagg tgcagctgkt ggagtctsgr gga           53

<210> SEQ ID NO 179
<211> LENGTH: 50
<212> TYPE: DNA
<213> ORGANISM: Artificial Sequence
<220> FEATURE:
<223> OTHER INFORMATION: Synthetic oligonucleotide: VH4FwdTag3

<400> SEQUENCE: 179
tttacaatta caggctttgg accatggagg tgcagctgca gsagtssggc                50

<210> SEQ ID NO 180
<211> LENGTH: 53
<212> TYPE: DNA
<213> ORGANISM: Artificial Sequence
<220> FEATURE:
<223> OTHER INFORMATION: Synthetic oligonucleotide: VH5FwdTag3

<400> SEQUENCE: 180
tttacaatta caggctttgg accatggagg tgcagctggt gcagtctgga gca            53

<210> SEQ ID NO 181
<211> LENGTH: 48
<212> TYPE: DNA
<213> ORGANISM: Artificial Sequence
<220> FEATURE:
<223> OTHER INFORMATION: Synthetic oligonucleotide: VH6FwdTag3

<400> SEQUENCE: 181
tttacaatta caggctttgg accatggagg tacagctgca gcagtcag                  48

<210> SEQ ID NO 182
<211> LENGTH: 51
<212> TYPE: DNA
<213> ORGANISM: Artificial Sequence
<220> FEATURE:
<223> OTHER INFORMATION: Synthetic oligonucleotide: VH7FwdTag3

<400> SEQUENCE: 182
tttacaatta caggctttgg accatggagg tgcagctggt gcaatctggg t              51

<210> SEQ ID NO 183
<211> LENGTH: 56
<212> TYPE: DNA
<213> ORGANISM: Artificial Sequence
<220> FEATURE:
<223> OTHER INFORMATION: Synthetic oligonucleotide: VL1/10FwdV2

<400> SEQUENCE: 183
cagcggcggt ggagggtctg gcggtggcgg aagtcagtct gkgctgackc agccrc         56

<210> SEQ ID NO 184
<211> LENGTH: 55
<212> TYPE: DNA
<213> ORGANISM: Artificial Sequence
<220> FEATURE:
<223> OTHER INFORMATION: Synthetic oligonucleotide: VL2FwdV2

<400> SEQUENCE: 184
cagcggcggt ggagggtctg gcggtggcgg aagtcagtct gccctgactc agcct          55

<210> SEQ ID NO 185
<211> LENGTH: 52
<212> TYPE: DNA
<213> ORGANISM: Artificial Sequence
<220> FEATURE:
<223> OTHER INFORMATION: Synthetic oligonucleotide: VL3FwdV2

<400> SEQUENCE: 185
cagcggcggt ggagggtctg gcggtggcgg aagttcctat gagctgacdc ag             52

<210> SEQ ID NO 186
<211> LENGTH: 54

```
<212> TYPE: DNA
<213> ORGANISM: Artificial Sequence
<220> FEATURE:
<223> OTHER INFORMATION: Synthetic oligonucleotide: VL4abFwdV2

<400> SEQUENCE: 186
cagcggcggt ggagggtctg gcggtggcgg aagtcagcyt gtgctgactc aatc         54

<210> SEQ ID NO 187
<211> LENGTH: 58
<212> TYPE: DNA
<213> ORGANISM: Artificial Sequence
<220> FEATURE:
<223> OTHER INFORMATION: Synthetic oligonucleotide: VL4cFwdV2

<400> SEQUENCE: 187
cagcggcggt ggagggtctg gcggtggcgg aagtctgcct gtgctgactc agccccg      58

<210> SEQ ID NO 188
<211> LENGTH: 58
<212> TYPE: DNA
<213> ORGANISM: Artificial Sequence
<220> FEATURE:
<223> OTHER INFORMATION: Synthetic oligonucleotide: VL5/9FwdV2

<400> SEQUENCE: 188
cagcggcggt ggagggtctg gcggtggcgg aagtcagcct gtgctgactc agccrbct     58

<210> SEQ ID NO 189
<211> LENGTH: 55
<212> TYPE: DNA
<213> ORGANISM: Artificial Sequence
<220> FEATURE:
<223> OTHER INFORMATION: Synthetic oligonucleotide: VL6FwdV2

<400> SEQUENCE: 189
cagcggcggt ggagggtctg gcggtggcgg aagtaatttt atgctgactc agccc        55

<210> SEQ ID NO 190
<211> LENGTH: 55
<212> TYPE: DNA
<213> ORGANISM: Artificial Sequence
<220> FEATURE:
<223> OTHER INFORMATION: Synthetic oligonucleotide: VL7/8FwdV2

<400> SEQUENCE: 190
cagcggcggt ggagggtctg gcggtggcgg aagtcagrct gtggtgacyc aggag        55

<210> SEQ ID NO 191
<211> LENGTH: 53
<212> TYPE: DNA
<213> ORGANISM: Artificial Sequence
<220> FEATURE:
<223> OTHER INFORMATION: Synthetic oligonucleotide: VH1FwdTag5

<400> SEQUENCE: 191
tttacaatta cagtgtctgt accatggagg tgcagctggt gcagtctggr sct          53

<210> SEQ ID NO 192
<211> LENGTH: 50
<212> TYPE: DNA
<213> ORGANISM: Artificial Sequence
<220> FEATURE:
<223> OTHER INFORMATION: Synthetic oligonucleotide: VH2FwdTag5

<400> SEQUENCE: 192
tttacaatta cagtgtctgt accatggagr tcaccttgar ggagtctggt              50
```

<210> SEQ ID NO 193
<211> LENGTH: 53
<212> TYPE: DNA
<213> ORGANISM: Artificial Sequence
<220> FEATURE:
<223> OTHER INFORMATION: Synthetic oligonucleotide: VH3FwdTag5

<400> SEQUENCE: 193
tttacaatta cagtgtctgt accatggagg tgcagctgkt ggagtctsgr gga        53

<210> SEQ ID NO 194
<211> LENGTH: 50
<212> TYPE: DNA
<213> ORGANISM: Artificial Sequence
<220> FEATURE:
<223> OTHER INFORMATION: Synthetic oligonucleotide: VH4FwdTag5

<400> SEQUENCE: 194
tttacaatta cagtgtctgt accatggagg tgcagctgca gsagtssggc             50

<210> SEQ ID NO 195
<211> LENGTH: 53
<212> TYPE: DNA
<213> ORGANISM: Artificial Sequence
<220> FEATURE:
<223> OTHER INFORMATION: Synthetic oligonucleotide: VH5FwdTag5

<400> SEQUENCE: 195
tttacaatta cagtgtctgt accatggagg tgcagctggt gcagtctgga gca        53

<210> SEQ ID NO 196
<211> LENGTH: 48
<212> TYPE: DNA
<213> ORGANISM: Artificial Sequence
<220> FEATURE:
<223> OTHER INFORMATION: Synthetic oligonucleotide: VH6FwdTag5

<400> SEQUENCE: 196
tttacaatta cagtgtctgt accatggagg tacagctgca gcagtcag               48

<210> SEQ ID NO 197
<211> LENGTH: 51
<212> TYPE: DNA
<213> ORGANISM: Artificial Sequence
<220> FEATURE:
<223> OTHER INFORMATION: Synthetic oligonucleotide: VH7FwdTag5

<400> SEQUENCE: 197
tttacaatta cagtgtctgt accatggagg tgcagctggt gcaatctggg t           51

<210> SEQ ID NO 198
<211> LENGTH: 53
<212> TYPE: DNA
<213> ORGANISM: Artificial Sequence
<220> FEATURE:
<223> OTHER INFORMATION: Synthetic oligonucleotide: VH1FwdTag6

<400> SEQUENCE: 198
tttacaatta cagtttggct accatggagg tgcagctggt gcagtctggr sct        53

<210> SEQ ID NO 199
<211> LENGTH: 50
<212> TYPE: DNA
<213> ORGANISM: Artificial Sequence
<220> FEATURE:
<223> OTHER INFORMATION: Synthetic oligonucleotide: VH2FwdTag6

```
<400> SEQUENCE: 199
tttacaatta cagtttggct accatggagr tcaccttgar ggagtctggt                    50

<210> SEQ ID NO 200
<211> LENGTH: 54
<212> TYPE: DNA
<213> ORGANISM: Artificial Sequence
<220> FEATURE:
<223> OTHER INFORMATION: Synthetic oligonucleotide: VH3FwdTag6

<400> SEQUENCE: 200
tttacaatta cagtttggct caccatggag gtgcagctgk tggagtctsg rgga              54

<210> SEQ ID NO 201
<211> LENGTH: 50
<212> TYPE: DNA
<213> ORGANISM: Artificial Sequence
<220> FEATURE:
<223> OTHER INFORMATION: Synthetic oligonucleotide: VH4FwdTag6

<400> SEQUENCE: 201
tttacaatta cagtttggct accatggagg tgcagctgca gsagtssggc                    50

<210> SEQ ID NO 202
<211> LENGTH: 53
<212> TYPE: DNA
<213> ORGANISM: Artificial Sequence
<220> FEATURE:
<223> OTHER INFORMATION: Synthetic oligonucleotide: VH5FwdTag6

<400> SEQUENCE: 202
tttacaatta cagtttggct accatggagg tgcagctggt gcagtctgga gca                53

<210> SEQ ID NO 203
<211> LENGTH: 48
<212> TYPE: DNA
<213> ORGANISM: Artificial Sequence
<220> FEATURE:
<223> OTHER INFORMATION: Synthetic oligonucleotide: VH6FwdTag6

<400> SEQUENCE: 203
tttacaatta cagtttggct accatggagg tacagctgca gcagtcag                      48

<210> SEQ ID NO 204
<211> LENGTH: 51
<212> TYPE: DNA
<213> ORGANISM: Artificial Sequence
<220> FEATURE:
<223> OTHER INFORMATION: Synthetic oligonucleotide: VH7FwdTag6

<400> SEQUENCE: 204
tttacaatta cagtttggct accatggagg tgcagctggt gcaatctggg t                  51

<210> SEQ ID NO 205
<211> LENGTH: 30
<212> TYPE: DNA
<213> ORGANISM: Artificial Sequence
<220> FEATURE:
<223> OTHER INFORMATION: Synthetic oligonucleotide: TMVTag5s

<400> SEQUENCE: 205
acaattacta tttacaatta cagtgtctgt                                          30

<210> SEQ ID NO 206
<211> LENGTH: 30
```

```
<212> TYPE: DNA
<213> ORGANISM: Artificial Sequence
<220> FEATURE:
<223> OTHER INFORMATION: Synthetic oligonucleotide: TMVTag6s

<400> SEQUENCE: 206
acaattacta tttacaatta cagtttggct                                    30

<210> SEQ ID NO 207
<211> LENGTH: 33
<212> TYPE: DNA
<213> ORGANISM: Artificial Sequence
<220> FEATURE:
<223> OTHER INFORMATION: Synthetic oligonucleotide: TMVTag5

<400> SEQUENCE: 207
acaattacta tttacaatta cagtgtctgt acc                                33

<210> SEQ ID NO 208
<211> LENGTH: 33
<212> TYPE: DNA
<213> ORGANISM: Artificial Sequence
<220> FEATURE:
<223> OTHER INFORMATION: Synthetic oligonucleotide: TMVTag6

<400> SEQUENCE: 208
acaattacta tttacaatta cagtttggct acc                                33

<210> SEQ ID NO 209
<211> LENGTH: 50
<212> TYPE: DNA
<213> ORGANISM: Artificial Sequence
<220> FEATURE:
<223> OTHER INFORMATION: Synthetic oligonucleotide: T7TMVTag5s

<400> SEQUENCE: 209
taatacgact cactataggg acaattacta tttacaatta cagtgtctgt              50

<210> SEQ ID NO 210
<211> LENGTH: 50
<212> TYPE: DNA
<213> ORGANISM: Artificial Sequence
<220> FEATURE:
<223> OTHER INFORMATION: Synthetic oligonucleotide: T7TMVTag6s

<400> SEQUENCE: 210
taatacgact cactataggg acaattacta tttacaatta cagtttggct              50

<210> SEQ ID NO 211
<211> LENGTH: 10
<212> TYPE: RNA
<213> ORGANISM: Artificial Sequence
<220> FEATURE:
<223> OTHER INFORMATION: Synthetic oligonucleotide: linker sequence

<400> SEQUENCE: 211
uagcggaugc                                                          10

<210> SEQ ID NO 212
<211> LENGTH: 32
<212> TYPE: DNA
<213> ORGANISM: Artificial Sequence
<220> FEATURE:
<223> OTHER INFORMATION: Synthetic oligonucleotide
```

```
<400> SEQUENCE: 212
acttccgcca ccgccagacc ctccaccgcc gc                                      32
```